(12) United States Patent
Schatz et al.

(10) Patent No.: US 7,695,906 B2
(45) Date of Patent: Apr. 13, 2010

(54) METHOD FOR THE MANUFACTURE OF NUCLEIC ACID MOLECULES

(76) Inventors: Octavian Schatz, Steinbergstrasse 30, D-85250 Altomüster (DE); Timothy O'Connell, Asambogen 48, D-82256 Fürstenfeldbruck (DE); Heinz Schwer, Wember-von-Braun-Str. 3, D-82256 Fürstenfeldbruck (DE); Thomas Waldmann, Perlacher Str. 80e, D-81539 München (DE)

( * ) Notice: Subject to any disclaimer, the term of this patent is extended or adjusted under 35 U.S.C. 154(b) by 388 days.

(21) Appl. No.: 10/531,556

(22) PCT Filed: Oct. 17, 2003

(86) PCT No.: PCT/EP03/11551

§ 371 (c)(1), (2), (4) Date: Apr. 14, 2005

(87) PCT Pub. No.: WO2004/035781

PCT Pub. Date: Apr. 29, 2004

(65) Prior Publication Data

US 2006/0194202 A1    Aug. 31, 2006

(30) Foreign Application Priority Data

Oct. 18, 2002    (EP) .................................. 02023385

(51) Int. Cl.
*C12Q 1/68*    (2006.01)
(52) U.S. Cl. ........................................................ 435/6
(58) Field of Classification Search ........................ None
See application file for complete search history.

(56) References Cited

U.S. PATENT DOCUMENTS 5,397,698 A    3/1995    Goodman et al.

FOREIGN PATENT DOCUMENTS

| EP | 20010127864 | 11/2001 |
|---|---|---|
| WO | WO 95/17413 A | 6/1995 |
| WO | WO 99/47536 | 9/1999 |
| WO | WO 00/75364 | 6/2000 |
| WO | WO 00/75368 | 6/2000 |
| WO | WO0075368 | * 12/2000 |

OTHER PUBLICATIONS

Shao-Chi Huang et al., "Binding of biotinylated DNA to Streptavidin-Coated Polystryrene Latex." 222 Analytical Biochemistry (1994) 441-449.

* cited by examiner

*Primary Examiner*—Kenneth R. Horlick
*Assistant Examiner*—David C Thomas
(74) *Attorney, Agent, or Firm*—Polsinelli Shughart PC; Lisa V. Mueller

(57) ABSTRACT

The present invention is related to a method for the manufacture of a nucleic acid molecule and compounds used therefore. The invention further provides a method of ligating, cleaving and immobilising oligonucleotides in order to manufacture nucleic acid molecules. The invention includes the steps wherein a first and second at least partially double-stranded oligonucleotides are ligated via their respective single-stranded overhangs. The ligation product may be immobilised to the surface via the modification that is provided on the first oligonucleotide. The immobilised ligation product is cleaved with the first type IIS restriction enzyme therein releasing an elongated oligonucleotide having an overhang. The elongated oligonucleotide may further be combined and ligated with a further at least partially double-stranded oligonucleotide to form a further ligated product that may be cleaved with a type IIS restriction enzyme releasing an elongated oligonucleotide having an overhang. The steps may be further repeated in various combinations.

16 Claims, 26 Drawing Sheets

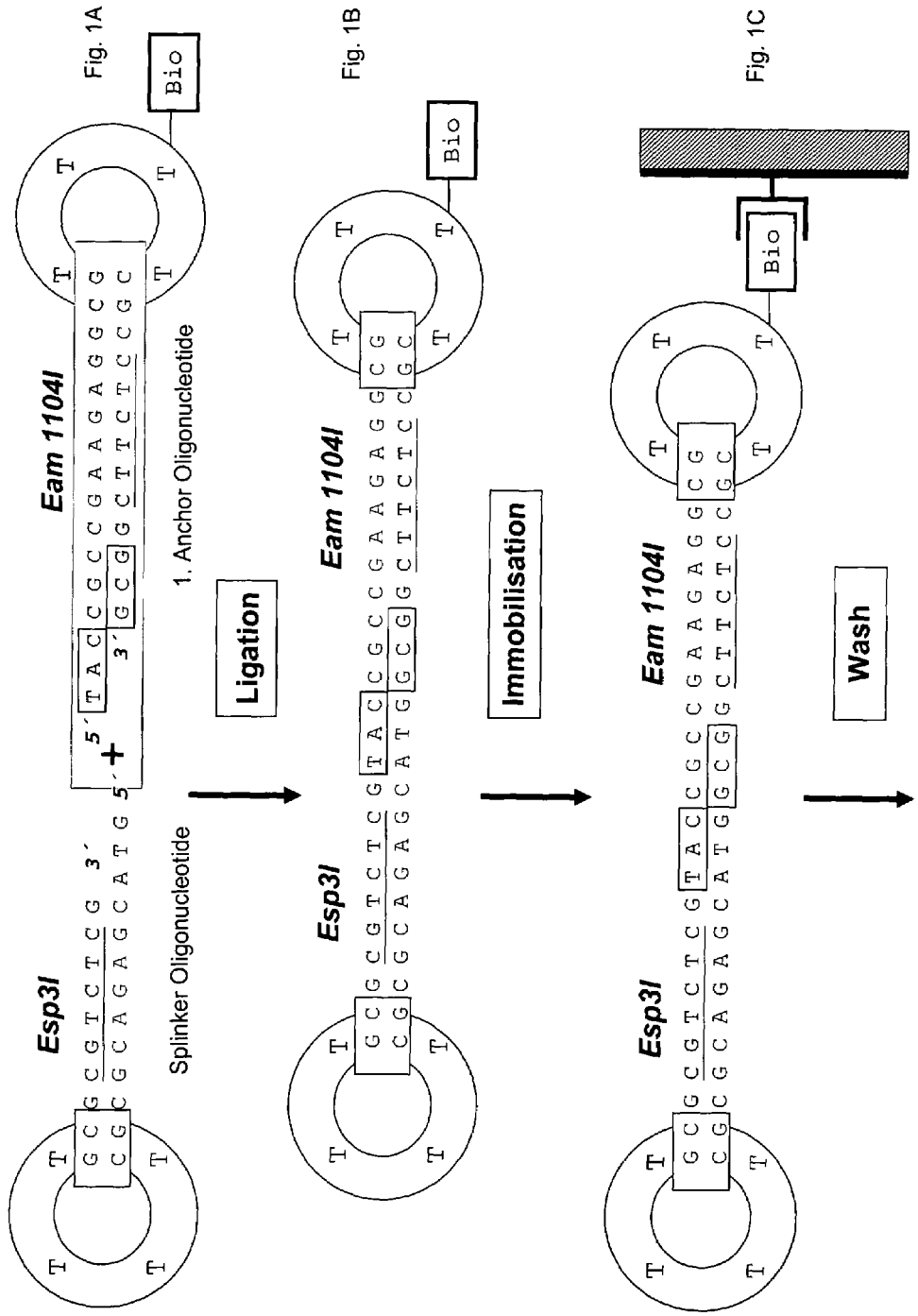

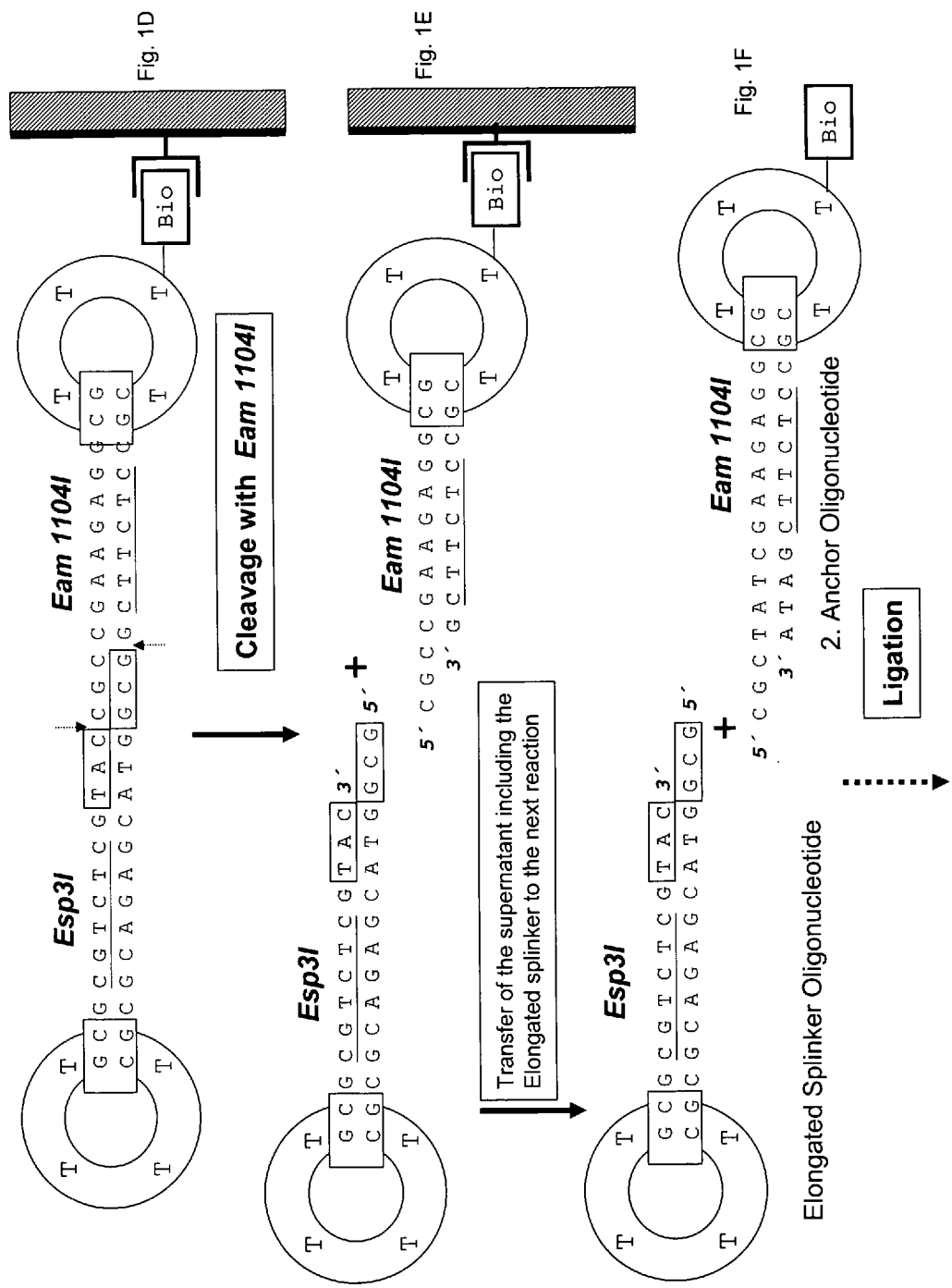

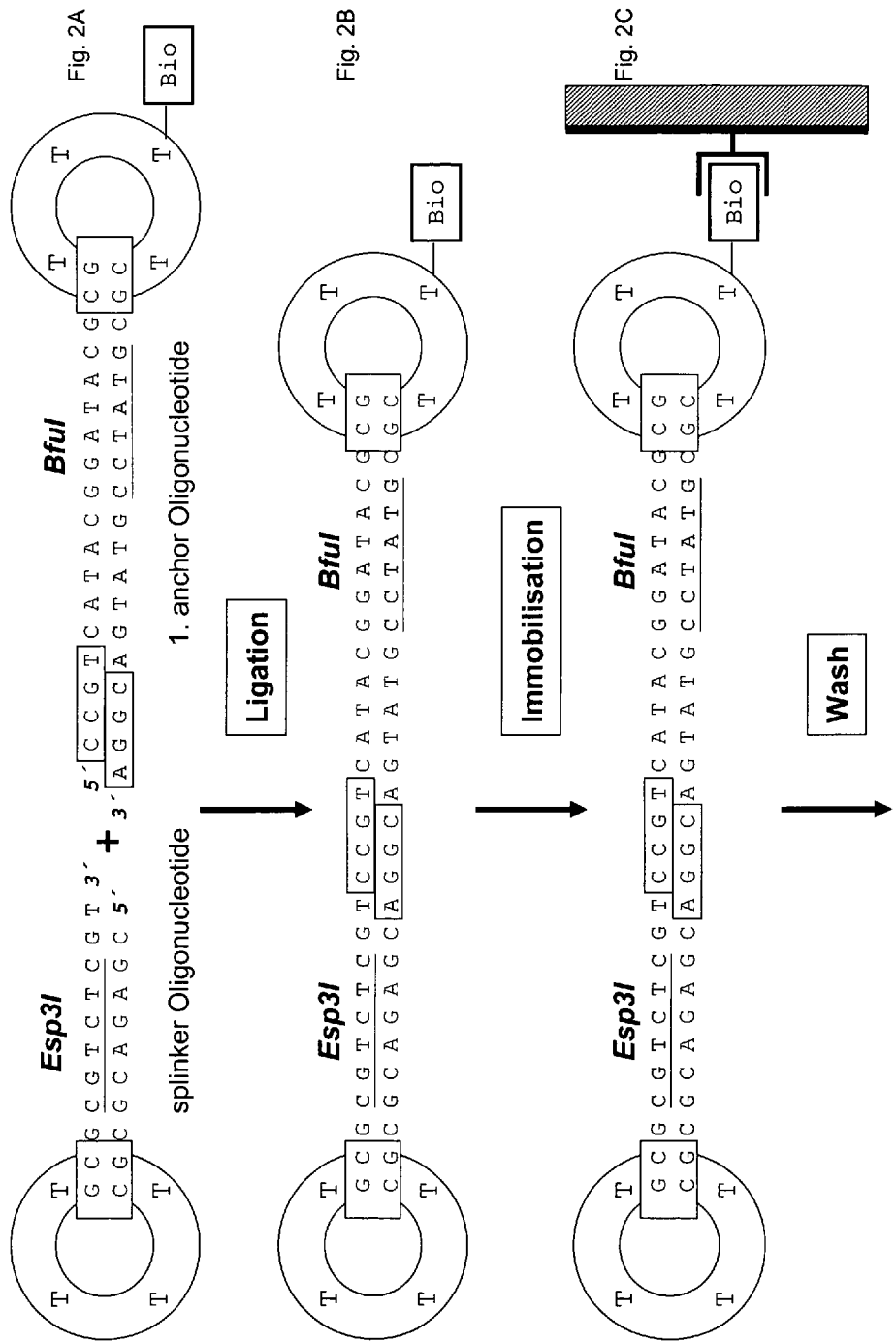

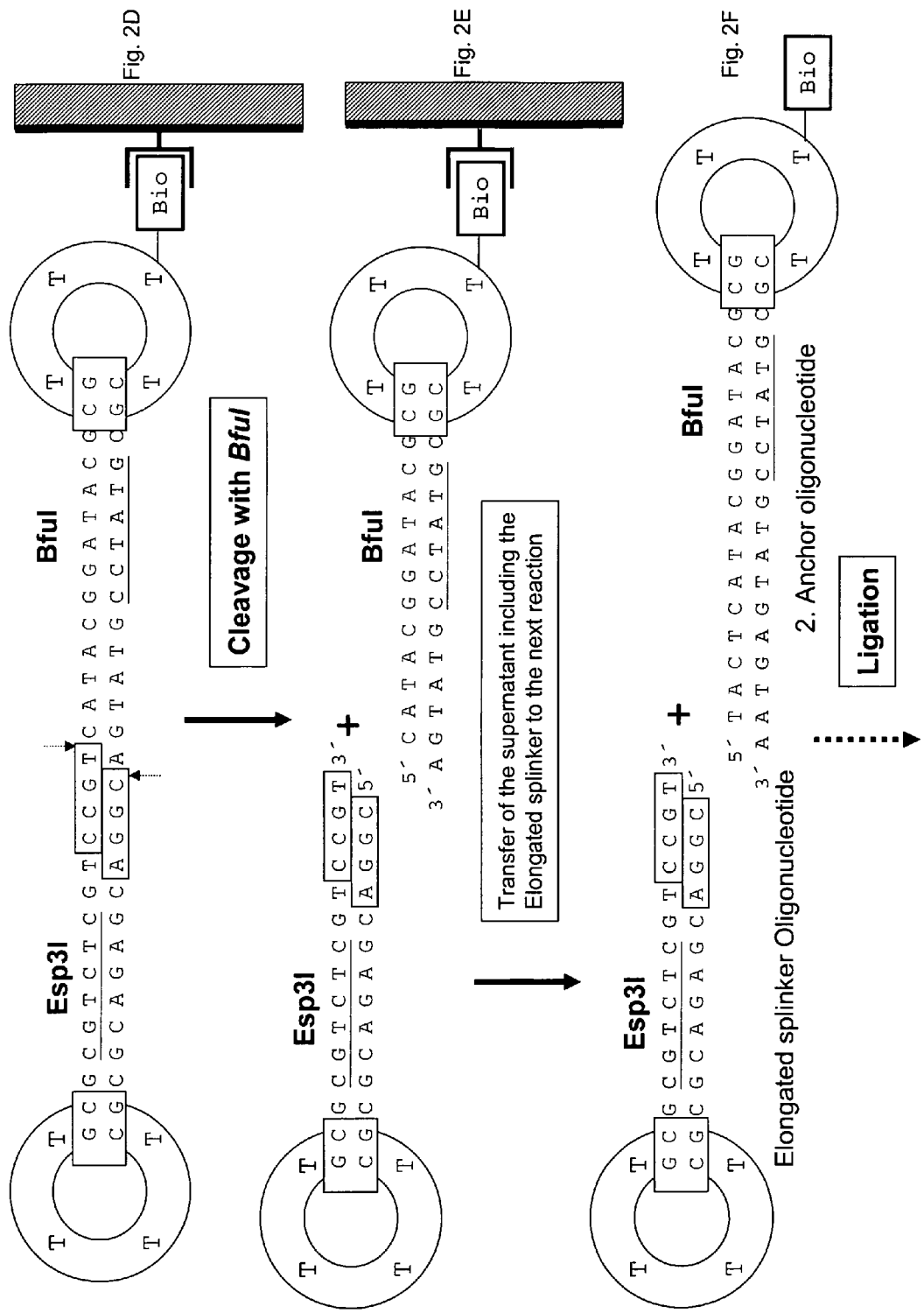

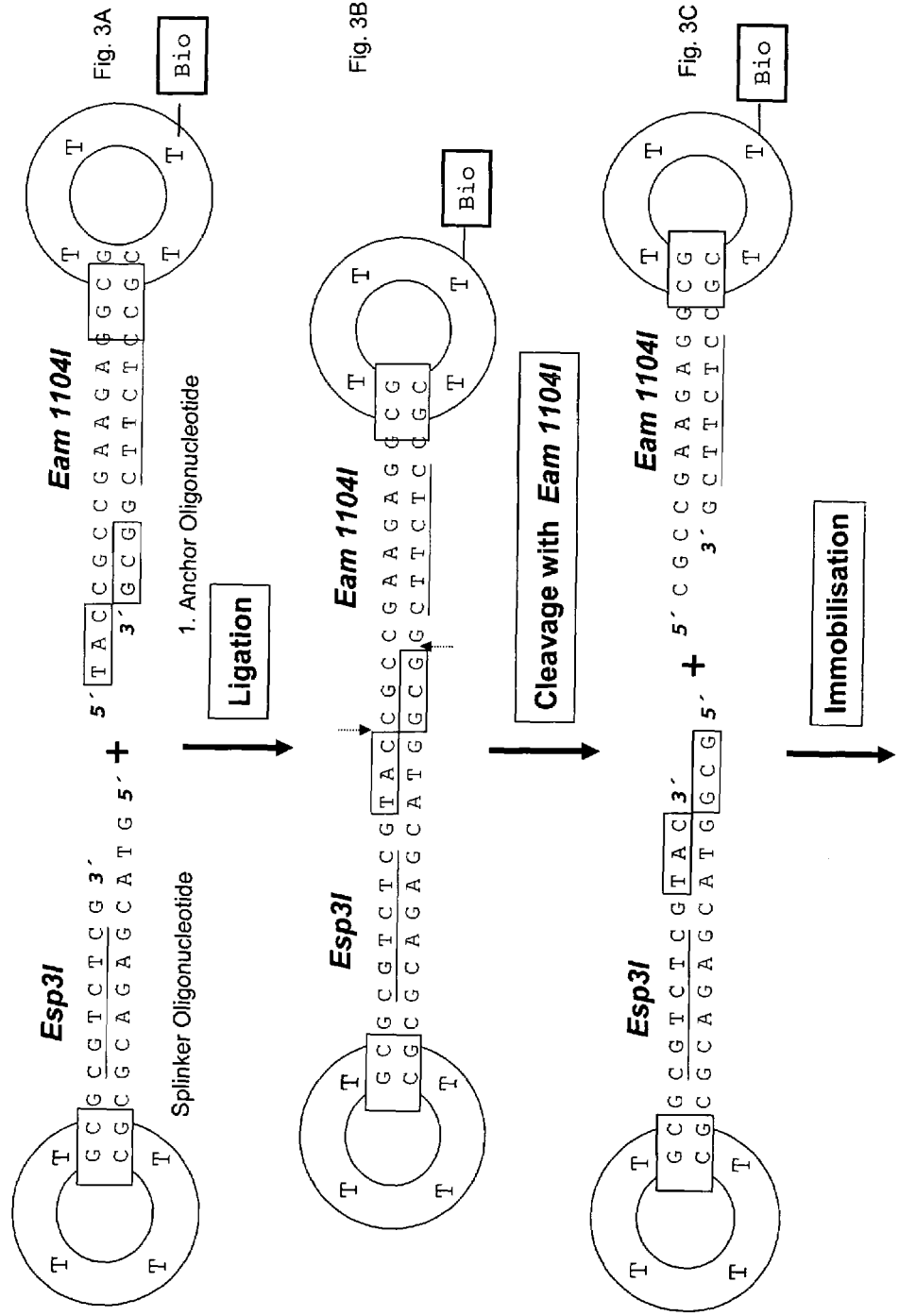

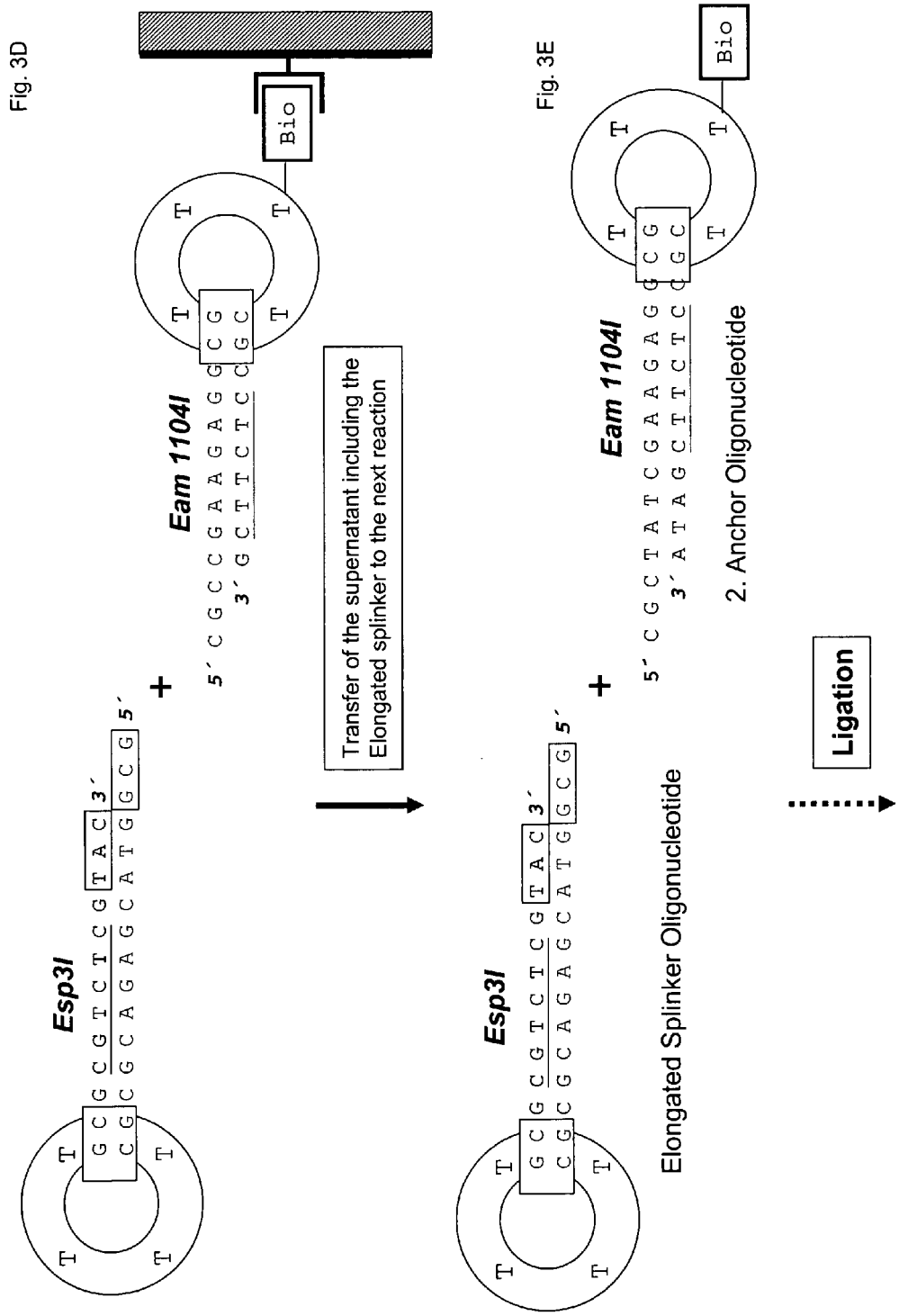

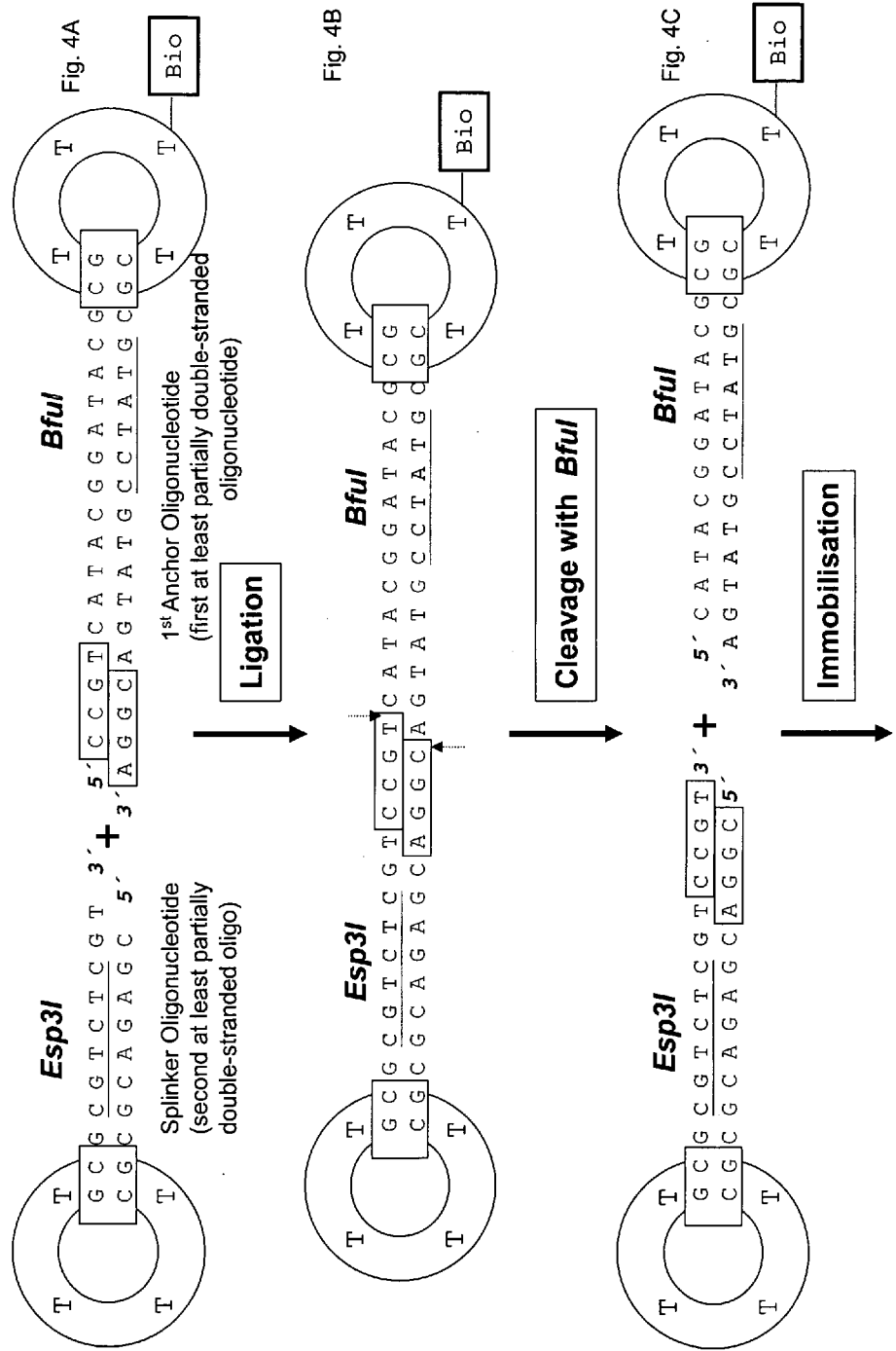

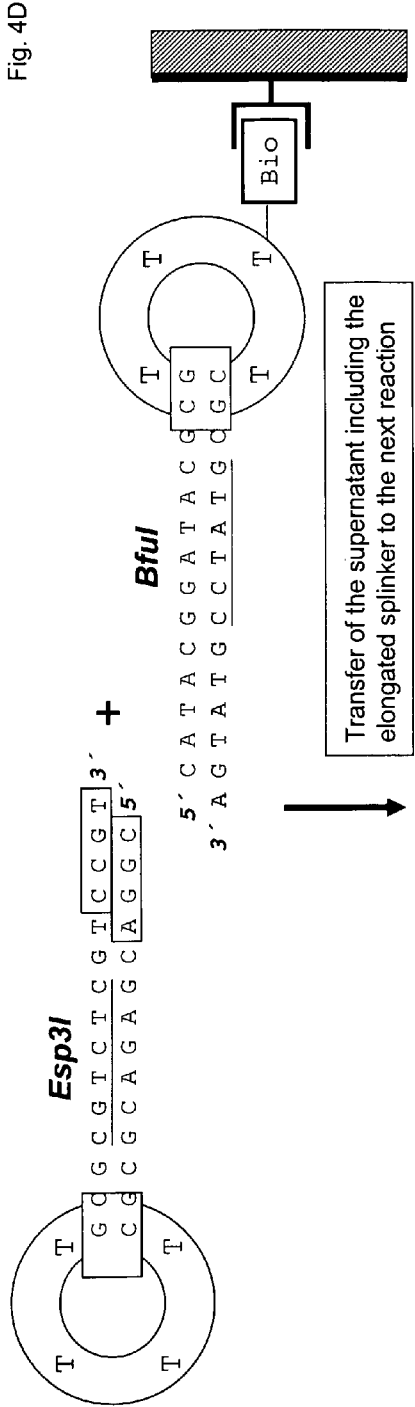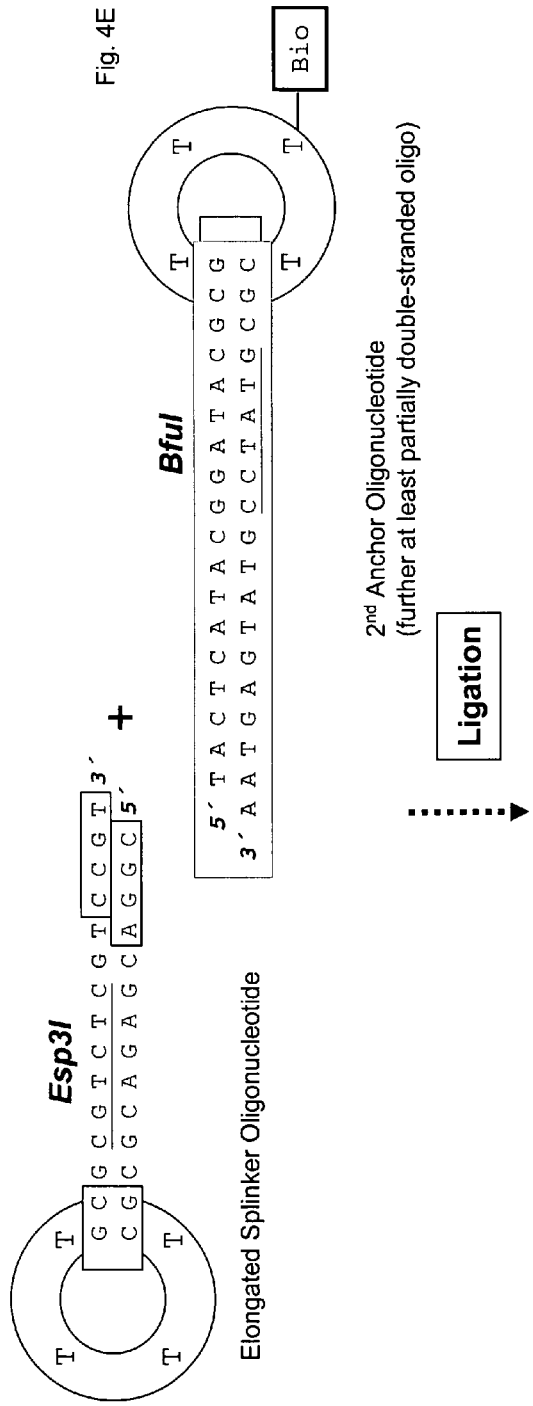

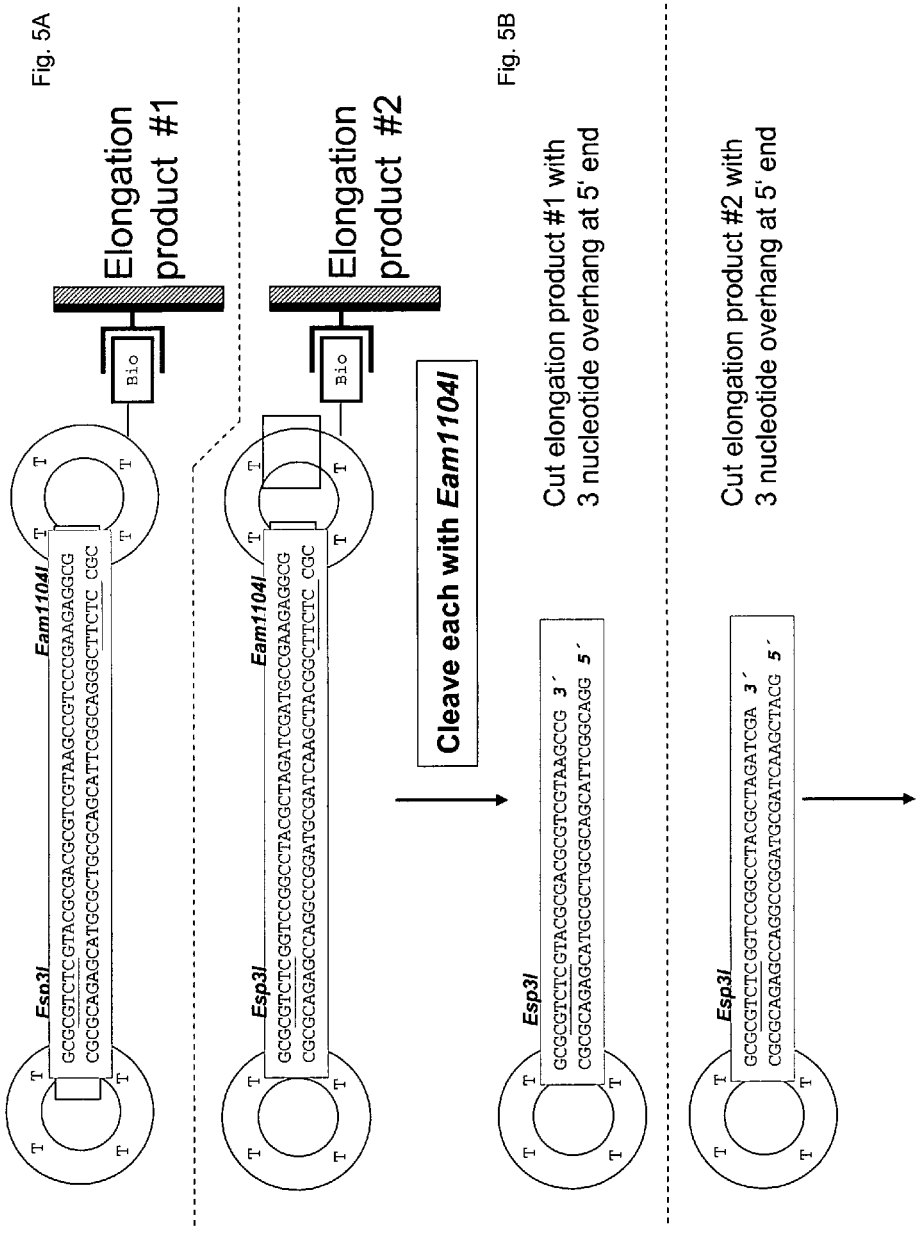

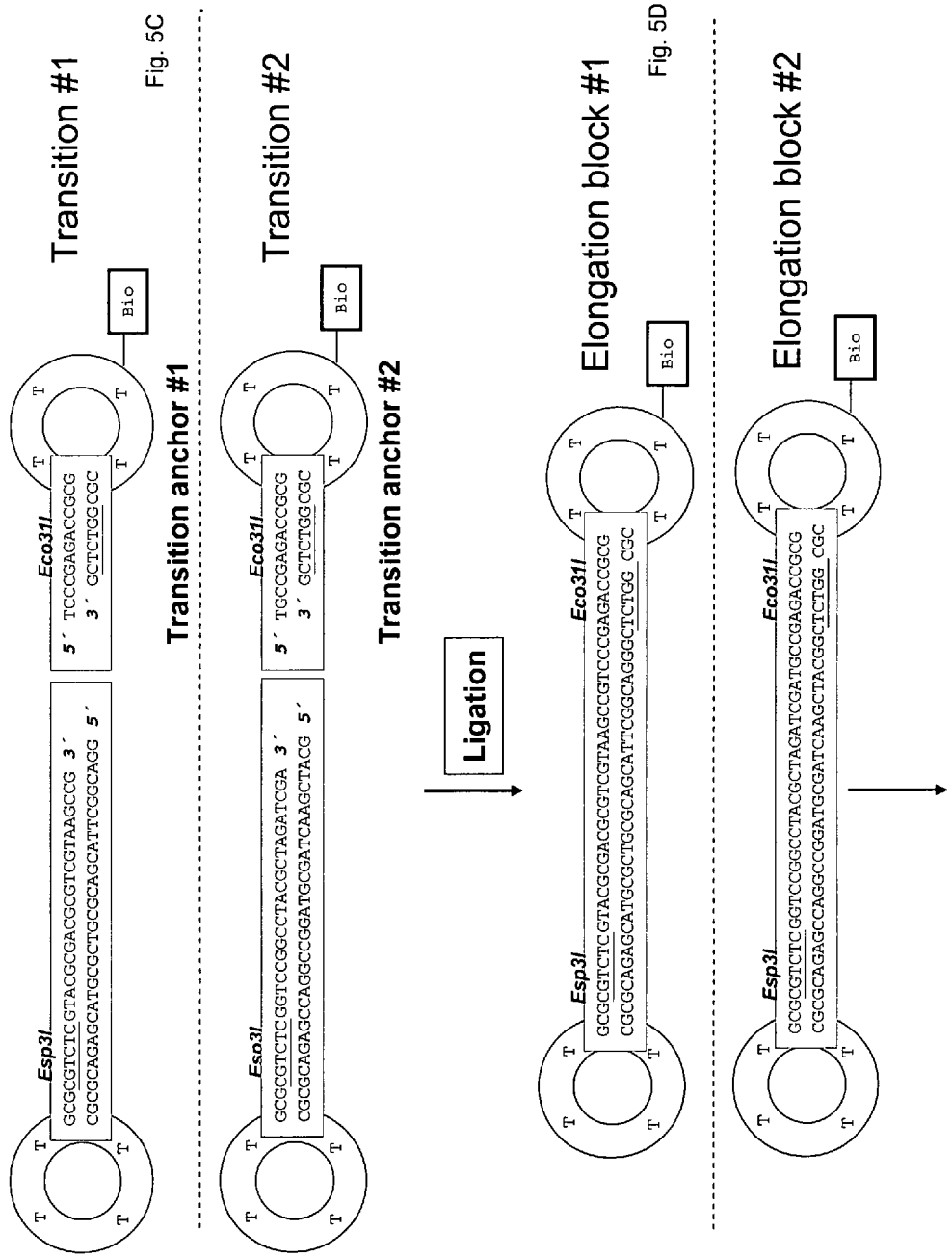

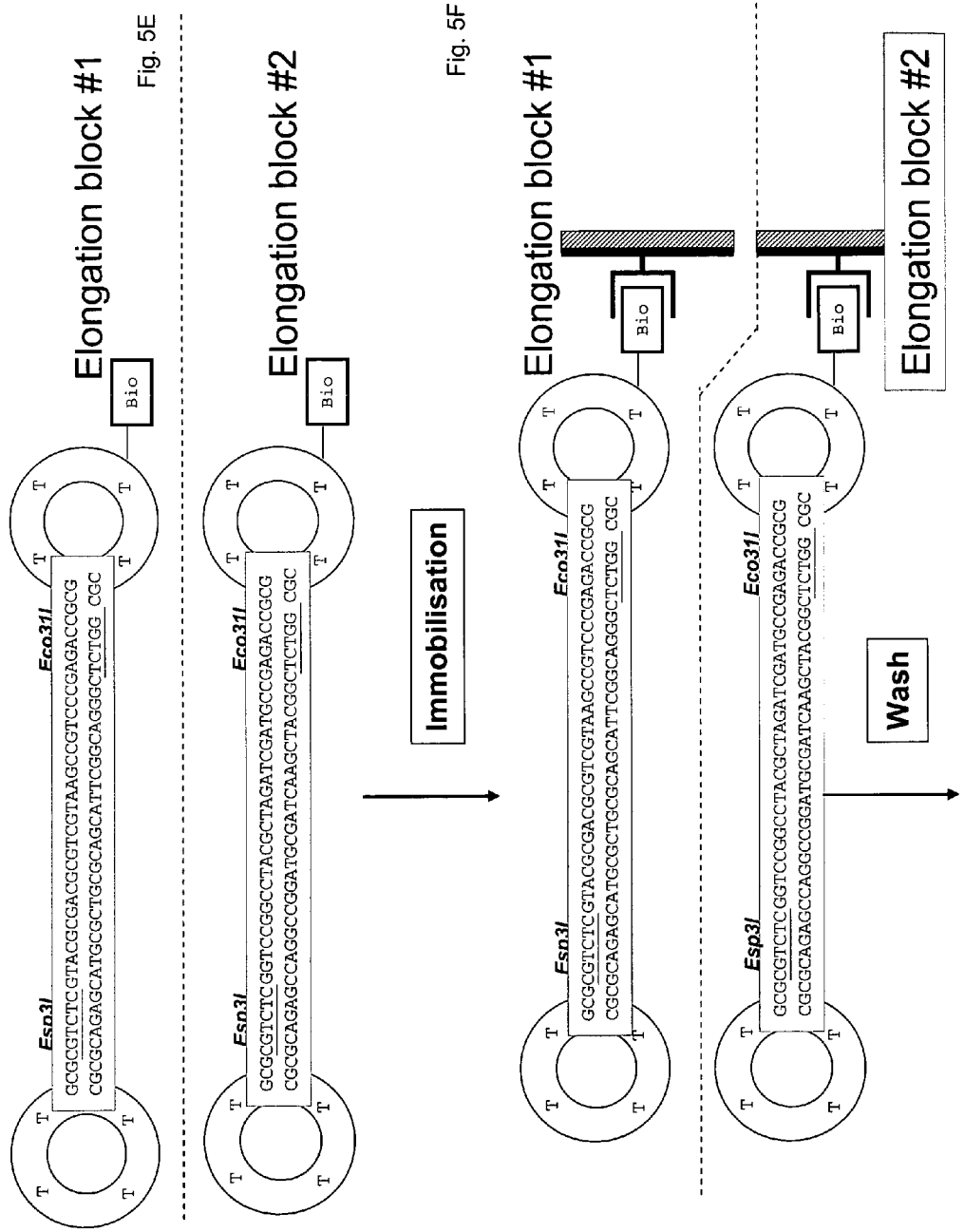

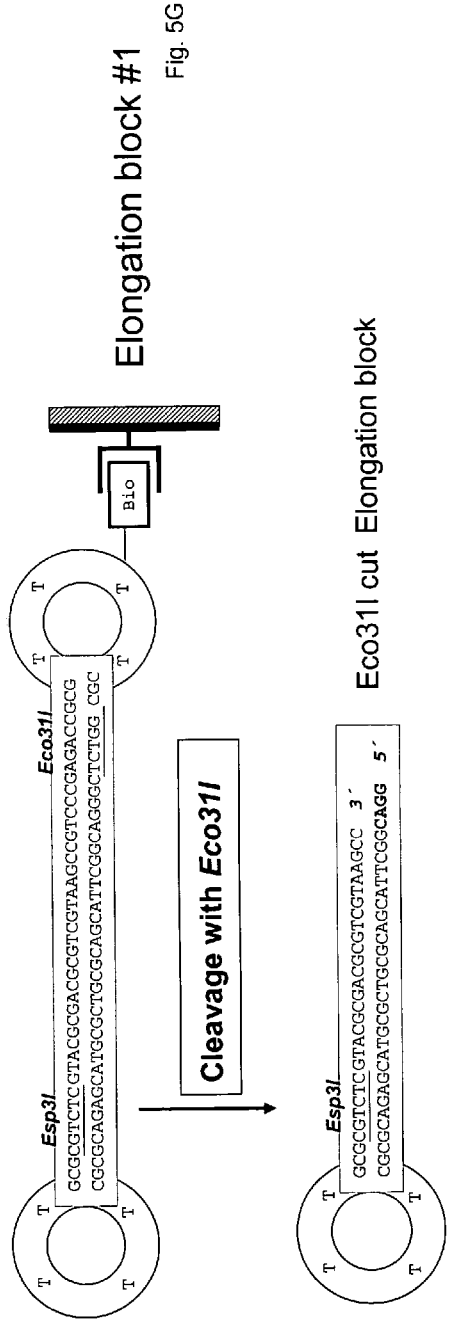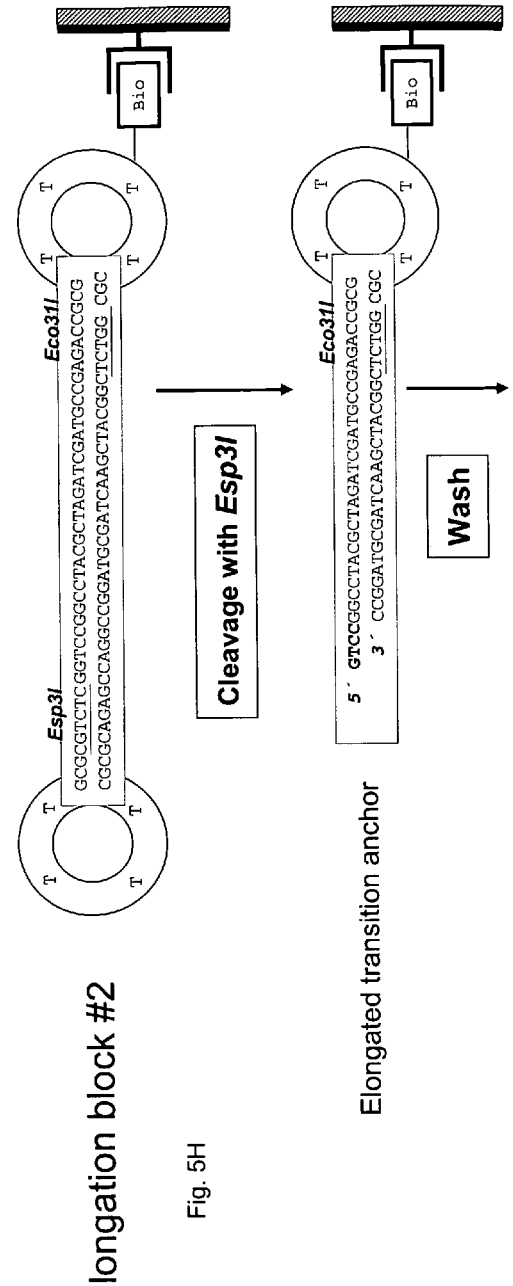

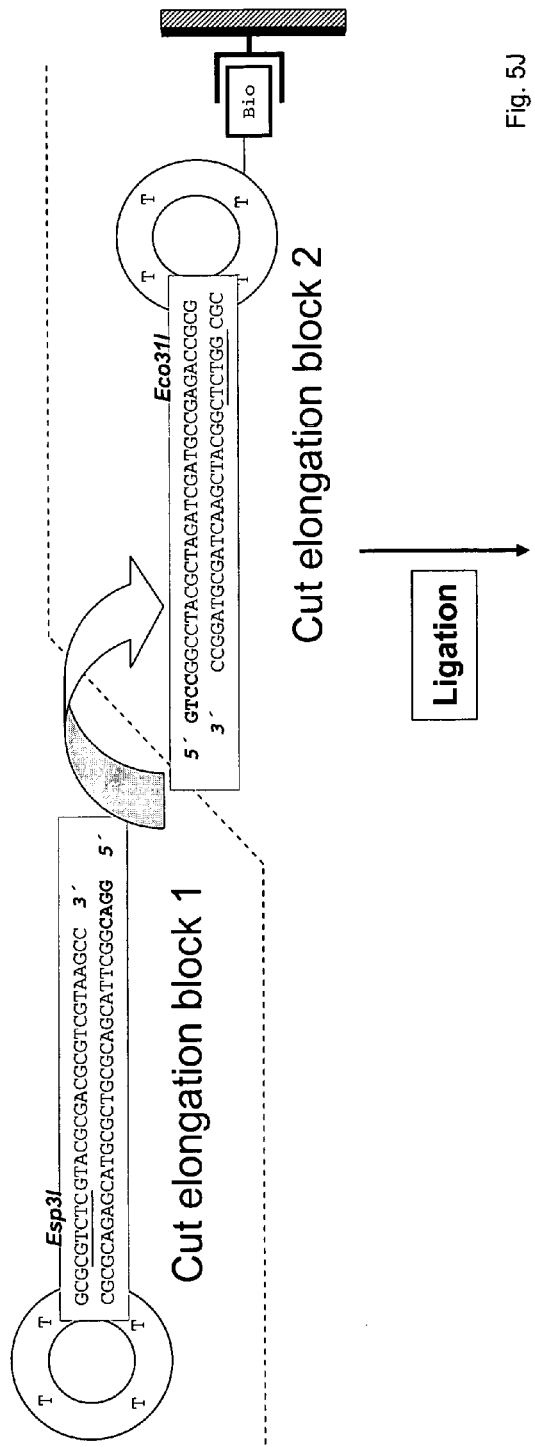
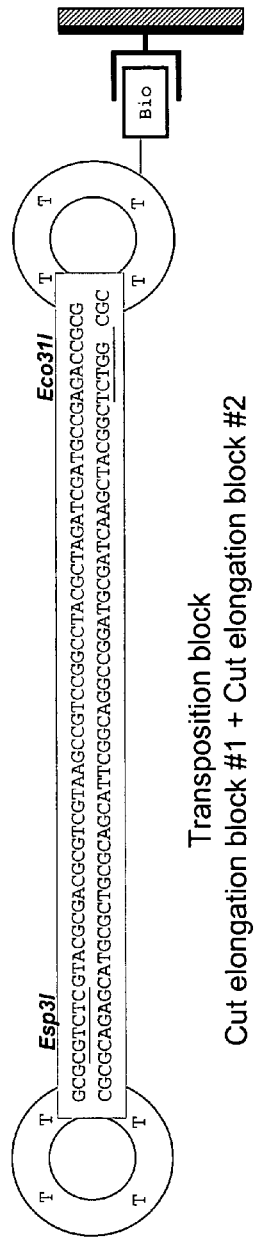
Fig. 5I
Fig. 5J

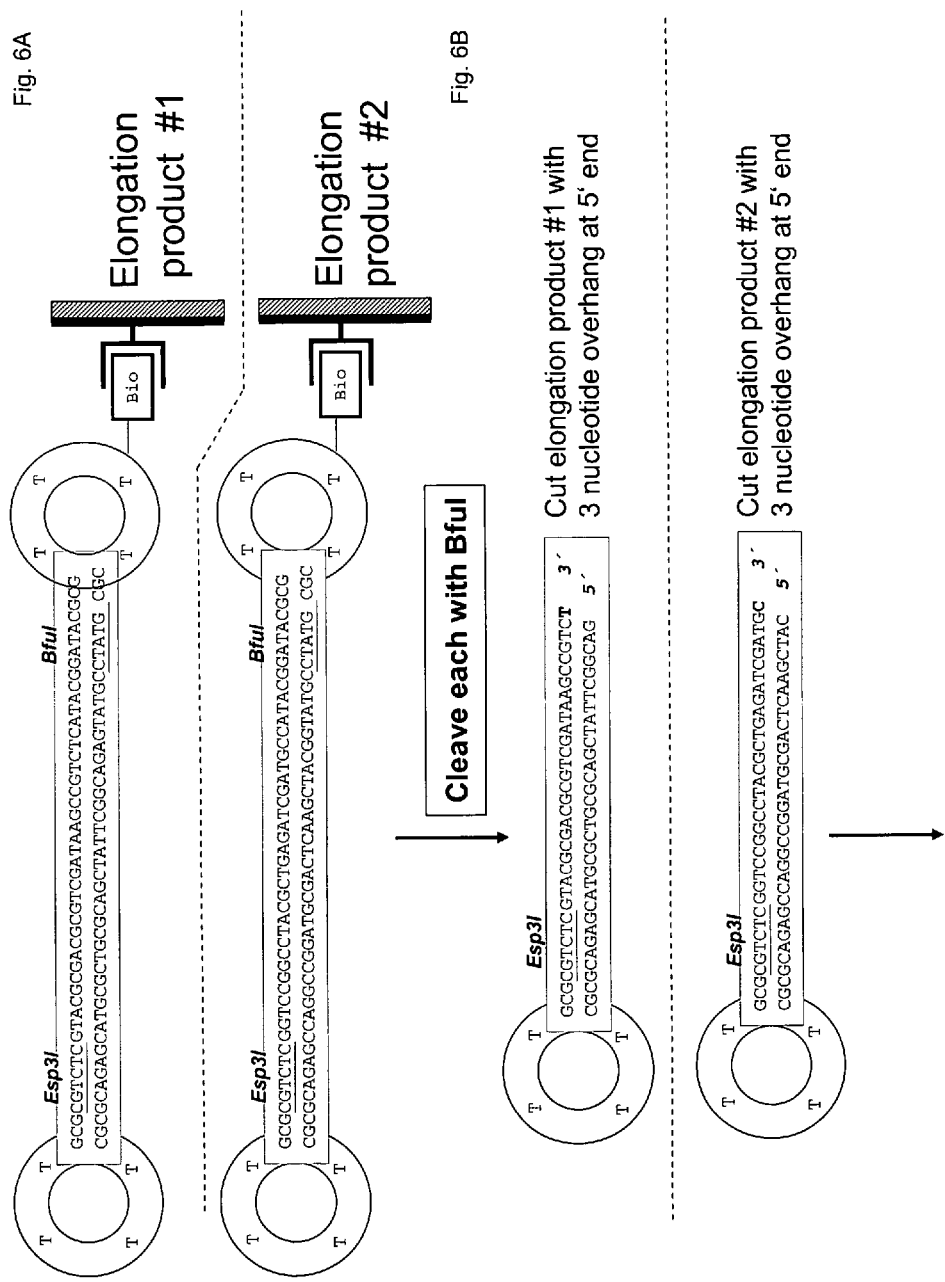

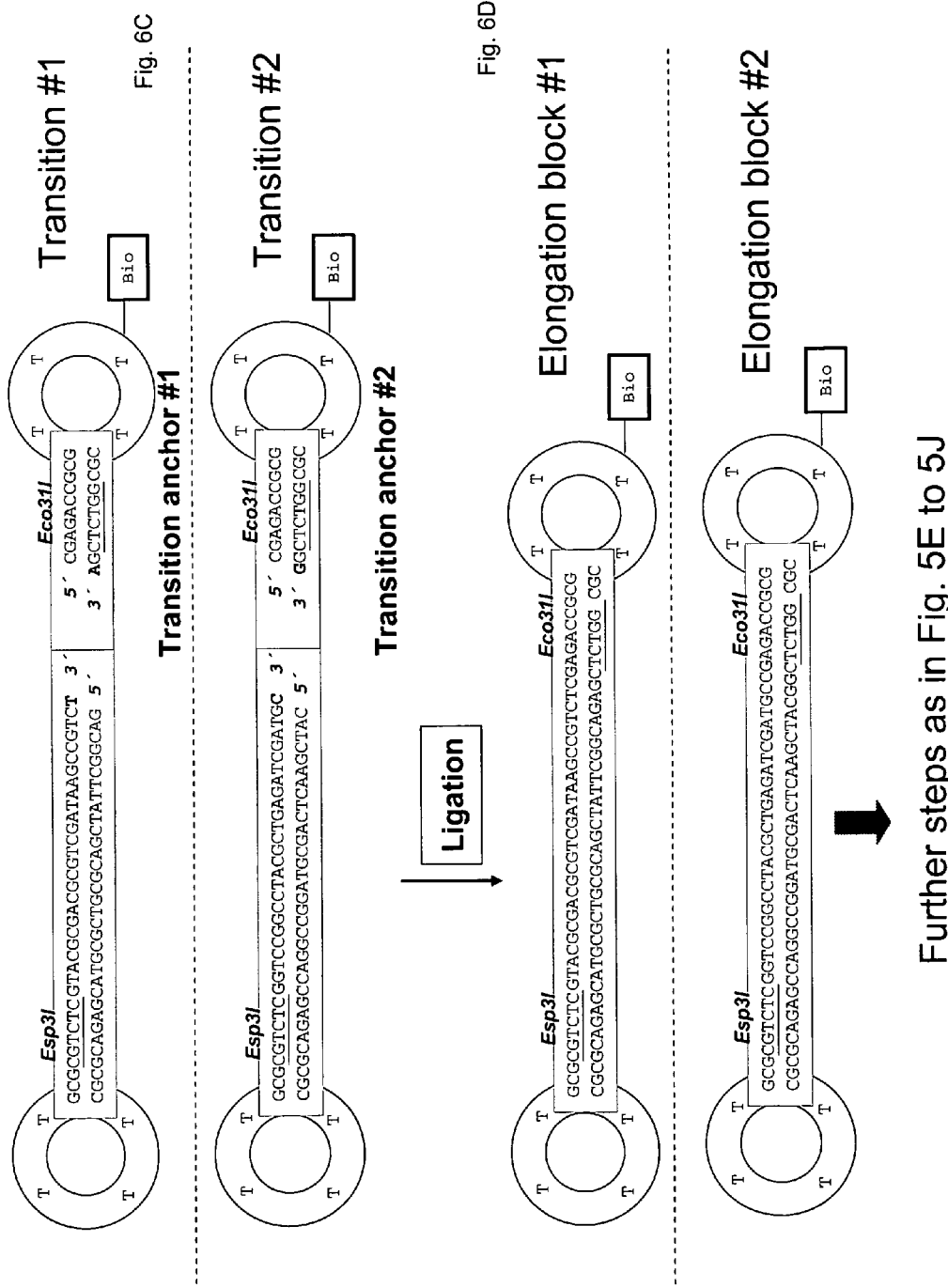

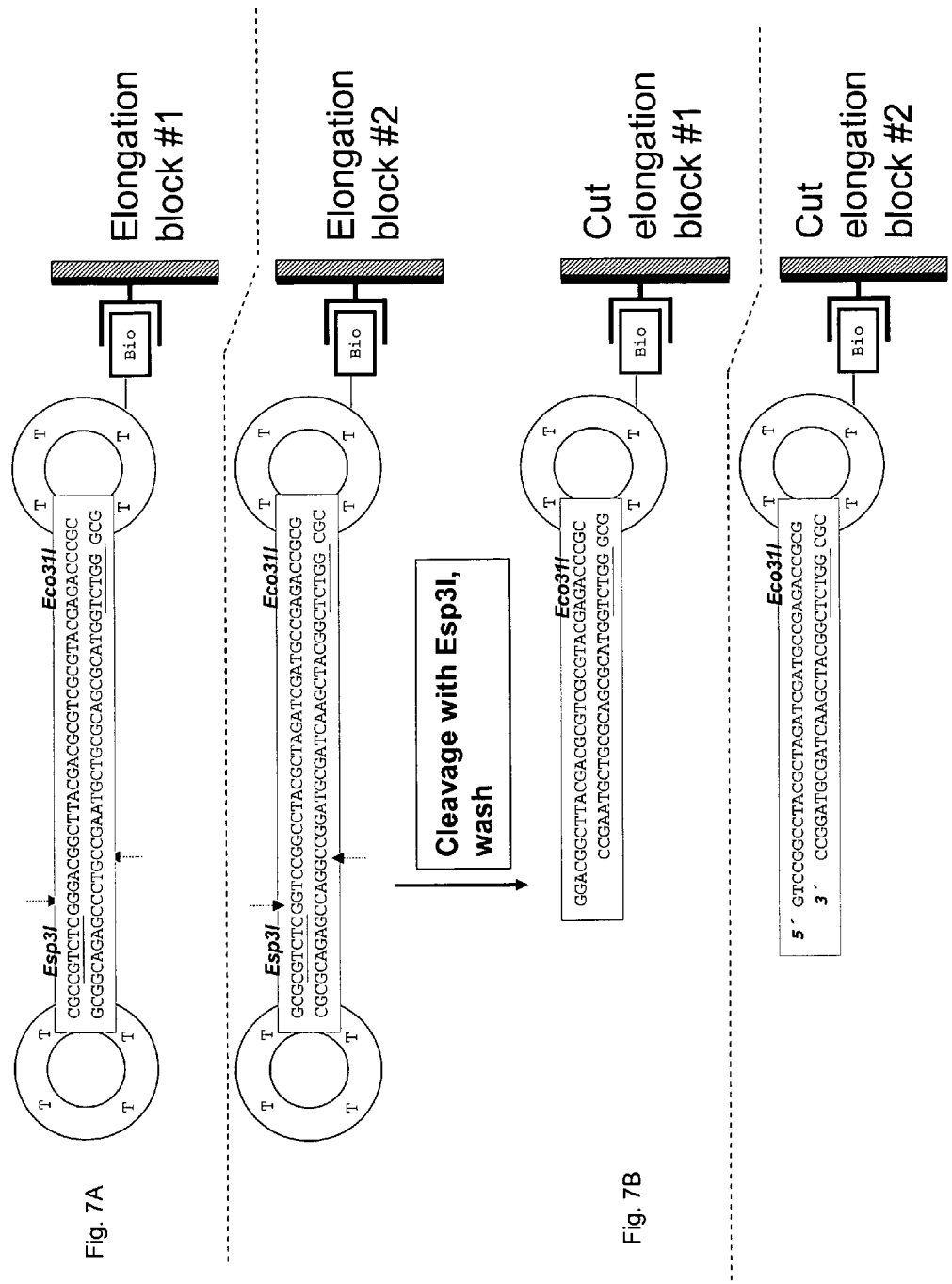

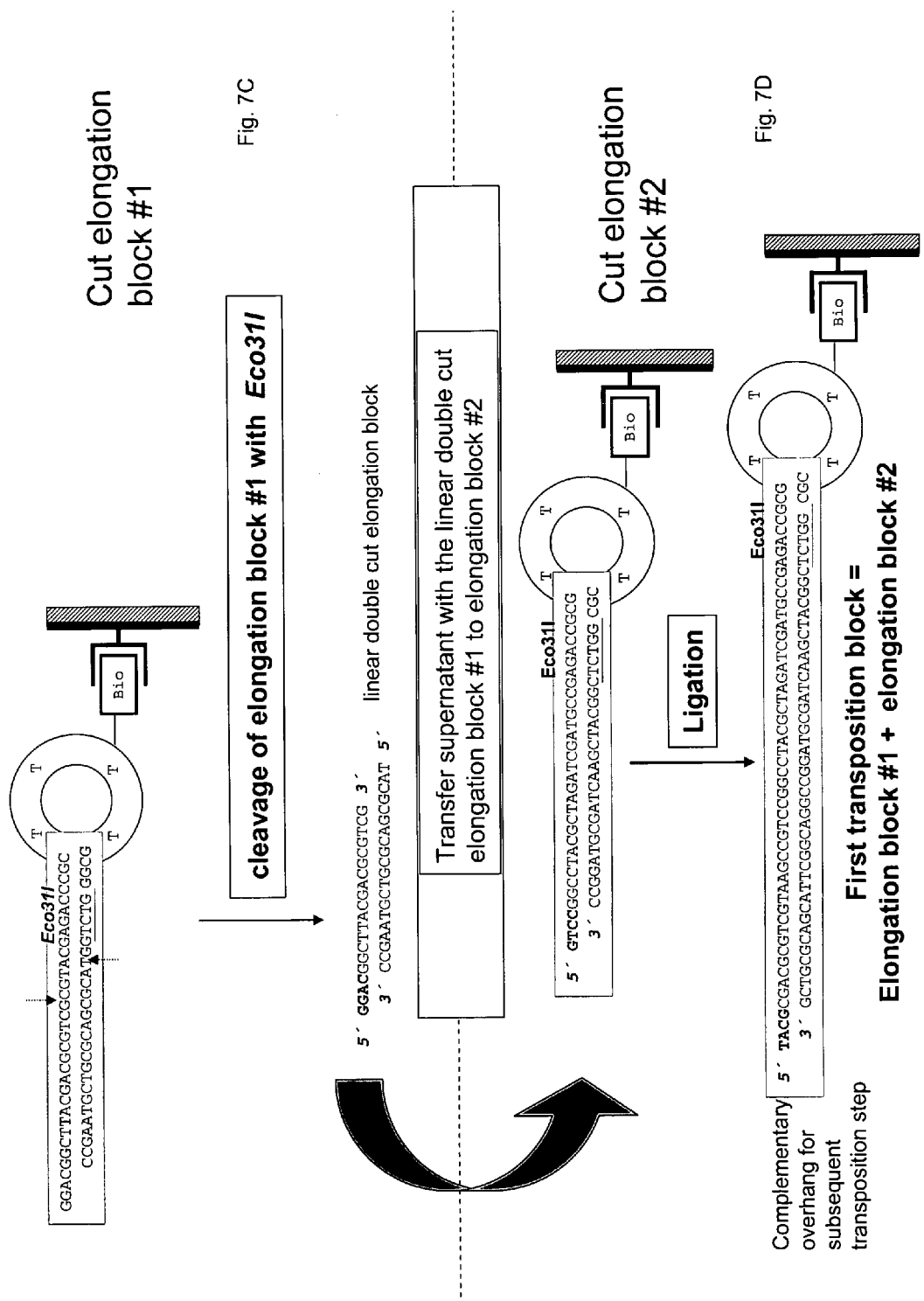

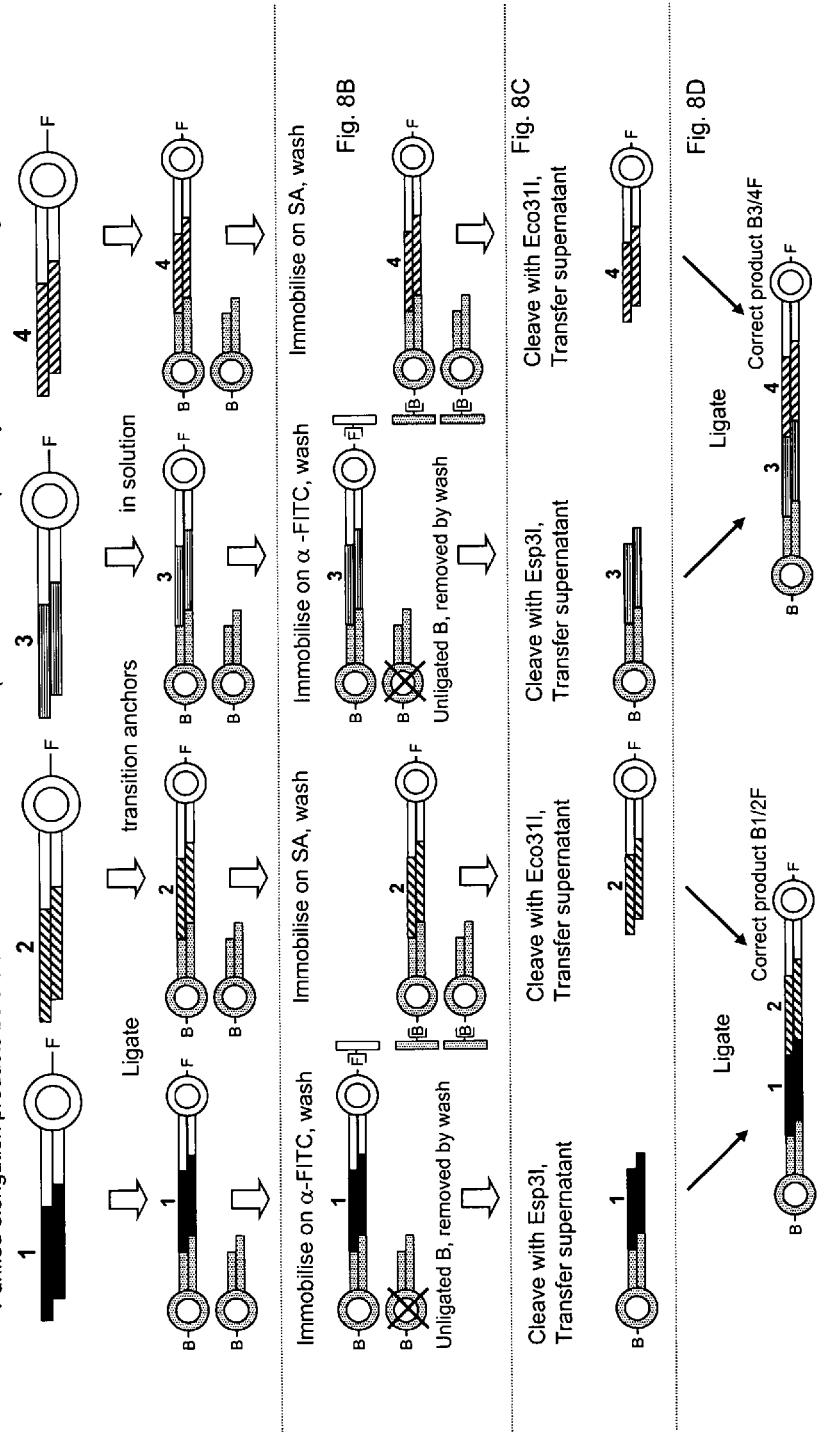

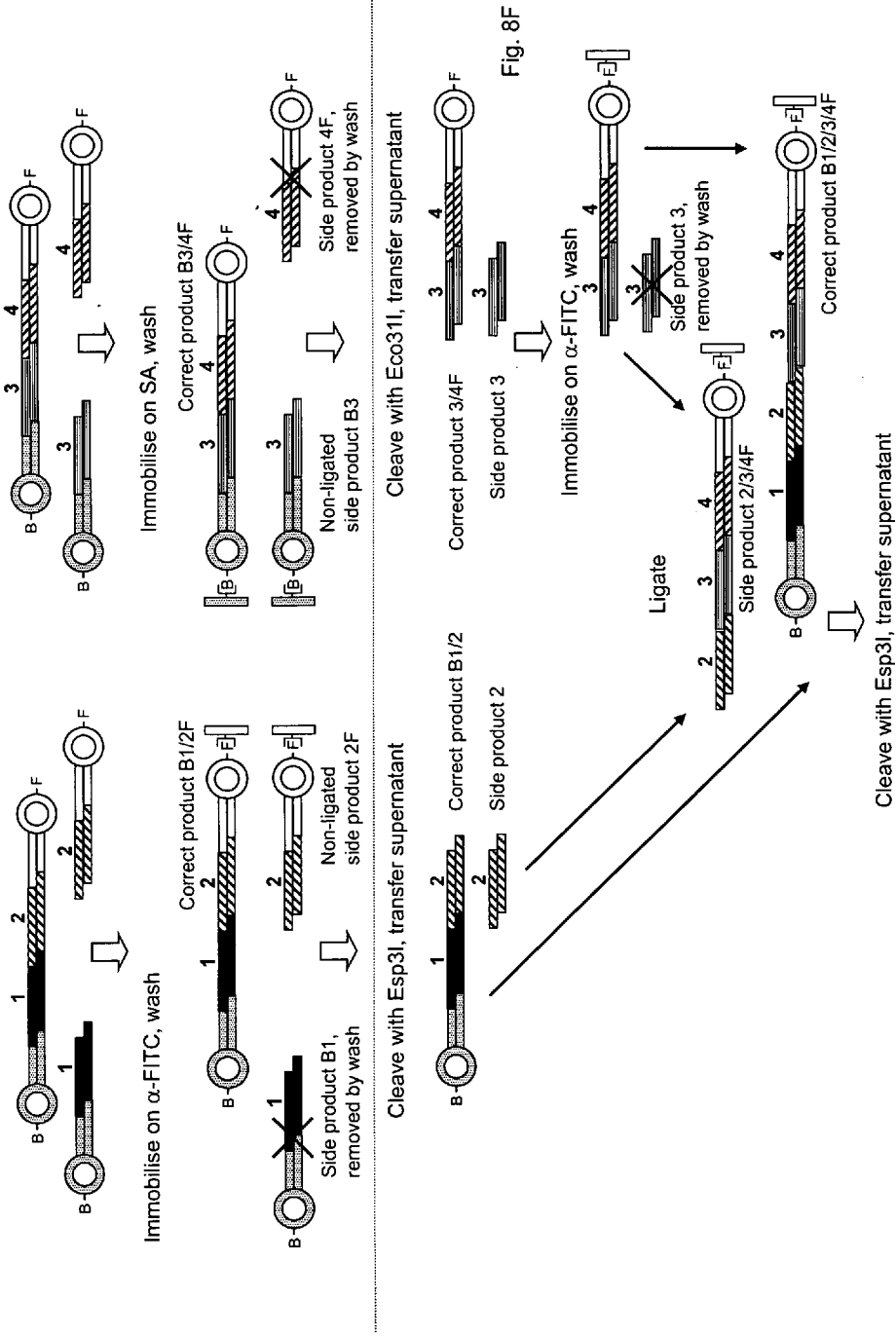

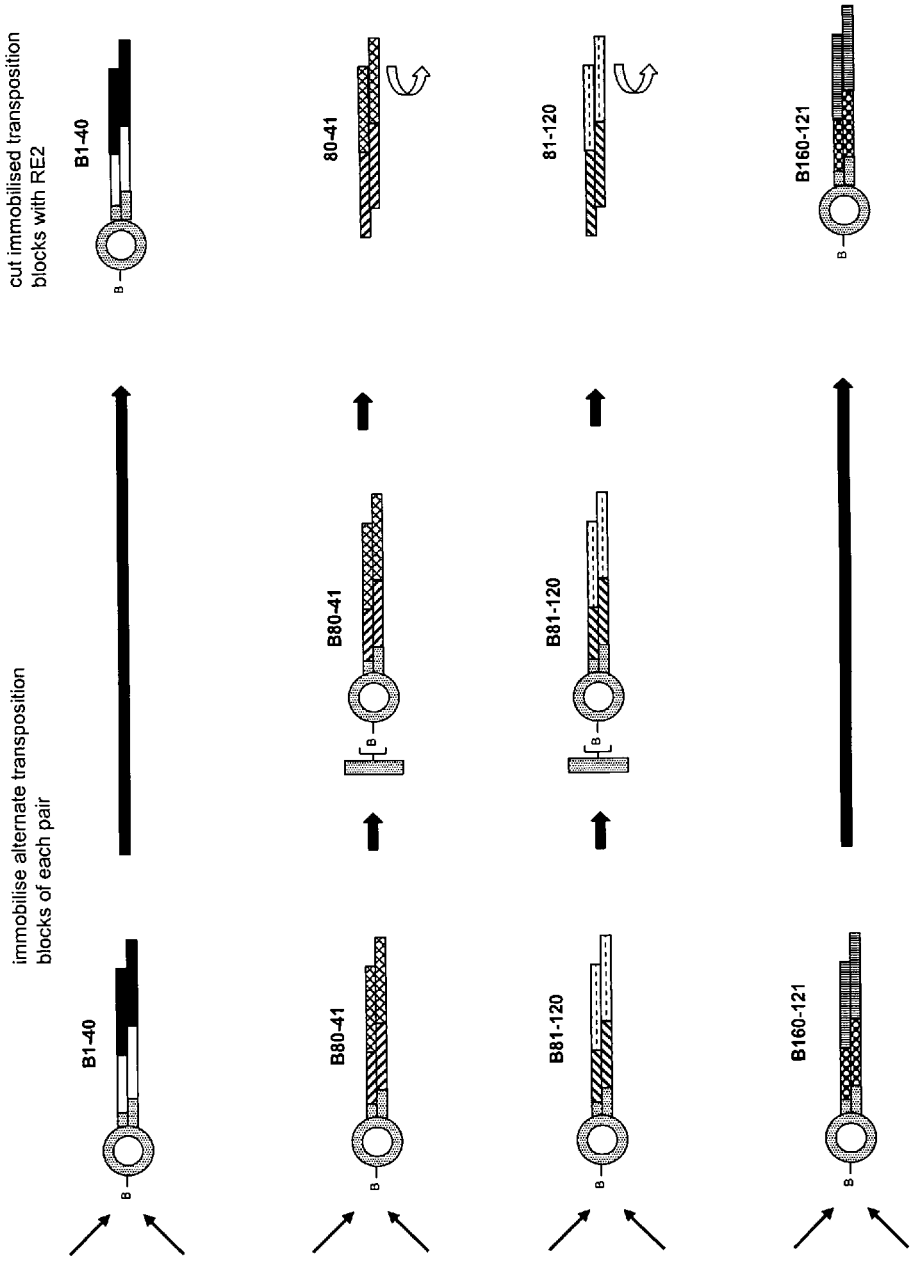

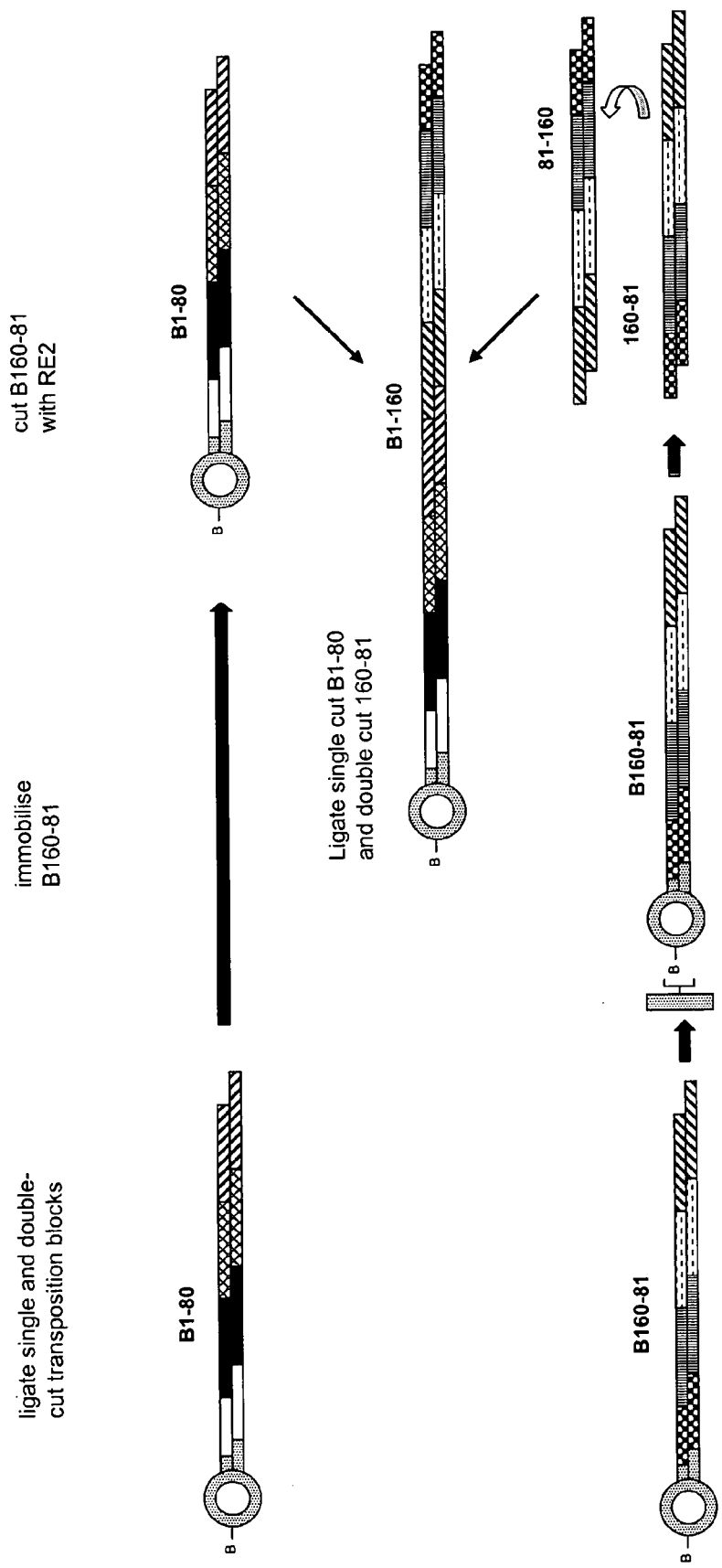
Fig. 9C Semi-inverted transposition (SIT) with prior double selection Fig. 10
Design of elongation blocks for standard and semi-inverted transpositions
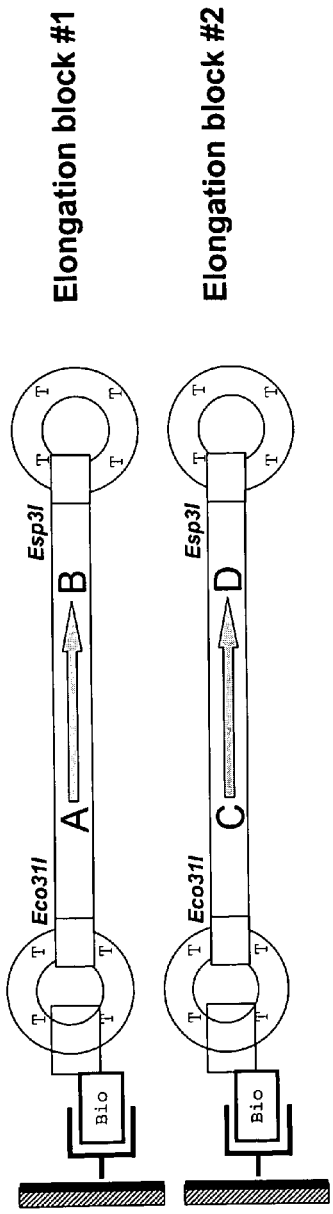
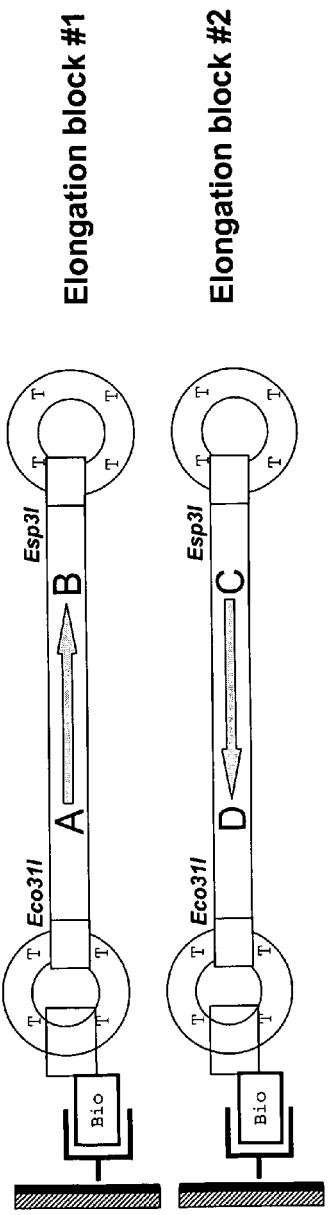

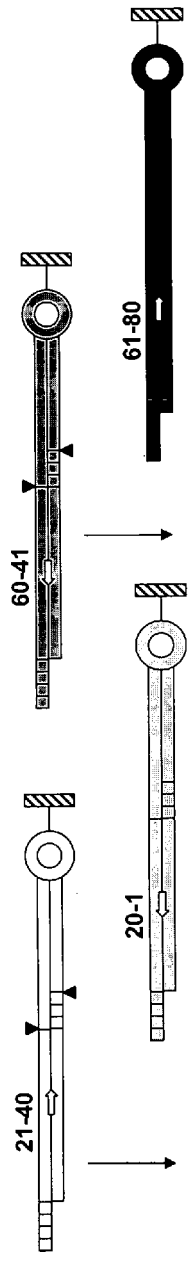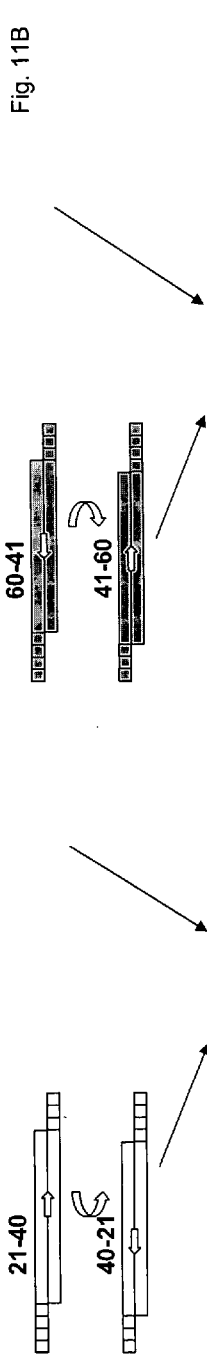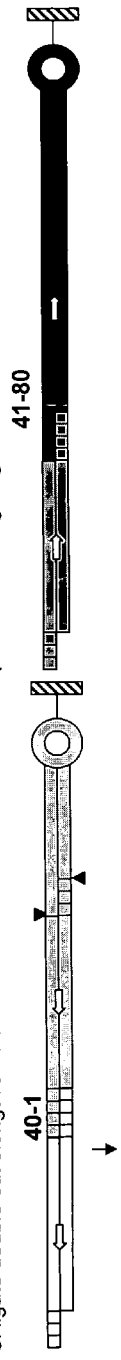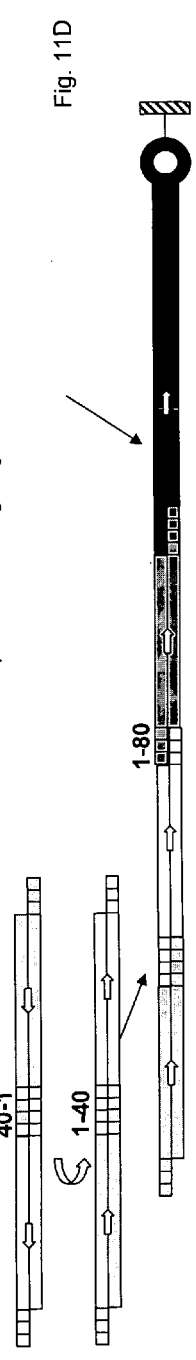

Semi-inverted transposition (SIT) with 3nt/4nt ligation 1. cleave all immobilised elongation blocks with RE specific for second at least partially double-stranded oligonucleotide

Fig. 11A 2. cleave every other cut immobilised elongation block with RE specific for further at least partially double-stranded oligonucleotide

Fig. 11B 3. ligate double cut elongation blocks in inverse orientation with the respective matching single cut immobilised elongation blocks

Fig. 11C 4. cleave every other immobilised transposition block with the same RE as before, ligate double cut transposition blocks in reverse orientation with their respective matching single cut immobilised transposition blocks

Fig. 11D

SEQUENCE LISTING

```
<160> NUMBER OF SEQ ID NOS: 61

<210> SEQ ID NO 1
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 1
cgtctcnnnn n                                                          11

<210> SEQ ID NO 2
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 2
ggtctcnnnn n                                                          11
```

```
<210> SEQ ID NO 3
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: any nucleotide

<400> SEQUENCE: 3
gaagacnnnn nn                                                              12

<210> SEQ ID NO 4
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(14)
<223> OTHER INFORMATION: any nucleotide

<400> SEQUENCE: 4
acctgcnnnn nnnn                                                            14

<210> SEQ ID NO 5
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: any nucleotide

<400> SEQUENCE: 5 gcagtgnn                                                                    8

<210> SEQ ID NO 6
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: any nucleotide

<400> SEQUENCE: 6 gcaatgnn                                                                    8

<210> SEQ ID NO 7
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: any nucleotide

<400> SEQUENCE: 7
gtatccnnnn nn                                                              12
```

```
<210> SEQ ID NO 8
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 8
actgggnnnn n                                                             11

<210> SEQ ID NO 9
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(17)
<223> OTHER INFORMATION: any nucleotide

<400> SEQUENCE: 9
ggcggannnn nnnnnnn                                                       17

<210> SEQ ID NO 10
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(16)
<223> OTHER INFORMATION: any nucleotide

<400> SEQUENCE: 10
gaggagnnnn nnnnnn                                                        16

<210> SEQ ID NO 11
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(15)
<223> OTHER INFORMATION: any nucleotide

<400> SEQUENCE: 11
cacctgcnnn nnnnn                                                         15

<210> SEQ ID NO 12
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(17)
<223> OTHER INFORMATION: any nucleotide

<400> SEQUENCE: 12
cagctcnnnn nnnnnnn                                                       17
```

```
<210> SEQ ID NO 13
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(11)
<223> OTHER INFORMATION: any nucleotide

<400> SEQUENCE: 13
gctcttcnnn n                                                        11

<210> SEQ ID NO 14
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: any nucleotide

<400> SEQUENCE: 14 ctcttcnnnn                                                          10

<210> SEQ ID NO 15
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 15
ggtctcnnnn n                                                        11

<210> SEQ ID NO 16
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 16
cgtctcnnnn n                                                        11

<210> SEQ ID NO 17
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(14)
<223> OTHER INFORMATION: any nucleotide

<400> SEQUENCE: 17
acctgcnnnn nnnn                                                     14
```

```
<210> SEQ ID NO 18
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: any nucleotide

<400> SEQUENCE: 18
gaagacnnnn nn                                                        12

<210> SEQ ID NO 19
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: any nucleotide

<400> SEQUENCE: 19 gcaatgnn                                                              8

<210> SEQ ID NO 20
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: any nucleotide

<400> SEQUENCE: 20 gcagtgnn                                                              8

<210> SEQ ID NO 21
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: any nucleotide

<400> SEQUENCE: 21
actgggnnnn n                                                         11

<210> SEQ ID NO 22
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: any nucleotide

<400> SEQUENCE: 22
gtatccnnnn nn                                                        12
```

```
<210> SEQ ID NO 23
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(16)
<223> OTHER INFORMATION: any nucleotide

<400> SEQUENCE: 23
gaggagnnnn nnnnnn                                                  16

<210> SEQ ID NO 24
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(17)
<223> OTHER INFORMATION: any nucleotide

<400> SEQUENCE: 24
ggcggannnn nnnnnnn                                                 17

<210> SEQ ID NO 25
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(17)
<223> OTHER INFORMATION: any nucleotide

<400> SEQUENCE: 25
cagctcnnnn nnnnnnn                                                 17

<210> SEQ ID NO 26
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(15)
<223> OTHER INFORMATION: any nucleotide

<400> SEQUENCE: 26
cacctgcnnn nnnnn                                                   15

<210> SEQ ID NO 27
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: splinker oligonucleotide in Fig. 1A and Fig. 3A

<400> SEQUENCE: 27
gtacgagacg cgcttttgcg cgtctcg                                      27
```

```
<210> SEQ ID NO 28
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1. anchor oligonucleotide in Fig. 1A and Fig.
      3A
<220> FEATURE:
<221> NAME/KEY: misc_feature
<222> LOCATION: (19)..(19)
<223> OTHER INFORMATION: biotinylated nucleotide

<400> SEQUENCE: 28
taccgccgaa gaggcgtttt cgcctcttcg gcg                                  33

<210> SEQ ID NO 29
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 1B, Fig. 1C, Fig. 1D
      and Fig. 3B
<220> FEATURE:
<221> NAME/KEY: misc_feature
<223> OTHER INFORMATION: 5'-end and 3'-end are ligated
<220> FEATURE:
<221> NAME/KEY: misc_feature
<222> LOCATION: (29)..(29)
<223> OTHER INFORMATION: biotinylated nucleotide

<400> SEQUENCE: 29
gcgcgtctcg taccgccgaa gaggcgtttt cgcctcttcg gcggtacgag acgcgctttt     60

<210> SEQ ID NO 30
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: left sequence in Fig. 1E

<400> SEQUENCE: 30
gcggtacgag acgcgctttt gcgcgtctcg tac                                  33

<210> SEQ ID NO 31
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: right sequence in Fig. 1E, Fig. 3C and Fig. 3E
<220> FEATURE:
<221> NAME/KEY: misc_feature
<222> LOCATION: (16)..(16)
<223> OTHER INFORMATION: biotinylated nucleotide

<400> SEQUENCE: 31
cgccgaagag gcgttttcgc ctcttcg                                         27
```

```
<210> SEQ ID NO 32
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: left sequence in Fig. 1F and Fig. 3E
<220> FEATURE:
<221> NAME/KEY: misc_feature
<222> LOCATION: (19)..(19)
<223> OTHER INFORMATION: biotinylated nucleotide

<400> SEQUENCE: 32
cgctatcgaa gaggcgtttt cgcctcttcg ata                              33

<210> SEQ ID NO 33
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: splinker oligonucleotide in Fig. 2A and Fig. 4A

<400> SEQUENCE: 33
cgagacgcgc ttttgcgcgt ctcgt                                       25

<210> SEQ ID NO 34
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1. anchor nucleotide in Fig. 2A and Fig. 4A
<220> FEATURE:
<221> NAME/KEY: misc_feature
<222> LOCATION: (21)..(21)
<223> OTHER INFORMATION: biotinylated nucleotide

<400> SEQUENCE: 34
ccgtcatacg gatacgcgtt ttcgcgtatc cgtatgacgg a                     41

<210> SEQ ID NO 35
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 2B, Fig. 2C, Fig. 2D
      and Fig. 4B
<220> FEATURE:
<221> NAME/KEY: misc_feature
<222> LOCATION: (32)..(32)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 35
gcgcgtctcg tccgtcatac ggatacgcgt tttcgcgtat ccgtatgacg gacgagacgc   60
gcttttt                                                            66
```

```
<210> SEQ ID NO 36
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: left sequence in Fig. 2E, Fig. 2F, Fig. 4C,
      Fig. 4D and Fig. 4E

<400> SEQUENCE: 36
cggacgagac gcgcttttgc gcgtctcgtc cgt                                    33

<210> SEQ ID NO 37
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: right sequence in Fig. 2E, Fig. 4C and Fig. 4D
<220> FEATURE:
<221> NAME/KEY: misc_feature
<222> LOCATION: (17)..(17)
<223> OTHER INFORMATION: biotinylated nucleotide

<400> SEQUENCE: 37
catacggata cgcgttttcg cgtatccgta tga                                    33

<210> SEQ ID NO 38
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2. anchor oligonucleotide in Fig. 2F and Fig.
      4E
<220> FEATURE:
<221> NAME/KEY: misc_feature
<222> LOCATION: (21)..(21)
<223> OTHER INFORMATION: biotinylated nucleotide

<400> SEQUENCE: 38
tactcatacg gatacgcgtt ttcgcgtatc cgtatgagta a                           41

<210> SEQ ID NO 39
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5A (left of text
      "Elongation product #1")
<220> FEATURE:
<221> NAME/KEY: misc_feature
<222> LOCATION: (47)..(47)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 39
gcgcgtctcg tacgcgacgc gtcgtaagcc gtcccgaaga ggcgttttcg cctcttcggg       60
acggcttacg acgcgtcgcg tacgagacgc gctttt                                 96
```

```
<210> SEQ ID NO 40
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5A (left of text
      "Elongation product #2")
<220> FEATURE:
<221> NAME/KEY: misc_feature
<222> LOCATION: (47)..(47)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 40
gcgcgtctcg gtccggccta cgctagatcg atgccgaaga ggcgttttcg cctcttcggc      60
atcgaactag cgtaggccgg accgagacgc gctttt                                96

<210> SEQ ID NO 41
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5B ( left of text "Cut
      elongation product #1 with 3 nucleotide overhang at 5' end") and
      in Fig. 5C (left sequence left of text "Transition  #1")

<400> SEQUENCE: 41
ggacggctta cgacgcgtcg cgtacgagac gcgcttttgc gcgtctcgta cgcgacgcgt      60
cgtaagccg                                                              69

<210> SEQ ID NO 42
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5B (left of text "cut
      elongation product #2 with 3 nucleotide overhang at 5' end") and
      in Fig. 5C (left sequence left of text "Transition #2")

<400> SEQUENCE: 42
gcatcgaact agcgtaggcc ggaccgagac gcgcttttgc gcgtctcggt ccggcctacg      60
ctagatcga                                                              69

<210> SEQ ID NO 43
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5C (right sequence
      left of text "Transition #1")
<220> FEATURE:
<221> NAME/KEY: misc_feature
<222> LOCATION: (16)..(16)
<223> OTHER INFORMATION: biotinylated nucleotide
```

```
<400> SEQUENCE: 43
tcccgagacc gcgttttcgc ggtctcg                                          27

<210> SEQ ID NO 44
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sequence appears in Fig. 5C (right sequence
      left of text "Transition #2")
<220> FEATURE:
<221> NAME/KEY: misc_feature
<222> LOCATION: (16)..(16)
<223> OTHER INFORMATION: biotinylated nucleotide

<400> SEQUENCE: 44
tgccgagacc gcgttttcgc ggtctcg                                          27

<210> SEQ ID NO 45
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5D, Fig. 5E, Fig. 5F
      and Fig. 5G (in each case left of text "Elongation block #1")
<220> FEATURE:
<221> NAME/KEY: misc_feature
<222> LOCATION: (47)..(47)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 45
gcgcgtctcg tacgcgacgc gtcgtaagcc gtcccgagac cgcgttttcg cggtctcggg      60
acggcttacg acgcgtcgcg tacgagacgc gctttt                                96

<210> SEQ ID NO 46
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5D, Fig. 5E, Fig. 5F,
      Fig. 7A (in each case left of text "Elongation block #2") and in
      Fig. 5H (right of text "Elongation block #2")
<220> FEATURE:
<221> NAME/KEY: misc_feature
<222> LOCATION: (47)..(47)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 46
gcgcgtctcg gtccggccta cgctagatcg atgccgagac cgcgttttcg cggtctcggc      60
atcgaactag cgtaggccgg accgagacgc gctttt                                96
```

```
<210> SEQ ID NO 47
<211> LENGTH: 68
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5G (left of text
      "Eco31I cut Elongation block"), Fig. 5I (above text "Cut
      elongation block 1"), Fig. 7B and Fig. 7C (in each case left of
      text "Cut elongation block #1")

<400> SEQUENCE: 47
ggacggctta cgacgcgtcg cgtacgagac gcgcttttgc gcgtctcgta cgcgacgcgt    60
cgtaagcc                                                            68

<210> SEQ ID NO 48
<211> LENGTH: 68
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5H (right of text
      "Elongated transition anchor"), Fig. 5I (right of text "Cut
      elongation block 1"), Fig. 7B (left of text "Cut elongation block
      #2) and Fig. 7D (left of text Cut elongation block #2")
<220> FEATURE:
<221> NAME/KEY: misc_feature
<222> LOCATION: (37)..(37)
<223> OTHER INFORMATION: biotinylated nucleotide

<400> SEQUENCE: 48
gtccggccta cgctagatcg atgccgagac cgcgttttcg cggtctcggc atcgaactag    60
cgtaggcc                                                            68

<210> SEQ ID NO 49
<211> LENGTH: 136
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 5J
<220> FEATURE:
<221> NAME/KEY: misc_feature
<222> LOCATION: (67)..(67)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 49
gcgcgtctcg tacgcgacgc gtcgtaagcc gtccggccta cgctagatcg atgccgagac    60
cgcgttttcg cggtctcggc atcgaactag cgtaggccgg acggcttacg acgcgtcgcg   120
tacgagacgc gctttt                                                  136

<210> SEQ ID NO 50
<211> LENGTH: 106
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: sequence appears in Fig. 6A (left of text
      "Elongation produce #1")
<220> FEATURE:
<221> NAME/KEY: misc_feature
<222> LOCATION: (52)..(52)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 50
gcgcgtctcg tacgcgacgc gtcgataagc cgtctcatac ggatacgcgt tttcgcgtat        60
ccgtatgaga cggcttatcg acgcgtcgcg tacgagacgc gctttt                     106

<210> SEQ ID NO 51
<211> LENGTH: 106
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6A (left of text
      "Elongation product #2)
<220> FEATURE:
<221> NAME/KEY: misc_feature
<222> LOCATION: (52)..(52)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 51
gcgcgtctcg gtccggccta cgctgagatc gatgccatac ggatacgcgt tttcgcgtat        60
ccgtatggca tcgaactcag cgtaggccgg accgagacgc gctttt                     106

<210> SEQ ID NO 52
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6B (left of text "Cut
      elongation product #1 with 3 nucleotide overhang at 5' end") and
      Fig. 6C (left sequence left of text "Transition #1")

<400> SEQUENCE: 52
gacggcttat cgacgcgtcg cgtacgagac gcgcttttgc gcgtctcgta cgcgacgcgt        60
cgataagccg tct                                                          73

<210> SEQ ID NO 53
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6C (left sequence left
      of text "Transition #1")
<220> FEATURE:
<221> NAME/KEY: misc_feature
<222> LOCATION: (13)..(13)
<223> OTHER INFORMATION: biotinylated nucleotide
```

```
<400> SEQUENCE: 53
cgagaccgcg ttttcgcggt ctcga                                              25

<210> SEQ ID NO 54
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6B (left of text "Cut
      elongation product #2 with 3 nucleotide overhang at 5' end") and
      in Fig. C (left of text "Transition #2)

<400> SEQUENCE: 54
catcgaactc agcgtaggcc ggaccgagac gcgcttttgc gcgtctcggt ccggcctacg         60
ctgagatcga tgc                                                           73

<210> SEQ ID NO 55
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6C (right sequence
      left of text "Transition #2")
<220> FEATURE:
<221> NAME/KEY: misc_feature
<222> LOCATION: (13)..(13)
<223> OTHER INFORMATION: biotinylated nucleotide

<400> SEQUENCE: 55
cgagaccgcg ttttcgcggt ctcgg                                              25

<210> SEQ ID NO 56
<211> LENGTH: 98
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6D (left of text
      "Elongation block #1")
<220> FEATURE:
<221> NAME/KEY: misc_feature
<222> LOCATION: (48)..(48)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 56
gcgcgtctcg tacgcgacgc gtcgataagc cgtctcgaga ccgcgttttc gcggtctcga         60
gacggcttat cgacgcgtcg cgtacgagac gcgctttt                                98

<210> SEQ ID NO 57
<211> LENGTH: 98
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 6D (left of text
      "Elongation block #2")
```

```
<220> FEATURE:
<221> NAME/KEY: misc_feature
<222> LOCATION: (48)..(48)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 57
gcgcgtctcg gtccggccta cgctgagatc gatgccgaga ccgcgttttc gcggtctcgg      60
catcgaactc agcgtaggcc ggaccgagac gcgctttt                              98

<210> SEQ ID NO 58
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 7A (left of text
      "Elongation block #1")
<220> FEATURE:
<221> NAME/KEY: misc_feature
<222> LOCATION: (47)..(47)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 58
cgccgtctcg ggacggctta cgacgcgtcg cgtacgagac ccgcttttgc gggtctggta      60
cgcgacgcgt cgtaagccgt cccgagccgg cgtttt                                96

<210> SEQ ID NO 59
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: single-stranded overhang, not complemented by
      complementary strand
<220> FEATURE:
<221> NAME/KEY: misc_feature
<222> LOCATION: (5)..(20)
<223> OTHER INFORMATION: double-stranded nucleid acid, complemented by
      SEQ ID No. 48. The complementary strand continues in its
      5'-direction with an overhang of 4 nucleotides (GCAT)

<400> SEQUENCE: 59
ggacggctta cgacgcgtcg                                                  20

<210> SEQ ID NO 60
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: single-stranded overhang, not complemented by
      complementary strand
```

```
-continued
<220> FEATURE:
<221> NAME/KEY: misc_feature
<222> LOCATION: (1)..(4)
<223> OTHER INFORMATION: double-stranded nucleid acid, complemented by
      SEQ ID No. 47. The complementary strand continues in its
      5'-direction with an overhang of 4 nucleotides (CAGG)

<400> SEQUENCE: 60
tacgcgacgc gtcgtaagcc                                              20

<210> SEQ ID NO 61
<211> LENGTH: 108
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence appears in Fig. 7D (right of text
      "Complementary overhang for subsequent transposition step")
<220> FEATURE:
<221> NAME/KEY: misc_feature
<222> LOCATION: (57)..(57)
<223> OTHER INFORMATION: biotinylated nucleotide
<220> FEATURE:
<221> NAME/KEY: misc_feature
<223> OTHER INFORMATION: 5'-end and 3'-end are ligated

<400> SEQUENCE: 61
tacgcgacgc gtcgtaagcc gtccggccta cgctagatcg atgccgagac cgcgttttcg    60
cggtctcggc atcgaactag cgtaggccgg acggcttacg acgcgtcg               108
```

METHOD FOR THE MANUFACTURE OF NUCLEIC ACID MOLECULES

This application is a 371 of PCT/EP2003/01551 filed on 17 Oct. 2003 which claims priority from EP 02023385.4 filed on 18 Oct. 2002.

The present invention is related to methods for the manufacture of a nucleic acid molecule and compounds used therefore.

Nucleic acids are used in many different ways in modern biotechnology. Apart from comparatively small nucleic acid molecules such as oligonucleotides, nucleic acid molecules of several kilo bases are made available using different methods of manufacture. Typically, for the synthesis of the latter kind of nucleic acid molecules a number of synthetic oligonucleotides having a length of 40 to 100 nucleotides are used as basic modules and joined together. These oligonucleotide building blocks comprise a number of termination products as well as defect sequences despite comparatively high coupling rates of about 98 to 99% per step. Especially problematic are n–1 products (oligonucleotides containing internal one nucleotide deletions), which occur as a result of incomplete capping reactions. Since many oligonucleotides have to be assembled in order to generate a complete gene, the probability of creating an error-free product is extremely low for all known synthesis procedures. Such defective synthesis products are particularly disadvantageous if the nucleic acid molecule to be synthesised represents a coding sequence and thus shortened transcription or translation products are generated due to a frame shift of the open reading frame. It is therefore necessary to purify the oligonucleotide components as otherwise complex gene synthesis would factually be impossible.

In the prior art methods are known such as the so-called "gap filling" method. According to this method a variety of partially overlapping oligonucleotides are synthesised, purified and subsequently hybridised as pairs or in subgroups. After the synthesis of the respective opposite strands using a DNA polymerase the individual fragments are ligated to each other. The double stranded ligation product generated in this way may be either cloned as partial fragments or hybridised with terminal oligonucleotide primers and subsequently amplified in a polymerase chain reaction (PCR). Alternatively, complementary oligonucleotides may be hybridised to each other and the thus obtained gene fragments ligated by either enzymatic or chemical ligation. After purification and/or cloning these gene fragments may be joined together. Both methods are of limited use as with increasing length of the nucleic acid molecule to be synthesised the probability increases that one or several oligonucleotides with an incorrect sequence will be incorporated into the final product. Such errors are then copied by the DNA polymerase. In addition, sequence errors may also be introduced during the PCR reaction.

International patent application WO 99/47536 discloses a method of using solid phase synthesis to link different oligonucleotides such as to generate longer nucleic acid molecules. More particularly, WO 99/47536 discloses a method where single-stranded oligonucleotides are sequentially ligated to an immobilised starter molecule in a defined orientation. A disadvantage of this method is that a large number of single steps is required for the synthesis of larger genes resulting in reduced yield and enrichment of defective sequences. Also, this method is difficult to automate which is a prerequisite for a rapid, standardised synthesis.

International patent application WO 00/75364 discloses a combinatorial solid phase synthesis of nucleic acids using a library of double-stranded oligonucleotides as standardised building blocks. The use of standardised building blocks makes it unnecessary to synthesize a new set of oligos for each new synthesis. These double-stranded library oligonucleotides generally share an identical overall structure. In one preferred version, they contain a terminal loop, a double-stranded stem and a short single-stranded overhang. There are two different classes of library oligonucleotides, which are characterized by the presence of different recognition sites for type IIS restriction enzymes within their sequence and the presence or absence or the type of an internal modification. The nucleotides in the overhang and the directly adjacent region form the variable portion that actually contributes to the nucleic acid to be synthesized; the remaining sequence is generally identical in all oligonucleotides belonging to the same class.

To build up a double-stranded nucleic acid, its sequence is first broken down into smaller fragments (usually about 20 base pairs each). These so-called elongation blocks are then synthesized in parallel reactions. In one such reaction, two double-stranded library oligonucleotides, one of each class, are ligated via matching single-stranded overhangs. The ligation products thereof are subsequently cleaved by the type IIS restriction enzyme, which is specific for the oligonucleotide that donates nucleotides. The net effect of such a ligation/restriction cycle is the addition of a small number of base pairs, typically between one to five, to the starting oligonucleotides. This process is then repeated until the synthesis of the desired elongation block is completed.

In a second reaction phase, the so-called transposition, those elongation blocks that are adjacent in the nucleic acid to be synthesized are ligated in a pairwise fashion after each block has been cleaved with a different type IIS restriction enzyme. By repeating this procedure several times the length of the transposition intermediates doubles in each step whereas the number of reactions is cut in half. Thus a defined nucleic acid molecule can be generated in very few cycles. The advantage of this method resides in the combinatorial pairwise assembly of the fragments of the nucleic acid molecule to be synthesised, in a sequence independent manner. Any desired elongation block may thus be generated from a standardised nucleic acid library with a defined number of elements.

The number of the elements of such a library depends on the length of the overhangs generated by the individual type IIS restriction enzyme as well as the number of nucleotides that are added to the growing oligonucleotides in each elongation cycle.

Although this method is suitable to automation, and as such allows a proper synthesis of large nucleic acid molecules, there is a need in the art to further improve this method to generate fewer side products. Due to incomplete restriction enzyme cleavage of the ligated intermediates, side products missing one or several of the nucleotide blocks added in each step may be formed, which are able to ligate in the subsequent transposition reactions. Such side products lead to the formation of incomplete transposition blocks and reduce the yield of the correct product.

According to the present invention this problem is solved in a first aspect by a method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang, c) ligating the first and the second oligonucleotide via their overhangs generating a first ligation product, d) immobilising the first ligation product to the surface via the modification, e) cutting the immobilised ligation product with the first type IIS restriction enzyme thus releasing an elongated oligonucleotide having an overhang, f) combining the elongated oligonucleotide with a further at least partially double-stranded oligonucleotide which has a modification allowing the oligonucleotide to be coupled, to a surface, whereby the further oligonucleotide comprises a recognition site for a further type IIS restriction enzyme which cuts outside its recognition site and which oligonucleotide comprises a single-stranded overhang, and ligating the elongated second oligonucleotide and the further at least partially double-stranded oligonucleotide via their overhangs forming a further ligation product, g) immobilising the further ligation product to a surface via the modification, h) cutting the further ligation product with the further type IIS restriction enzyme releasing an elongated oligonucleotide having an overhang, and i) optionally, repeating steps f) to h).

According to the present invention this problem is solved in a second aspect by a method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) immobilising the first oligonucleotide to the surface via the modification, c) providing a second at least partially double-stranded oligonucleotide whereby the oligonucleotide comprises a recognition site or a part thereof for a second type IIS restriction enzyme which cuts outside its recognition site, and which second oligonucleotide comprises a single-stranded overhang, d) ligating the first and the second oligonucleotide via their overhangs generating a first ligation product, e) cutting the immobilised ligation product with the first type IIS restriction enzyme thus releasing an elongated oligonucleotide having an overhang, f) providing a further at least partially double-stranded oligonucleotide which has a modification allowing the oligonucleotide to be specifically coupled to a surface, whereby the oligonucleotide contains a recognition site for a further type IIS restriction enzyme and a single-stranded overhang, g) immobilising the further at least partially double-stranded oligonucleotide on a surface via its modification, h) combining the elongated oligonucleotide with the immobilised further oligonucleotide, and ligating them via their overhangs forming a further ligation product, i) cutting the resulting further ligation product with the further type IIS restriction enzyme releasing an elongated oligonucleotide having an overhang, and j) optionally, repeating steps f) to i).

According to the present invention this problem is solved in a third aspect by a method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang, c) ligating the first and the second oligonucleotide via their overhangs generating a first ligation product, d) cutting the ligation product with the first type IIS restriction enzyme thus generating an elongated oligonucleotide having an overhang and a shortened first oligonucleotide, e) immobilising the shortened first oligonucleotide on a surface via the modification, f) providing a further at least partially double-stranded oligonucleotide which has a modification allowing the further oligonucleotide to be coupled to a surface, whereby the further oligonucleotide comprises a recognition site for a further type IIS restriction enzyme which cuts outside its recognition site and which oligonucleotide comprises a single-stranded overhang.

g) combining the elongated oligonucleotide with the further oligonucleotide and ligating the elongated oligonucleotide and the further oligonucleotide via their overhangs forming a further ligation product, h) cutting the further ligation product with the further type IIS restriction enzyme generating an elongated oligonucleotide having an overhang and a shortened further oligonucleotide, and i) optionally, repeating steps e) to h).

In an embodiment of the methods according to the present invention the overhang is a 5'-overhang or a 3'-overhang.

In a further embodiment of the methods according to the present invention the overhang is selected from the group comprising a one nucleotide overhang, a two nucleotides overhang, a three nucleotides overhang, a four nucleotides overhang, a five nucleotides overhang, a six nucleotides overhang and a seven nucleotides overhang.

In a still further embodiment of the methods according to the present invention the elongated oligonucleotide is transferred to a new reaction vessel where it is combined with the further oligonucleotide.

In a preferred embodiment of the methods according to the present invention the at least partially double-stranded oligonucleotide comprises a constant region and a variable region whereby the constant region contains a recognition site for a type IIS restriction enzyme, and the variable region contains a nucleic acid sequence which corresponds to a part of the nucleic acid sequence of the nucleic acid molecule to be manufactured.

According to the present invention this problem is solved in a fourth aspect by a method for the synthesis of a nucleic acid molecule comprising the following steps:

a) Providing a first ligated elongated oligonucleotide by
  i) providing a first elongated oligonucleotide, whereby the first elongated oligonucleotide is preferably the elongated oligonucleotide according to the method of the first, second and/or third aspect of the present invention;
  ii) providing a second elongated oligonucleotide, whereby the second elongated oligonucleotide is preferably generated starting from the further ligation product according to the method of any of the first, second and/or third aspect of the present invention by cutting the further ligation product by the second type IIS restriction enzyme;
  iii) ligating the first and the second elongated oligonucleotide, whereby either the first and the second elongated oligonucleotides are ligated in solution and are subsequently immobilized to a surface by means of the modification, or the second elongated oligonucleotide is immobilized to a surface by means of the modification and subsequently the first elongated oligonucleotide is ligated thereto generating in both cases a first ligated elongated oligonucleotide,
b) providing a second ligated elongated oligonucleotide by
  i) providing a third elongated oligonucleotide, whereby the third elongated oligonucleotide is the elongated oligonucleotide according to the method of the first, second and/or third aspect of the present invention;
  ii) providing a fourth elongated oligonucleotide, whereby the fourth elongated oligonucleotide is generated starting from the further ligation product according to the method of the first, second and/or third aspect of the present invention by cutting the further ligation product by the second type IIS restriction enzyme:
  iii) ligating the third and the fourth elongated oligonucleotide, whereby either the third and the fourth elongated oligonucleotides are ligated in solution and subsequently immobilized to a surface by means of the modification, or the fourth elongated oligonucleotide is immobilized to a surface by means of the modification and subsequently the third elongated oligonucleotide is ligated thereto generating in both cases a second ligated elongated oligonucleotide,
c) cutting the first ligated elongated oligonucleotide by a type IIS restriction enzyme, whereby the restriction enzyme is the first type IIS restriction enzyme, generating a first cut ligated elongated oligonucleotide;
d) cutting the second ligated elongated oligonucleotide by a type IIS restriction enzyme, whereby the restriction enzyme is the second type IIS restriction enzyme, generating a second cut ligated elongated oligonucleotide;
e) combining and ligating the first cut ligated elongated oligonucleotide and the second cut ligated elongated oligonucleotide;
f) optionally repeating steps a) to e), whereby the ligation product of step e) is used as a first ligated elongated oligonucleotide and/or as a second ligated elongated oligonucleotide.

According to the present invention this problem is solved in a fifth aspect by a method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, and whereby the oligonucleotide comprises a part of the nucleic acid molecule to be manufactured,
b) immobilizing the first oligonucleotide on a surface
c) cutting the first oligonucleotide with the first type IIS restriction enzyme releasing a double stranded oligonucleotide having a single stranded overhang at each end and being a part of the nucleic acid molecule to be manufactured,
d) combining the double stranded oligonucleotide of step c) with a second at least partially double-stranded oligonucleotide which has a modification allowing the oligonucleotide to be coupled to a surface, whereby the oligonucleotide contains a recognition site for a second type IIS restriction enzyme which cuts outside its recognition site, and which oligonucleotide further comprises a single-stranded overhang and a part of the nucleic acid molecule to be manufactured, and ligating the double-stranded oligonucleotide of step c) with the second oligonucleotide;
whereby the overhang of the second oligonucleotide is essentially complementary to the overhang of the double stranded oligonucleotide of step c).

In an embodiment thereof the overhang generated upon cutting the first oligonucleotide with the first type IIS restriction enzyme is essentially complementary to the overhang of the second at least partially double stranded oligonucleotide.

According to the present invention this problem is solved in a sixth aspect by a method for the manufacture of a nucleic acid molecule comprising the following steps:

a) providing a first ligation product, whereby the first ligation product consists of a first oligonucleotide moiety comprising a recognition site for a first type IIS restriction enzyme, a second oligonucleotide moiety comprising a recognition site for a second type IIS restriction enzyme and a third oligonucleotide moiety, whereby the third oligonucleotid moiety is a part of the nucleic acid molecule to be manufactured, and whereby the first and the second type IIS restriction enzymes each generate an overhang, whereby the overhang generated by the first type IIS restriction enzyme has a length which is different from the length of the overhang generated by the second type IIS restriction enzyme;
b) providing a second ligation product, whereby the second ligation product consists of a first oligonucleotide moiety comprising a recognition site for a third type IIS restriction enzyme, a second oligonucleotide moiety comprising a recognition site for a fourth type IIS restriction enzyme and a third oligonucleotide moiety, whereby the third oligonucleotide moiety is a part of the nucleic acid molecule to be manufactured, and whereby the third and the fourth type IIS restriction enzyme each generate an overhang, whereby the overhang generated by the third type IIS restriction enzyme has a length which is different from the length of the overhang generated by the fourth type IIS restriction enzyme;
c) cutting the first ligation product with the second restriction enzyme generating a first cut ligation product and cutting the second ligation product with the fourth restriction enzyme generating a second cut ligation product;

d) providing a third at least partially double-stranded oligonucleotide and ligating the third oligonucleotide with the first cut ligation product, whereby the third oligonucleotide comprises an overhang which is complementary to the overhang of the first cut ligation product generated in step c) and whereby the third oligonucleotide comprises a recognition site for a fifth IIS restriction enzyme;

e) providing a fourth at least partially double-stranded oligonucleotide and ligating the fourth oligonucleotide to the second cut ligation product, whereby the fourth oligonucleotide comprises an overhang which is complementary to the overhang of the second ligation product generated in step c) and whereby the fourth oligonucleotide comprises a recognition site for a sixth type IIS restriction enzyme;

f) optionally immobilising the ligation product of step d) and step e) on a surface by means of a modification of the third oligonucleotide and the fourth oligonucleotide;

g) cutting the immobilised ligation product of step d) with the fifth type IIS restriction enzyme releasing an oligonucleotide;

h) cutting the immobilised ligation product of step e) with the third type IIS restriction enzyme; and i) combining and ligating the oligonucleotide released according to step g) with the immobilised reaction product of step h), whereby the overhang generated by the first and the third restriction enzyme is complementary to the overhang generated by the fifth and sixth restriction enzyme.

In an embodiment thereof the first and the third restriction enzyme are identical and/or the second and the fourth restriction enzyme are identical and/or the fifth and the sixth restriction enzyme are identical.

In a further embodiment of this method the first and the third restriction enzyme and the fifth and the sixth restriction enzyme are each a restriction enzyme generating a four nucleotide overhang, preferably at the 5' end.

In a still further embodiment of this method the second and the third restriction enzyme is a restriction enzyme creating an overhang having a length which is selected from the group comprising 1, 2, 3, 4, 5 and 6 nucleotides.

In a preferred embodiment of this method the first and the second restriction enzyme is Esp3I or Eco31I and the fifth and the sixth restriction enzyme is Ecp31I or Esp3I.

In a preferred embodiment of this method the ligation product of step i) is used as a first ligation product and/or a second ligation product and steps a) to i) are repeated one or several times.

In a further embodiment of this method the third moiety is arranged between the moieties of the oligonucleotides containing the restriction site for the type IIS restriction enzymes.

In a preferred embodiment of this method the first and the second ligation products are provided in separate reaction vessels.

According to the present invention this problem is solved in a seventh aspect by a method for the manufacture of a nucleic acid molecule comprising the following steps:

a) Providing a first ligation product, whereby the first ligation product consists of a first oligonucleotide moiety comprising a recognition site for a first type IIS restriction enzyme, a second oligonucleotide moiety comprising a recognition site for a second type IIS restriction enzyme and a third oligonucleotide moiety, and immobilising the first ligation product via a modification to a surface, whereby the modification is incorporated by the second moiety, b) providing a second ligation product, whereby the second ligation product consists of a first oligonucleotide moiety comprising a recognition site for a first type IIS restriction enzyme, a second oligonucleotide moiety comprising a recognition site for a second type IIS restriction enzyme and a third oligonucleotide moiety, and immobilising the second ligation product via a modification to a surface, whereby the modification is incorporated by the second moiety, c) cutting the first ligation product with the restriction enzyme the recognition site of which is contained in the first moiety providing a cut immobilised first ligation product, d) cutting the second ligation product with the restriction enzyme the recognition site of which is contained in the first moiety providing a cut immobilised first ligation product, e) cutting the cut immobilised first ligation product with the restriction enzyme the recognition site of which is contained in the second oligonucleotide moiety releasing a double-stranded DNA fragment, f) combining and ligating the double-stranded DNA fragment with the cut immobilised second ligation product.

In an embodiment of this method the ligation product of step f) is combined and ligated with an elongated oligonucleotide according to any of the preceding claims, whereby this ligation product is used as a first or a second ligation product in step a) or step b) in the method according to the seventh aspect of the present invention.

In a preferred embodiment of this method the DNA fragment is the nucleic acid molecule or part thereof which is to be manufactured.

In a more preferred embodiment of this method the third moiety is arranged between the moieties of the oligonucleotides containing the restriction site for the type IIS restriction enzymes.

The inventive method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang, c) ligating the first and the second oligonucleotide via their overhangs generating a first ligation product, d) immobilising the first ligation product to the surface via the modification, e) cutting the immobilised ligation product with the first type IIS restriction enzyme thus releasing an elongated oligonucleotide having an overhang, f) combining the elongated oligonucleotide with a further at least partially double-stranded oligonucleotide which has a modification allowing the oligonucleotide to be coupled to a surface, whereby the further oligonucleotide comprises a recognition site for a further type IIS restriction enzyme which cuts outside its recognition site and which oligonucleotide comprises a single-stranded overhang, and ligating the elongated second oligonucleotide and the further at least partially double-stranded oligonucleotide via their overhangs forming a further ligation product, g) immobilising the further ligation product to a surface via the modification, h) cutting the further ligation product with the further type IIS restriction enzyme releasing an elongated oligonucleotide having an overhang, and i) optionally, repeating steps f) to h), is also referred to herein as reverse solid phase synthesis (RSPS).

As may be taken from the sequence of steps of the RSPS method, the first and the further oligonucleotide act as donor molecules whereas the second oligonucleotide and the elongated oligonucleotide act as acceptor molecules. It is to be understood that the elongated oligonucleotide is functionally the same as the second oligonucleotide in the second round or cycle of the method. As a matter of fact, the elongated oligonucleotide comprises the second oligonucleotide and those nucleotides transferred thereto from the first oligonucleotide and the further oligonucleotide, respectively, in subsequent rounds or cycles of the method.

It is a characteristic of the inventive RSPS method that the elongated oligonucleotide is transferred from the reaction, preferably from the reaction vessel, in which it was generated, to a different reaction, preferably to a different reaction vessel leaving the other reaction products which might interfere with the subsequent reactions, in the earlier reaction vessel. This can be achieved by the first and further oligonucleotides having a modification which allows immobilisation to a surface such as the surface of a reaction vessel, e.g. the well of a multi-well plate. This modification allows for a specific immobilisation of the oligonucleotide rather than an immobilisation through the nucleotides or reactive groups thereof forming the oligonucleotide. Once the ligation products from the ligation of the first and the second oligonucleotide, and of the further oligonucleotide and the elongated oligonucleotide, respectively, are cleaved by the type IIS restriction enzyme the recognition site of which is contained in the first and the further at least partially double-stranded oligonucleotide, respectively, the elongated oligonucleotides are released whereas the shortened first and shortened further oligonucleotides remain immobilised on the surface. The shortened first and shortened further oligonucleotides correspond to the first and further oligonucleotide, respectively, except that they lack that part of the respective oligonucleotides which was extending beyond the cleavage site of the first and the further type IIS restriction enzyme prior to cleavage. Besides the shortened first and shortened further oligonucleotides also the non-cleaved ligation products, non-ligated first oligonucleotides and non-ligated further oligonucleotides remain immobilised and thus retained in the earlier reaction and more particularly in the earlier reaction vessel.

As used in any of the methods according to the present invention, the oligonucleotides exhibiting a single-stranded overhang are ligated to other oligonucleotides having an overhang on the basis of base complementarity. Preferably, the base complementarity is complete, i.e. any of the base pairs are perfectly base-pairing according to Watson-Crick-Base-Pairing Rules. However, it is also within the present invention that the hybridised single-stranded overhangs of the two respective oligonucleotides contain at least one mismatched base pair. The number of mismatches allowable depends on the reaction conditions such as salt concentration and temperature and can be determined by routine testing by the ones skilled in the art.

In a further aspect a derivative of the aforementioned RSPS method is provided. Said method for the manufacture of a nucleic acid molecule comprises the steps of a) providing a first at least partially double-stranded oligonucleotide which comprises a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) immobilising the first oligonucleotide to the surface via the modification, c) providing a second at least partially double-stranded oligonucleotide whereby the oligonucleotide comprises a recognition site or a part thereof for a second type IIS restriction enzyme which cuts outside its recognition site, and which second oligonucleotide comprises a single-stranded overhang which preferably is complementary to the single-stranded overhang of the first oligonucleotide, d) ligating the first and the second oligonucleotide via their overhangs generating a first ligation product, e) cutting the immobilised ligation product with the first type IIS restriction enzyme thus releasing an elongated oligonucleotide having an overhang, h) providing a further at least partially double-stranded oligonucleotide which comprises a modification allowing the oligonucleotide to be specifically coupled to a surface, whereby the oligonucleotide contains a recognition site for a first or further type IIS restriction enzyme and a single-stranded overhang which preferably is complementary to the overhang of the elongated oligonucleotide, i) immobilising the further at least partially double-stranded oligonucleotide on a surface via its modification h) combining the elongated oligonucleotide with the immobilised further oligonucleotide, and ligating them via their overhangs forming a further ligation product, i) cutting the resulting further ligation product with the further type IIS restriction enzyme releasing an elongated oligonucleotide having an overhang, and j) optionally, repeating steps f) to i).

A particular advantage of both variants of this method compared to the method published in WO 00/75364 is the almost complete removal of side products that arise as a consequence of incomplete cleavages. In the above-cited procedure these shortened intermediates compete for ligation with the correct elongation blocks in the subsequent transpositions where pairs of elongation blocks are assembled in several steps to generate the nucleic acid to be manufactured. The RSPS variant has the further advantage that a buffer change between the binding and the ligation step is possible, which allows the ligation reaction to take place under optimal buffer conditions. Despite a reduced ligation efficiency is observed with immobilised substrates, the overall yield of elongated intermediate after one cycle is higher with the RSPS variant. This is probably due to the fact that the ligation products formed are already attached to the solid phase and do not have to compete with the abundant first and further oligonucleotides for binding to the surface. As the yield of the intermediate product decreases in each cycle (because both ligation and restriction reactions practically never reach completion), the incoming further oligonucleotides are in excess, thus hampering the binding of the ligation products. Furthermore, since the first and further oligonucleotides are smaller than the ligation products, their binding to the surface is favored. In the second and later steps, one can simply reduce the concentration of the incoming further oligonucleotides so that the binding capacity of the solid phase exceeds the amount of available modified oligonucleotides. However, this is not feasible in the first cycle because one wants to operate at the limits of the binding capacity in order to maximize the yield of the reactions.

In one subvariant of the above described RSPS procedure, the ligation of the first and further oligonucleotides with the second or elongated oligonucleotide is carried out after the immobilisation of the first and further oligonucleotide, i.e. reversing the order of steps c) and d). Although the ligation efficiency of immobilised substrates is lower than in solution, the ligation products do not have to compete with the abundant first or further oligonucleotide for binding to the surface.

The further inventive method for the manufacture of a nucleic acid molecule comprising the steps of a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang, c) ligating the first and the second oligonucleotide via their overhangs generating a first ligation product, d) cutting the ligation product with the first type IIS restriction enzyme thus generating an elongated oligonucleotide having an overhang and a shortened first oligonucleotide, e) immobilising the shortened first oligonucleotide on a surface via the modification, f) providing a further at least partially double-stranded oligonucleotide which has a modification allowing the further oligonucleotide to be coupled to a surface, whereby the further oligonucleotide comprises a recognition site for a further type IIS restriction enzyme which cuts outside its recognition site and which oligonucleotide comprises a single-stranded overhang.

g) combining the elongated oligonucleotide with the further oligonucleotide and ligating the elongated oligonucleotide and the further oligonucleotide via their overhangs forming a further ligation product, h) cutting the further ligation product with the further type IIS restriction enzyme generating an elongated oligonucleotide having an overhang and a shortened further oligonucleotide, and i) optionally, repeating steps e) to h)

is also referred to herein as the RLPS method. As may be taken from the sequence of steps of the RLPS method, this method is very similar to the RSPS method disclosed herein. Again, the elongated oligonucleotide is transferred, preferably from the first reaction to a second, i.e. subsequent, reaction whereby even more preferably the second reaction is carried out in a reaction vessel which is different from the reaction vessel where the first reaction was carried out. The difference between the RLPS and the RSPS method resides in changing the order of ligation, cleavage by the type IIS restriction enzyme and immobilisation. According to the RLPS method, the ligation product is subject to cleavage by the type IIS restriction enzyme the recognition site of which is contained in the first and further at least partially double-stranded oligonucleotide, immediately after the ligation and prior to the immobilisation step. This means that the type IIS restriction enzyme cleaves the non-immobilised ligation products of the first and second at least partially double-stranded oligonucleotide and the further and elongated oligonucleotide, respectively, and that the shortened first oligonucleotide and the shortened further oligonucleotides are immobilised. In addition to the latter oligonucleotides, any of the other side products of the sequence of steps as described in connection with the RSPS method are removed or kept away from subsequent reactions.

The present inventors have surprisingly discovered that the particular sequence of reaction steps of the RSPS and the RLPS method results in a reduction of the variety and number of undesired by-products, thus increasing the efficacy of the inventive method for the synthesis of the nucleic acid molecule to be manufactured. This particular sequence is in contrast to the otherwise in many regards very similar method for the manufacture of nucleic acid molecules as described in WO 00/75368 which is known and herein referred to as the Sloning method. According to the original Sloning method, the elongated oligonucleotide remains immobilised to a surface, and the donor oligonucleotides are added in the liquid phase of the reaction.

The reason for this improved performance is that the ligation between the first and the second oligonucleotide and the further oligonucleotide and the elongated oligonucleotide in subsequent rounds of the inventive methods shows a higher yield when both oligonucleotides are kept in solution rather than one of them being attached to a surface. Additionally, the reaction kinetics can be better controlled as molarity of the reaction compounds would be changed in subsequent steps by transferring the by-products described above. Typically, the oligonucleotide that provides a part of the nucleic acid molecule to be manufactured by the inventive method, the donor oligonucleotides, i.e. the first oligonucleotide and the further oligonucleotides are present in a new reaction vessel such as a well of a multi-well plate. The reason for this is that by doing so neither the uncleaved ligation product nor the uncleaved donor oligonucleotide which remain immobilised via their modification to a surface, are transferred to a new ligation reaction. This would otherwise result in false ligation products. However, the ligation should occur only between the elongated oligonucleotide and the further at least double-stranded oligonucleotide, which serves again as a donor molecule and provides a further part of the nucleic acid molecule to be manufactured. In addition, the immobilisation step allows that all of the components of the reaction are removed which may be troublesome in subsequent steps.

Libraries for Different Elongation Procedures

It is essential for the present invention that at least two different type IIS restriction enzymes are used. Basically, the inventive methods work with any type IIS restriction enzymes. Preferably, those type IIS restriction enzymes are used which provide a three nucleotide long overhang at the 5' end such as SapI, Eam1104I and the respective isoschizomers EarI, Ksp632I, or those type IIS restriction enzymes which provide a one nucleotide overhang at the 3' end such as BfiI, BmrI, BfuI, BciVI, BspPI, AclWI, AlwI, PleI, MlyI, PpsI.

The at least partially double-stranded oligonucleotides as used in the inventive methods have preferably a common basic design. This means that libraries of standardised building blocks can be generated which represent the at least partially double-stranded oligonucleotides as used in connection with the inventive methods. The members of the libraries differ from each other only in those terminal nucleotides that will form part of the nucleic acid molecule to be manufactured using the inventive methods and the respective oligonucleotides. The library oligonucleotides usually consist of one consecutive string of nucleotides that can fold back on themselves to form a double-strand with an internal loop. Alternatively, they may consist of two strands, namely an upper and a lower strand which are hybridised but not otherwise linked to each other. In the latter case, the upper strand has a blocked 5' terminal nucleotide, whereas the lower strand has a blocked 3' terminal nucleotide. The upper strand and the lower strand are at least partially complementary to each other and form at least partially a double-stranded structure or duplex. Either the 3' end of the upper strand or the 5' end of the lower strand is protruding relative to the 5' end of the lower strand or to the 3'end of the upper strand. The first alternative is also referred to herein 3' overhang, and the second alternative is also referred to herein as 5' overhang. The length of the overhang may be as little as one nucleotide. The length of the overhang may thus be one, two, three, four, five, six, seven or more nucleotides. Any reference to the 5' end and 3' end, respectively, is made under the assumption that both sequence annotation and synthesis direction is from the left side to the right side.

The at least partially double-stranded oligonucleotide may be either formed by the folding of a self-complementary single strand generating a loop connecting the upper and the lower strand of the duplex (a uni-partite at least partially double-stranded oligonucleotide), or by annealing the upper and the lower strand (a bi-partite at least partially double-stranded oligonucleotide). The design of the at least partially double-stranded oligonucleotide should be such that it preferably meets the following two requirements. First, the melting temperature of the double-stranded region must be high enough to avoid a denaturation of the double-stranded structure under the conditions realised in the synthesis or the manufacturing process Second, the at least partially double-stranded oligonucleotide has to have an orientation which allows for a defined ligation with other oligonucleotide molecules having a complementary overhang themselves. Such orientation is created by blocking the end of the at least partially double-stranded oligonucleotide that is different from the end defined by the protruding 3' end of the upper strand and the protruding 5' end of the lower strand, respectively. Accordingly, the end to be blocked is defined by the 5' end of the upper strand and the 3' end of the lower strand. Such blocking may be either realised by the loop structure or by any other suitable modifications known to the one skilled in the art. Possible suitable modifications may result from the incorporation of low molecular weight compounds to the at least partially double-stranded oligonucleotide whereby, preferably, biotin, digoxygenin, fluoresceine thiocyanate (FITC), amino compounds or succinyl esters may be used. Examples for both uni-partite as well as bi-partite at least partially double-stranded oligonucleotides may be taken from WO 00/75368). If not mentioned to the contrary the term oligonucleotide as used herein may also mean at least partially double-stranded oligonucleotide.

In addition, the at least partially double-stranded oligonucleotides comprise a recognition site and a cleavage site for a type IIS restriction enzyme. Type IIS restriction enzymes are characterised by the fact that they interact with two discrete sites of a double-stranded DNA. One of said sites is the recognition site for said restriction enzyme which typically has a length of four to seven base pairs. The other site is the cleavage site which is typically one to twenty base pairs apart from the recognition site. The recognition sites of the restriction enzymes are either completely or partially asymmetric. As used herein, the double-stranded oligonucleotides comprise the recognition site for the type IIS restriction enzyme which may be either completely or partially part of the single-stranded part or of the double-stranded part of the oligonucleotide. To allow for the proper functioning of the method according to the present invention, the type IIS restriction enzyme the recognition site of which is contained in the first and further at least partially double-stranded oligonucleotide, respectively, and which is also referred to herein as the first and further type IIS restriction enzyme, respectively, and the type IIS restriction enzyme the recognition site of which is contained in the second at least partially double-stranded oligonucleotide and which is also referred to herein as the second type IIS restriction enzyme, must be different. The same applies to the second restriction enzyme and the further restriction enzyme.

The following table provides some possible combinations of recognition sequences of type IIS restriction enzymes.

| Recognition site for first oligonucleotide | Recognition site for second oligonucleotide |
|---|---|
| CGTCTCN^NNNN_(Esp3I, BsmBI) (SEQ.ID.No.1) | GGTCTCN^NNNN_(BsaI, Eco31I . . .) |
| GGTCTCN^NNNN_(BsaI, Eco31I, . . .) (SEQ.ID.No.2) | CGTCTCN^NNNN_(Esp3I, BsmBI) |
| GAAGACNN^NNNN_(BbsI, BpiI . . .) (SEQ.ID.No.3) | ACCTGCNNNN^NNNN_(BSpMI, Acc36I) |
| ACCTGCNNNN^NNNN_(BSpMI, Acc36I) (SEQ.ID.No.4) | GAAGACNN^NNNN_(BbsI, BpiI . . .) |
| GCAGTG_NN^ (BtsI) (SEQ.ID.No.5) | GCAATG_NN^ (BsrDI, Bse3DI, . . .) |
| GCAATG_NN^ (BsrDI, Bse3DI, . . .) (SEQ.ID.No.6) | GCAGTG_NN^ (BtsI) |

-continued

| Recognition site for first oligonucleotide | Recognition site for second oligonucleotide |
|---|---|
| GTATCCNNNNN_N^ (BciVI, BfuI)<br>(SEQ.ID.No.7) | ACTGGGNNNN_N^ (BfiI, BmrI) |
| ACTGGGNNNN_N^ (BfiI, BmrI)<br>(SEQ.ID.No.8) | GTATCCNNNNN_N^ (BciVI, BfuI) |
| GGCGGANNNNNNNNN_NN^ (EciI)<br>(SEQ.ID.No.9) | GAGGAGNNNNNNNN_NN^ (BseRI) |
| GAGGAGNNNNNNNN_NN^ (BseRI)<br>(SEQ.ID.No.10) | GGCGGANNNNNNNNN_NN^ (EciI) |
| CACCTGCNNNN^NNNN_(AarI)<br>(SEQ.ID.No.11) | CAGCTCNNNNNNN^NNNN_(AceIII) |
| CAGCTCNNNNNNN^NNNN_(AceIII)<br>(SEQ.ID.No.12) | CACCTGCNNNN^NNNN_(AarI) |
| GCTCTTCN^NNN_(SapI)<br>(SEQ.ID.No.13) | - (adapter linker necessary) |
| CTCTTCN^NNN_(Eam1104I, Ksp632I, EarI)<br>(SEQ.ID.No.14) | - (adapter linker necessary) | whereby
N = any of the nucleotides A, G, C or T;
^ist the cleavage site in the upper strand, i. e. 5'->3' from left to right, and
_the cleavage site in the lower strand, i. e. 5'->3' from right to left.

Preferred combinations of the first (and further) and second type IIS restriction enzyme to be used in connection with the present invention are Eco31I/Esp3I (37° C.), BsaI/BsmBI (50° C.), BsmBI/BsaI (55° C.), BbsI/BspMI (37° C.), BspMI/BbsI (37° C.) BsrDI/BtsI (65° C.), BtsI/BsrDI (37° C.), BciVI/Bmrl (37° C.), AarI/AceIII (37° C.), EciI/BseRI (37° C.) und BmrI/BciVI (37° C.). Temperatures in brackets indicate the incubation temperatures used for each of the pairs. The isoschizomers of these enzymes (BsaI: Bso31, Eco31I; BsmBI: Esp3I; BbsI: BpiI, BpuAI; BspMI: Acc36I; BsrDI: Bse3DI, BseMI; BmrI: BfiI) are potential alternatives.

Design of the Library Oligonucleotides

In addition to the aforementioned features, the first and second at least partially double-stranded oligonucleotides may comprise a modification which allows the coupling, binding or immobilisation of the respective oligonucleotide to a surface or a matrix, whereby all of the terms are used interchangeably. The immobilisation may be covalent or a non-covalent. The modification may be either terminal or non-terminal which means that it may be either located at a non-terminal nucleotide of the double-stranded DNA fragment or at the terminal nucleotide of the oligonucleotide. The latter modification is preferably realised once the oligonucleotide does not exhibit the loop structure but has the above-described bipartite structure. In such an embodiment, the modification is preferably attached to the 5' end of the upper strand or the 3' end of the lower strand. Such modifications comprise, among others, but are not limited to, biotin, iminobiotin, digoxygenin, sulfhydryl groups, dicyclohexylcarbodiimide, fluoresceine, acridine and rhodamine. The oligonucleotide may be coupled to a surface, preferably a matrix such as the inner wall of a multi-well plate, via avidin such as streptavidin, monomeric avidine, thyrosine-modified avidine, or antibodies, particularly such antibodies directed against any of the aforementioned compounds, sulfhydryl groups or any other suitable compound capable of specific binding of a ligand, which can be attached to an oligonucleotide, either during its synthesis or postsynthetically.

In a preferred embodiment of the inventive methods apart from the first and the further at least partially double-stranded oligonucleotides also the second oligonucleotide and consequently also the elongated oligonucleotide comprise this kind of modification. Given the discovery underlying the inventive methods, however, the modification incorporated by the second oligonucleotide is selected such that during steps a) to i) of the inventive methods the second at least partially double-stranded oligonucleotide and any elongated oligonucleotide comprising such second oligonucleotide may not be contacted with or be contained in a reaction or reaction vessel the surface of which allows the immobilisation through the modification. In accordance with this, the surface should not comprise a reactive group or compound which allows or mediates the binding of the oligonucleotide to the surface, particularly not via the modification. If, e.g., the modification is biotin, the respective surface should not have a streptavidin coating.

In accordance with the inventive methods, the first and the further at least partially double-stranded oligonucleotides comprise a part of the nucleic acid molecule to be manufactured. As in the Sloning method known in the art and, among others, described in WO 00/75368 also in the present inventive methods the nucleic acid molecule to be manufactured is a double-stranded nucleic acid molecule comprising an upper strand having a 5' end and a 3' end (read from left to right) (5'->3') and a lower strand having a 3' end and a 5' end (read from left to right) (3'->5'). Both strands are hybridised to each other by base pairing. The nucleic acid molecule to be manufactured is intellectually split up into a number of short double-stranded DNA fragments for the purpose of its manufacture. The length of these double-stranded DNA fragments depends on the number of the nucleotides transferred from the first or further oligonucleotides to the second oligonucleotide and the elongated oligonucleotide, respectively. These transferred nucleotides are also referred to herein as variable nucleotides. The part of the oligonucleotides of the respective libraries as described herein, which comprises the variable positions, is referred to herein as the variable region. The remainder of the oligonucleotides is referred to herein as constant region and comprises typically a recognition site of a type IIS restriction enzyme or a part thereof and, optionally, a terminal loop. The number of nucleotides transferred per reaction cycle determines the size of the library to be used in connection with the methods according to the present invention. The part of the nucleic acid molecule to be transferred in a single step from a first or further at least partially double-stranded oligonucleotide to the second and elongated at least partially double-stranded oligonucleotide thus comprises both strands of the individual double-stranded DNA fragments.

Because of this design, the first and further at least partially double-stranded oligonucleotides differ from each other primarily in the last nucleotide(s) of the 3' end of the upper strand and the last nucleotide(s) of the 5' end of the lower strand. Further differences may reside in the recognition site for the type IIS restriction enzyme.

For the design of the libraries of the first, second and further at least partially double-stranded oligonucleotides the following considerations are applicable: First, the number of nucleotides to be transferred during each elongation step, and, second, the length of the single-strand overhang. Based on these considerations a number of oligonucleotide libraries may be designed. For example, in case the synthesis is designed such that each of the double-stranded DNA fragments forming in their entirety the nucleic acid molecule to be synthesised, comprises three variable nucleotides on each strand, i.e. in each elongation step three nucleotides are added to both the 3' end of the upper strand and the 5' end of the lower strand of the second at least partially double-stranded oligonucleotide or of the elongated oligonucleotide, respectively, and a overhang of three nucleotides is realised, this means that a total of 4096 ($=4^6$) different at least partially double-stranded oligonucleotides have to be provided as first and further at least partially double-stranded oligonucleotides. This kind of library also requires a distinct number of second at least partially double-stranded oligonucleotides. For these second oligonucleotides the relevant design criterion is the length of the overhang. For a three nucleotide overhang, the total number of second at least partially double-stranded oligonucleotides is 64. This number of second oligonucleotides allows the coupling and ligation, respectively, to any first and any further at least partially double-stranded oligonucleotide also providing a three nucleotide overhang.

Library for the Three Nucleotide Overhang Elongation Variant.

As discussed in more detail in connection with the transposition step in the following paragraphs, a further category of first and further at least partially double-stranded oligonucleotides is required. In case the elongation procedure as described in the methods for the manufacture of a nucleic acid molecule uses elongated oligonucleotides with a three nucleotide overhang, a third class of at least partially double-stranded oligonucleotides is required to allow specific cleavage of intermediate products during the transposition phase. This is because presently no suitable pair of type IIS restriction enzymes is known with recognition sites that can be discriminated. To overcome this limitation, a new recognition site for another type IIS restriction enzyme has to be added in the last elongation step (before entering the transposition phase during which the preformed double-stranded DNA fragments are combined in a pairwise fashion). These 64 different at least partially double-stranded oligonucleotides are referred to herein as transition oligonucleotides or transition anchors. The number of transition oligonucleotides is increased to 320 different transition oligonucleotides if one wants to vary the lengths of the double-stranded DNA fragments. Depending on the distance of the recognition site for the type IIS restriction enzyme, which does not generate the 3 nucleotide overhang from the first nucleotide of the elongated oligonucleotide, this enzyme may or may not remove one base-pair from the elongated oligonucleotide. This option is highly advantageous because it allows the shifting of the ends of the double-stranded DNA fragments by one basepair. In this way it is possible to avoid the formation of elongation blocks, which have four nucleotide overhangs that are self-complementary. The presence of such overhangs would be expected to decrease the yield of the correct ligation products in the transposition phase because of the formation of self-ligated by-products. To synthesize any possible DNA with a three nucleotide overhang variant, the respective oligonucleotide library will have to comprise 4224 at least partially double-stranded oligonucleotides or 4416 at least partially double-stranded oligonucleotides, respectively if one wants to avoid the possible formation of self-complementary overhangs during the transposition phase.

Library for the One Nucleotide Overhang Elongation Variant

In case oligonucleotides with single-stranded overhangs having a length of one base and a total number of three transferable nucleotides are used, the number of required oligonucleotides is reduced to a total of 264. The respective library consists more particularly of a total of 256 different first and further at least partially double-stranded oligonucleotides with three variable nucleotides each at the 5' and the 3' end, which are staggered by one nucleotide. If one counts each variable position in both strands, a total of 4 positions are occupied by variable nucleotides, i.e. the total number of variants is 256 ($=4^4$). The first and further oligonucleotides contain six or more base pairs acting as recognition site for the type IIS restriction enzyme, an unspecified number of spacer base pairs and, except for bi-partite oligonucleotides, a terminal loop. The insertion of spacer base pairs is necessary because stable binding of the restriction enzymes used often depends on the presence of additional nucleotides outside the recognition site. In addition, four second at least partially double-stranded oligonucleotides and four transition oligonucleotides are required to make the transition from a one nucleotide overhang to a four nucleotide overhang. If four base pairs are to be transferred in each step, the corresponding variant of the oligonucleotide library consists of 1032 oligonucleotides, i.e. 1024 first and further at least partially double-stranded oligonucleotides having a one base pair overhang plus four second at least partially double-stranded oligonucleotides and four transition oligonucleotides.

Reverse Solid Phase Synthesis

In the inventive procedure called RSPS (reverse solid phase synthesis), the first and the second oligonucleotide are ligated to each other via their complementary overhangs. It is to be understood that the overhangs may only be those which are not blocked, neither by the modification nor by the loop structure as specified above. The ligation reaction as such is known to the one skilled in the art and can be performed according to standard protocols such as, among others, described in the examples attached hereto. In the ligation reaction a ligation product is generated, which is herein referred to as first ligation product. Said first ligation product is subsequently immobilised to the surface or a matrix. The immobilisation preferably occurs via the modification as specified above. After immobilising said first ligation product, the ligation product is cleaved by a type IIS restriction enzyme. More particularly, the restriction enzyme is the one the recognition site of which is incorporated in the first oligonucleotide having the modification used for the immobilisation of the first ligation product to the surface. The first and further oligonucleotides are designed in such a way that cleavage of the first ligation product releases an elongated second oligonucleotide. The added variable nucleotides correspond to a part of the nucleic acid molecule to be synthesised. More precisely, the released second oligonucleotide is elongated by those nucleotides 3' of the cleavage site of the upper strand of the first oligonucleotide. Such elongated second oligonucleotide is also referred to herein as elongated oligonucleotide. Due to the cleavage characteristics of the type IIS restriction enzyme the recognition site of which is incorporated in the first oligonucleotide, the elongated oligonucleotide will again have an overhang. However, this overhang is different from the originally used second oligonucleotide. This elongated oligonucleotide is then transferred to a further reaction, which preferably takes place in a further reaction vessel. In said reaction vessel either a further at least double-stranded oligonucleotide is present or is added thereto, whereby this further at least partially double-stranded oligonucleotide is of a design similar to the one of the first oligonucleotide, i.e. it has a modification which allows the oligonucleotide to be coupled to a surface and also comprises a recognition site for a further type IIS restriction enzyme cutting outside its recognition site. Also this further oligonucleotide comprises a single-stranded overhang. The overhang of the further oligonucleotide is partially or fully complementary to the overhang of the elongated oligonucleotide. The type IIS restriction enzyme the recognition site of which is incorporated in the further oligonucleotide may be the same or may be different from the restriction enzyme of the first oligonucleotide, i.e. the first type IIS restriction enzyme. Apart from this, similar to the design of the first oligonucleotide also this further oligonucleotide comprises one or several nucleotides which will become part of the nucleic acid molecule to be synthesised. As a next step this further oligonucleotide is then ligated to the elongated oligonucleotide. By repeating this sequence of steps, the length of the elongated oligonucleotide increases by the number of variable nucleotides per cycle. The elongated oligonucleotide is normally not immobilised but transferred from one reaction to a subsequent one. Compared to the starting second oligonucleotide the thus elongated oligonucleotide now comprises a double-stranded DNA fragment which is part of the nucleic acid molecule to be synthesised.

The present inventors have surprisingly discovered that by realising this particular sequence of steps, namely ligating the first and further oligonucleotides with the second or elongated oligonucleotides in solution, immobilising the ligation products and subsequently releasing the correctly cleaved elongated oligonucleotides for use in further reaction cycles, is advantageous over methods known in the art. This sequence of steps is in clear contrast to the original design of the Sloning method as described in international patent application WO 00/75368. Specifically, this reversed sequence allows to tremendously reduce the variety and number of by-products. The reason for this is that the present inventors have discovered that the ligation between the first and the second oligonucleotide works with high yield when both oligonucleotides are kept in solution rather than one of them being attached or immobilised to a surface. Additionally, the reaction kinetics are more controllable as wrong reaction products change the molarity of the reagents for further steps. Typically, the oligonucleotide which provides a part of the nucleic acid molecule to be manufactured by the inventive method, i.e. e. the donor oligonucleotide which is preferably the first and further oligonucleotide, respectively, is present in a new reaction vessel such as a well of a multi-well plate where it is not immobilised. The reason for this is that by doing so neither the uncleaved ligation product nor the uncleaved donor oligonucleotide, which are both immobilised via the modification, are transferred to a new ligation reaction. In the method described in international patent application WO 00/75368, incomplete cleavage of the growing immobilised oligonucleotide could result in the formation of incorrect or incomplete ligation products. By the particular use of the immobilisation step, all of the components of the reaction are removed which may be troublesome in subsequent steps.

Reverse Liquid Phase Synthesis

Basically, the inventive methods work with any type IIS restriction enzymes. Preferably those type IIS restriction enzymes are used which generate a three nucleotide long overhang at the 5' end such as SapI, Eam1104I and the isoschizomers EarI, Ksp632I, or those type IIS restriction enzymes generating a one nucleotide overhang such as BfiI, FmrI, BfuI, BciVI, BspPI, AclWI, AlwI, PleI, MlyI, PpsI.

As described in connection with the Sloning process known in the art and, e.g., subject to international patent application WO 00/75368, elongated double-stranded oligonucleotides having a single-stranded overhang are synthesised in parallel by the methods according to the present invention for the manufacture of a nucleic acid molecule. These elongated double-stranded oligonucleotides are, also referred to herein as elongation blocks, have to be ligated to each other to produce the full length nucleic acid molecule to be manufactured. By this parallel ligation of the elongation blocks, which is also referred to as transposition phase or transposition, any DNA molecules can be synthesized in very few steps, providing more reliable and more accurate products at higher yields compared to methods known in the art.

The first, further and second or elongated oligonucleotides are also referred to herein as "elongation intermediates". Any products prior to the ligation of the transition anchor are referred to as "elongation products". Upon cleavage these elongation products are referred to as "cut elongation products". After the ligation of the transition anchor these intermediates are called "elongation blocks". This latter wording reflects the fact that, except the corresponding ends, these blocks are represented as such in the nucleic acid to be manufactured. An elongation block is also a ligated elongated oligonucleotide as defined herein, which is also referred to herein as elongation product, or, after cleavage by the respective restriction enzyme, as cut elongation products. In accordance with the afore-given definition elongation blocks which were cut, are referred to as "cut elongation blocks". The ligation of two elongation blocks resulting in a first transition block with all other transition blocks being referred to as "transposition intermediates".

Transposition Variants

Given the methods for the manufacture of a nucleic acid molecule and more particularly the elongation blocks thus generated as described herein, there are basically two alternatives to combine them in what is called the transposition step. In the first alternative, only the first and further at least partially double-stranded oligonucleotides comprise a modification for immobilising the at least partially double-stranded oligonucleotide to a surface. Consequently, the elongation blocks obtained in step h) and i), respectively, of the method for the manufacture of a nucleic acid molecule according to the present invention, lack a modification, which allows binding to the matrix. As they can not be selectively bound to a surface or a matrix, they will therefore stay in solution.

The second alternative requires that both the first and further at least partially double-stranded oligonucleotides and the second oligonucleotide and any elongated oligonucleotide comprising such second at least partially double-stranded oligonucleotide as a moiety, have a modification, which allows the immobilisation to a surface. Preferably, the modifications of the first and further oligonucleotides and the second or elongated oligonucleotides allow the specific binding to different solid supports. Both alternatives may be realised according to the present invention. However, each alternative requires a distinct arrangement of the first and further at least partially double-stranded oligonucleotides and the orientation in which the nucleic acid molecule parts that are attached to the second and elongated oligonucleotide, are arranged.

In the first alternative, a first cut elongation block and a second cut elongation block are provided. The first cut elongation block can but does not necessarily have to be generated according to a method for the manufacture of a nucleic acid molecule according to the present invention. The same applies also to the second, third and fourth elongation block as used in the method for the synthesis of a nucleic acid molecule according to the present invention. As used in the inventive method for the synthesis of a nucleic acid molecule, the second cut elongation block and the fourth cut elongation block, may be further at least partially double-stranded oligonucleotides instead of cut elongation blocks. By ligating the first and the second cut elongation block and the third and the fourth cut elongation block, the first transposition block and the second transposition block, respectively, are generated. The ligation step may either be carried out with both cut elongation blocks in solution, or with one of the two cut elongation blocks being immobilised to a surface via a modification provided by the first or further at least partially double-stranded oligonucleotide moiety of the cut elongation block. The first and second transposition blocks are then cut by distinct and different type IIS restriction enzymes, whereby the restriction enzyme is either the first type IIS restriction enzyme or the second type IIS restriction enzyme. The first transposition block which is cut by the type IIS restriction enzyme is also referred to herein as first cut transposition block and the second transposition block which is cut by the different type IIS restriction enzyme is also referred to herein as second cut transposition block. Preferably, the first type IIS restriction enzyme releases the first cut transposition block whereas the second type IIS restriction enzyme releases the second at least partially double-stranded oligonucleotide moiety from the second transposition block, in which case the second cut transposition block remains immobilised to a surface. These first cut transposition block and second cut transposition block are subsequently combined and ligated using standard techniques. The then generated ligation product may then in a further ligation step be used as first and/or second transposition intermediate.

By using two different type IIS restriction enzymes for the generation of the first cut elongation block and the second cut elongation block, preferably selected from the enzymes Esp3I, Eco31I, BsaI, BpiI, BbsI, BpuAI, a correct orientation of the part of the nucleic acid molecule to be manufactured is guaranteed. Using this particular method, the sequence of the oligonucleotides transferred to any elongation block corresponds to—part of—the sequence of the nucleic acid molecule to be manufactured. In other words, if the nucleic acid molecule to be manufactured consists of elongation blocks 1 to 4, the transposition block 1 provides elongation blocks 1 and 2, and transposition block 2 provides elongation blocks 3 and 4, respectively, in that order.

Transition from Elongation to Transposition Reactions with Different Overhang Length For the transposition it is essential that the overhangs of the first cut and second cut elongation products are complementary to each other with regard to sequence and number of overhanging bases. The single-stranded overhangs of cut elongation products that correspond to adjacent double-stranded DNA fragments in the nucleic acid molecule to be manufactured are automatically complementary. However, if the first and further oligonucleotides and the second or elongated oligonucleotides contain recognition sites for type IIS restriction enzymes that generate single-stranded overhangs with different lengths, the resulting elongation products need to be modified in such a way that the overhangs produced by cleavage of the ligated elongated oligonucleotides with either one of the at least two different type IIS restriction enzymes match with each other before they can be combined. This can be achieved by using a particular designed further at least partially double-stranded oligonucleotide in the last step of the elongation phase. This kind of particular further at least partially double-stranded oligonucleotide is also referred to herein as transition oligonucleotide.

For example, if the type IIS restriction enzyme Eam1104I is used to generate the elongated oligonucleotides, a three nucleotide overhang is generated at the 5' end. In order to ligate different elongation products via single-stranded overhangs produced by different type IIS restriction enzymes, it is not possible use three nucleotide overhangs, since there are presently no different type IIS restriction enzymes known that recognize sequences, which can be discriminated. Therefore, in an embodiment of the inventive methods a three nucleotide overhang of an elongated oligonucleotide is transformed into a four nucleotide overhang to allow the ligation of another elongation block with an overhang generated by cleavage with type IIS restriction enzyme Esp3I. This can be realised by introducing a further elongation step in which the transition oligonucleotide is ligated to the elongation product; this transition oligonucleotide has a three nucleotide overhang but a recognition site for a four nucleotide overhang producing type IIS restriction enzyme such as Eco31I. After cleaving this last ligation product, a four nucleotide 5' overhang is generated which is complementary to the overhang of the corresponding next cut elongation block, which has been cleaved by the type IIS restriction enzyme Esp3I. A sequence complementarity is naturally given once the overhangs of the first cut elongation block and the second cut elongation block overlap each other by four nucleotides. The transition oligonucleotides can be designed such that cleavage with Eco31I yields an elongation block with the same 3' terminal nucleotide as before the ligation, but adding one nucleotide to the 5' end of the elongated oligonucleotide. Alternatively, transition oligonucleotides may be used in which the recognition site for Eco31I is one basepair closer to the end of the molecule. This shifts the position of cleavage one nucleotide up producing a cut ligated elongated oligonucleotide, which is shortened by one nucleotide at its 3' end. The alternative use of either type of transition anchor has one distinct advantage: one can thus avoid the formation of self-complementary single-stranded overhangs of the individual elongation blocks.

Using a one nucleotide overhang generating a type IIS restriction enzyme such as BfuI, the same principles apply. In the subsequent transposition steps the formed first and second cut elongation blocks are subsequently ligated to each other. One of two corresponding cut elongation blocks is always cut with the second type IIS restriction enzyme, in the present case, e.g. Esp3I. By doing so the elongation block or the product of the transposition reaction may thus be removed from the reaction, particularly from the reaction vessels such as a well, and may be transferred into a different reaction vessel. From the other cut elongation block the second at least partially double-stranded oligonucleotide moiety is cleaved off with the respective second type IIS restriction enzyme. This leaves an elongation block immobilised to a surface which comprises the transition oligonucleotide and a part of the nucleic acid molecule to be manufactured.

Semi-Inverted Transposition (SIT)

In a further embodiment of the transposition procedure using elongation blocks, the transpositions may be carried out as so-called semi-inverted transpositions (SIT). The SIT procedure is designed to significantly reduce the number of possible side products, which results in higher yields of the correct product. In contrast to the transposition procedure described above, half of the elongation blocks of the nucleic acid molecule to be synthesized are synthesized in an inverted orientation.

Whereas in the above described transposition reactions, the elongation blocks to be combined with each other have to cleaved by two different type IIS restriction enzymes, the SIT procedure relies on the use of only one type IIS restriction enzyme during all transposition steps except the first one. This procedure has several advantages: as the same enzyme is used for all transposition intermediates, the differences in the yield of these products can be minimized. This ensures that fairly comparable amounts of intermediate products are ligated. To further improve yield, one typically selects the type IIS restriction enzyme with the highest activity to cut most of the intermediates, confining the use of the enzyme with lower activity to a single step. Finally, the probability of the formation of unwanted side products is drastically reduced because the single-stranded overhangs to be ligated match only for those elongation blocks intended to fit. One disadvantage of the SIT procedure is the generation of intermediates that have two free ends rather than one. It is therefore impossible to use an exonuclease step to remove unligated side products.

The building blocks for the semi-inverted transposition are the elongation blocks. In the first step of one embodiment of the SIT procedure these elongation blocks are immobilised on a surface via the modification brought in by the transition oligonucleotides. All immobilised elongation blocks are then cut with the type IIS restriction enzyme, the recognition site of which resides in the portion of the molecule that is contributed by the second at least partially double-stranded oligonucleotide, thereby producing cut elongation blocks. One of each pair of immobilised cut elongation blocks that are adjacent in the nucleic acid molecule to be synthesised is then cut once more. This time one uses the type IIS restriction enzyme the recognition site of which is comprised in the portion of the molecule that is contributed by the further at least partially double-stranded oligonucleotide or the transition oligonucleotide. As a result, double-stranded DNA fragments with two free ends are generated; the moieties of the molecules containing the terminal loops remain bound to the surface. Cut elongation blocks and double-cut elongation blocks are then ligated in a pairwise fashion, forming new transposition intermediates roughly double the size of the elongation blocks that went into the ligation reaction. Since the single-stranded overhangs of the cut elongation blocks are complementary to only one of the free ends of the double-cut elongation blocks, the orientation of the ligation reaction is still preserved. All double-cut fragments can therefore only ligate in reverse orientation. Flipping the orientation of the double-cut transposition intermediates in each step ensures that their overhangs in most cases will not match the overhangs of any eventually remaining uncut side products. In the method according to international patent application WO 00/75368 all side products generated by incomplete cleavage and/or ligation can engage in subsequent reactions because the single-stranded overhangs produced by cutting with the other type IIS restriction enzyme all have an identical sequence. Due to this orientation change of the transposition intermediates, it is essential that in the preceding steps the sequences of every other elongation block are built up in inverse orientation relative to the sequence of the part of the nucleic acid molecule to be manufactured. When designing a synthesis according to the SIT procedure, certain conditions should be met: the single-stranded overhangs of all intermediates should neither be complementary to each other nor self-complementary. The latter limitation may be overcome by appropriately shifting the boundaries of the elongation blocks, which make up the nucleic acid to be synthesized as described above. In case the desired nucleic acid molecule contains highly repetitive sequences, the first condition may not always be possible to comply with.

In a further embodiment of the SIT procedure, the transpositions may be carried out without the prior addition of a transition oligonucleotide. As in the above case, all immobilised elongation blocks are first cut with the restriction enzyme specific for the second at least partially double-stranded oligonucleotide, thus generating single cut elongation products with one free end and one blocked end. Every other single cut elongation block is then cleaved with the restriction enzyme specific for the last further at least partially double-stranded oligonucleotide to produce a double cut elongation block, which is released from the solid support. These double cut elongation blocks are then ligated to their matching single cut elongation blocks in inverse orientation relative to their direction of synthesis. The overhangs used for this ligation have the same length. However, their length may be different from the length of the overhangs produced by the restriction enzyme the recognition site of which resides in the moiety of the molecule provided by the last further at least partially double-stranded oligonucleotide. The resulting transposition intermediates again have one free end, which is compatible with the overhang produced by the restriction enzyme specific for the last further at least partially double-stranded oligonucleotide. By this way it is possible to join fragments that have different overhangs. With the SIT procedure, a nucleic acid molecule to be manufactured containing the nucleotides 1-80 is assembled as shown in FIG. 12, with half of the elongation products having been built up in inverse orientation.

Double Selection Procedures

In a further embodiment of the transposition procedure of the present invention, the transposition procedure may be further differently designed to introduce a second selection by using oligonucleotides carrying different modifications. Double selection methods are applicable in connection with both the RLPS and the RSPS method as disclosed herein. A common characteristic of these transposition variants is that both the first, the further and the second at least partially double-stranded oligonucleotide comprise a modification which allows the immobilisation of the respective oligonucleotides to a surface. Here the modification attached to the first and further at least partially double-stranded oligonucleotide is different from the one of the second at least partially double-stranded oligonucleotide. Thus the first and the second ligated elongated oligonucleotides comprising such first or further and second at least partially double-stranded oligonucleotide moieties comprise two different modifications allowing their preferably specific immobilisation to a surface such as the coated wall of the well. Preferably, the first and the second ligated elongated oligonucleotides are built up in a manner similar to the method for the manufacture of a nucleic acid molecule as disclosed herein, such as RSPS and RLPS, respectively. Once anelongation block is completed, it is cut with first of the two restriction enzymes the recognition sites of which are contained within its sequence. It is then preferably ligated to a further elongation block, which is cut with the second of the two restriction enzymes the recognition sites of which are contained within its sequence, thereby forming a first transposition block. The ligation is preferably carried out in solution. The various parts of the nucleic acid molecule to be manufactured are synthesised in independent reactions using the various elongation reactions disclosed herein.

It is also within the present invention that the standard procedure of the Sloning method as described in international patent application WO 00/75368 is realised. A first elongation block is transferred to a reaction vessel the surface of which is coated such as to allow the modification attached to the second at least partially double-stranded oligonucleotide now part of the respective elongation block, thereby immobilising the first elongation block. The second elongation block is transferred to a different reaction vessel. The surface of said different reaction vessel is differently coated to allow the immobilisation of the second elongation block to the surface via the modification attached to the moiety contributed by the last further at least double-stranded oligonucleotide. The immobilised second elongation block is subsequently cleaved by the type IIS restriction enzyme the recognition site of which is contained in the moiety contributed by the last further at least partially double-stranded oligonucleotide. This releases a cut second elongation block comprising the second at least partially double-stranded oligonucleotide moiety with the respective modification and a part of the nucleic acid molecule to be manufactured. In parallel or subsequently the immobilised first elongation block is cleaved by the type IIS restriction enzyme the recognition site of which is contained in the moiety contributed by the second at least partially double-stranded oligonucleotide. Upon such cleavage a cut first elongation block is released which comprises a part of the nucleic acid molecule to be manufactured and, in addition, the moiety contributed by the last further at least partially double-stranded oligonucleotide. The released cut elongation blocks lack merely the second or the last further at least partially double-stranded oligonucleotide or a part thereof, respectively.

The thus released cut elongation blocks are preferably transferred to a different reaction vessel where ligation of said two cut elongation blocks is carried out using standard methods. The thus created ligated oligonucleotide is called a transposition block. This transposition block comprises a first moiety contributed by the last further at least partially double-stranded oligonucleotide of the first elongation block, and a second moiety contributed by the second at least partially double-stranded oligonucleotide of the second elongation block, both retaining their respective different modifications. Furthermore, this transposition block comprises the parts of the nucleic acid molecule to be synthesized provided by both the first and the second elongation block.

The same series of reactions is carried out with further pairs of elongation blocks to produce further transposition blocks. The resulting transposition blocks are then again immobilised to either the first or the second modified surface by virtue of one of their modifications; these transposition steps are repeated until the nucleic acid molecule to be manufactured is completed.

Depending on the reaction scheme and the different type IIS restriction enzymes used, the orientation of the moiety forming the parts of the nucleic acid molecule to be synthesized and to be transferred in the transposition steps may or may not have to be inversed.

The present invention is now further illustrated by reference to the following figures and examples, whereby FIG. 1A-FIG. 1F show the various steps of the RSPS method with oligonucleotides having a three nucleotide overhang at the 5' end;

FIG. 2A-FIG. 2F show the various steps of the RSPS method with oligonucleotides having a one nucleotide overhang at the 3'-end;

FIG. 3A-FIG. 3E show the various steps of the RLPS method with oligonucleotides having a three nucleotide overhang at the 5' end;

FIG. 4A-FIG. 4E show the various steps of the RLPS method with oligonucleotides having a one nucleotide overhang at the 3' end.

FIG. 5A-FIG. 5J show the transition from the elongation phase to the transposition phase for the three nucleotide overhang variant;

FIG. 6A-FIG. 6D show the transition from the elongation phase to the transposition phase for the one nucleotide overhang variant;

FIG. 7A-FIG. 7D show the semi-inverted transposition procedure as an embodiment for the transposition method used for the manufacture of the nucleic acid molecule;

FIG. 8A-FIG. 8G illustrate the embodiment of the transposition according to the double selection or pingpong procedure;

FIG. 10 shows the arrangement of the elongation blocks to be used in the transposition according to the double selection method;

FIG. 11 shows the reactions according to the SIT procedure with different overhang lengths.

Figure 12:

FIG. 12 shows a comparison of the effectiveness of the SPS method of WO 00/35768 and the RLPS method for the manufacture of nucleic acid molecules according to the present invention The method according to the present invention which is herein referred to as RSPS, is depicted in its various steps in FIG. 1A-FIG. 1A shows a first and a second at least partially double-stranded oligonucleotide, whereby the first oligonucleotide is also referred to as first anchor oligonucleotide and the second oligonucleotide is also referred to as splinker oligonucleotide. The first anchor oligonucleotide comprises a recognition site for the type IIS restriction enzyme Eam1104A and in addition thereto a part of the nucleic acid molecule to be manufactured which in the present case and given the cleavage site of Eam1104I is on the upper strand TAC and on the lower strand GCG (both in the 5'->3' orientation). The overhang of the first anchor oligonucleotide is complementary to the respective overhang at the 5'-end of the splinker oligonucleotide. The splinker oligonucleotide comprises a recognition site for a type IIS restriction enzyme, in this case for Esp3I. Both the first anchor oligonucleotide and the splinker oligonucleotide show a unipartite structure which means that the upper strand and the lower strand are part of one contiguous oligonucleotide, which can form a double-stranded structure with an internal loop, in the present case consisting of four Ts. This loop structure is a possible modification of the non-overhanging ends, which are not to be ligated according to the present invention. The first anchor oligonucleotide additionally comprises a modification which allows the specific immobilisation to a surface. In the present case, the first anchor oligonucleotide comprises a biotin group which allows immobilisation to a streptavidin coated surface. The splinker oligonucleotide and the anchor oligonucleotide are subsequently ligated generating a first ligation product (FIG. 1B). The ligation is mediated by T4 DNA ligase after hybridising the complementary overhangs of the first anchor oligonucleotide and the splinker oligonucleotide. The first ligation product is subsequently immobilised on a streptavidin-coated surface. Streptavidin specifically binds the biotin modification of the first anchor oligonucleotide moiety of the first ligation product (FIG. 1C). The modification of surfaces such as coating with streptavidin is well-known in the art and, for example, described in Huang S C, Swerdlow H, Caldwell C D Anal Biochem 1994; 222: 441-9.

In a subsequent step the immobilised first ligation product is washed, preferably twice, using a buffer. In addition, the remaining ligase activity is inactivated by heating the reaction to 65° C. for 10 min. By subsequent washing steps any products different from the first ligation product are actually removed from the reaction thus allowing an exact calibration of the reaction parameters needed for subsequent steps of the method. One of the next steps is the cleavage of the first ligation product using the type IIS restriction enzyme Eam1104I which is also referred to herein as the first type IIS restriction enzyme (FIG. 1D-1E). Due to the particular arrangement of the part of the nucleic acid molecule to be provided in this step distal from the cleavage site of the respective type IIS restriction enzyme an elongated oligonucleotide is generated and released from the first ligation product whereas the first oligonucleotide or the remaining part thereof, respectively is (or remains) immobilised to the surface. Due to this arrangement the first oligonucleotide actually serves as donor and the second oligonucleotide as acceptor molecule. The elongated oligonucleotide, which is also referred to as elongated splinker is thus the second oligonucleotide which has now incorporated the part originally contained in the first oligonucleotide and which has been donated by the first oligonucleotide and corresponds to a part of the nucleic acid molecule to be manufactured. This elongated oligonucleotide is then transferred to a new reaction, typically in a new reaction vessel. In said reaction vessel a further oligonucleotide is already provided or added thereto (FIG. 1F). This further oligonucleotide has a design similar to the one of the first oligonucleotide. This means that also this further oligonucleotide is at least partially double-stranded and has a modification, which allows a coupling of the oligonucleotide to a surface. Also, it comprises a recognition site for the further type IIS restriction enzyme which cuts outside its recognition site and which oligonucleotide comprises a single-stranded overhang. This further oligonucleotide is more particularly characterised such that it comprises again a part of the nucleic acid molecule to be synthesised. This fragment of the further oligonucleotide referred to in FIG. 1F as second anchor oligo is distal from the cleavage site of the respective type IIS restriction enzyme. The distance between the recognition site and the cleavage site for the particular restriction enzyme of the further oligonucleotide determines the size of the DNA fragment to be transferred: in the present case a stretch of three nucleotides (CGC) in the upper strand and three nucleotides (ATA) in the lower strand. Subsequently, the steps described before are repeated to add another stretch of three nucleotides onto both ends of the elongated second oligonucleotide. By repeating this process in each round another three nucleotides are added to the elongated oligonucleotide. The original second oligonucleotide thus finally contains a double-stranded DNA fragment of typically around 20 base pairs, which forms a part of the nucleic acid molecule to be manufactured. Once all elongation steps have been completed, this fragment is also referred to herein as "elongation block".

FIG. 2A-FIG. 2F show the method according to the present invention, more particularly the RSPS method using oligonucleotides which have a one nucleotide long overhang at the 3' end.

Again, the first oligonucleotide, herein also referred to as first anchor oligonucleotide, is of a unipartite structure, i.e. the two strands of nucleotides forming the double-stranded structure are part of one contiguous oligonucleotide, which can form a double-stranded structure with an internal loop. This loop structure is comprised of four Ts whereby one of said four Ts, preferably the most distal one, comprises a further modification which allows the immobilisation of the first oligonucleotide to a surface. In the present case, the modification is a biotin residue. The first oligonucleotide comprises a recognition site specific for BfuI, which is also referred to as first type IIS restriction enzyme. Distal to the cleavage site of BfuI further nucleotides are attached to both strands. In the present case the sequence 5' CCGT 3' is added to the upper strand and the sequence 3' AGGC 5' to the lower strand. The first oligonucleotide thus comprises a one nucleotide overhang at the 3'-end and a total of three base pairs in the double strand which define the particular species of this anchor onligonucleotide. The second oligonucleotide is in the present case also of a unipartite structure whereby the two strands forming the double-stranded structure of the second oligonucleotide are again linked by a four nucleotide loop. In the present case the loop is formed by four Ts (FIG. 2A). The second oligonucleotide comprises a recognition site for Esp3I, which is also referred to herein as the second type IIS restriction enzyme. Both the first and the second oligonucleotide are ligated using standard protocols resulting in the first ligation product depicted in FIG. 2B. This first ligation product is subsequently immobilised to a surface via the biotin modification of the first oligonucleotide and the first ligation product, respectively. The surface is coated by streptavidin, which allows specific retention of the biotinylated oligonucleotide species. The thus immobilised first ligation product is subsequently washed using standard protocols, preferably with buffers allowing removal of any of the reaction ingredients, particularly any remaining unligated second oligonucleotide and the typically heat inactivated ligase (2C). In a further step the immobilised ligation product is cleaved by BfuI (FIG. 2D-2E). BfuI generates two cleavage products, an elongated second oligonucleotide and a shortened first oligonucleotide. The first oligonucleotide lacking the four nucleotides of the upper strand and four nucleotides of the lower strand that had previously been present distal to the cleavage site. Insofar, this first oligonucleotide acts as donor whereas the second oligonucleotide acts as acceptor. Compared to the second oligonucleotide used in the step as depicted in FIG. 2A, the second oligonucleotide now comprises those nucleotides donated or transferred from the first oligonucleotide to the second nucleotide, which is now referred to herein as elongated oligonucleotide. The elongated oligonucleotide may be transferred into a different reaction vessel whereas by-products such as the uncleaved first ligation product and the unligated first oligonucleotide remain bound to the surface via the biotin modification. The elongated oligonucleotide is then combined with a further oligonucleotide which acts again as a donor for the nucleotides to be followed in the sequence of the nucleic acid molecule to be manufactured the first part of which is already attached to the elongated oligonucleotide.

As may be taken from the aforegiven description, it is clear that the method works both with oligonucleotides comprising a 5'-overhang and oligonucleotides comprising a 3'-overhang.

The method according to the present invention which is herein also referred to as RLPS, is depicted in its various steps in FIGS. 3A-3E. FIG. 3A shows the two oligonucleotides whereby the first oligonucleotide is also referred to as the first anchor oligonucleotide and the second oligonucleotide is also referred to as splinker oligonucleotide. The first anchor nucleotide has a design which is actually the same as the one for the first oligonucleotide according to the RSPS method as described in FIGS. 1A-1F and FIGS. 2A-2F, respectively. The same applies also to the splinker oligonucleotide (FIG. 3A). The first and the second oligonucleotide are ligated using standard protocols via their overhangs, generating a first ligation product (FIG. 3B). In contrast to the RSPS method, the thus obtained first ligation product is subsequently cleaved by the first type IIS restriction enzyme, in the present case Eam1104I. This results in a shortened first oligonucleotide and an elongated second oligonucleotide whereby the latter one is also referred to as elongated oligonucleotide (FIG. 3C). As described for the RSPS method, the first oligonucleotide comprises a part of the nucleic acid molecule to be manufactured. This part has been transferred to the second oligonucleotide.

In a subsequent step the thus obtained shortened first oligonucleotide and the elongated second oligonucleotide are separated by immobilising the first oligonucleotide, more particularly the shortened first oligonucleotide, via the modification to a surface (FIG. 3D). The elongated oligonucleotide originating from the second oligonucleotide by transferring a part of the nucleic acid molecule to be manufactured is kept in solution and may be subject to further elongation steps. This is typically done by transferring the reaction solution to a reaction vessel such as a well of a multi-well plate where the surface of the well is coated to allow a specific interaction with the modification of the shortened first oligonucleotide. In the present case the modification of the first oligonucleotide and the shortened first oligonucleotide, respectively, is a biotin and the bottom and the walls of the reaction vessel are coated with streptavidin. The shortened first oligonucleotide is immobilised to said surface whereas the elongated oligonucleotide is contained in the liquid phase of the reaction. The liquid phase or a part thereof is subsequently transferred to a new reaction vessel to which a second anchor oligonucleotide is added (FIG. 3E). Basically, this second anchor oligonucleotide is the further oligonucleotide according to the RLPS method which differs from the first oligonucleotide in the nucleotides which are to be transferred from the second anchor oligonucleotide to the elongated oligonucleotide obtained from the preceding steps. This reaction sequence may be repeated one or several times resulting in an elongated oligonucleotide which has a plurality of nucleotide groups transferred from the first oligonucleotide and subsequent further oligonucleotides to the second oligonucleotide, thus forming a part of the nucleic acid molecule to be manufactured.

FIG. 4A-4E illustrates the RLPS method with oligonucleotides having a one nucleotide overhang at the 3' end. As may be taken from FIGS. A-E the steps carried out are essentially the same as explained in connection with the RLPS method using oligonucleotides having a three nucleotide overhang at the 5' end. The only difference resides in the length and location of the overhang.

FIG. 5A-5J show the addition of a transition anchor and the first transposition step with elongated oligonucleotides having a three nucleotide overhang at the 5' end. As depicted in FIG. 5A two ligated elongated oligonucleotides are provided which are referred to herein as elongation product # 1 and elongation product # 2. The elongation product # 1 contains the first part of the nucleic acid molecule to be manufactured compared to the part of the nucleic acid molecule to be manufactured whereas the elongation product # 2 contains the second part of the nucleic acid molecule to be manufactured. The sequence order is taken from the upper strand of the respective double-stranded nucleic acid molecule to be manufactured with the 5' end being on the left side and the 3' end being on the right side (5'→3'). In the present case, both the first elongation product and the second elongation product contain recognition sites for two different type IIS restriction enzymes with the restriction enzyme Eam1104I being the first and further type IIS restriction enzyme Esp3I being the second type IIS restriction enzyme.

Upon cleavage of both elongation product # 1 and elongation product # 2 with Eam1104I, the respective cut elongation products are released (FIG. 5A-5B). Both cleavage products have a three nucleotide long single-stranded overhang at the 5' end. Both elongation products are transferred into new reaction vessels where a further at least partially double stranded oligonucleotide, in this case a so-called transition anchor is added. Transition anchors are characterised by the property that they comprise a recognition site for a type IIS restriction enzyme, which produces a single-stranded overhang, which is different in length from their original overhang prior to cleavage. Apart from this, the sequence of reactions is the same as in the preceding elongation steps.

In the present case the further at least partially double-stranded oligonucleotides are also referred to as transition anchor # 1 and transition anchor # 2 which are added to said two independent reactions. The transition anchor # 1 and transition anchor # 2 are chosen to match the overhangs of the first and second elongated oligonucleotides. Both transition anchors comprise a recognition site for a further type IIS restriction enzyme, in this case Eco31I (FIG. 5C).

In the next step the first cut elongation product is ligated with the corresponding transition oligonucleotide (transition anchor # 1) and the second cut elongation product is ligated with the required transition oligonucleotide (transition anchor # 2). The ligation products thereof (elongation block # 1 and elongation block # 2) (FIGS. 5D, E and F) now comprise two different recognition sites for type IIS restriction enzymes (in the present case Esp3I and Eco31I), which produce overhangs of identical length. Both ligation products are subsequently immobilised in separate reaction wells via their modification contained in the transition anchor moiety (FIG. 5F). As each of the ligation products comprises a part of the nucleic acid molecule to be manufactured and said parts are consecutive parts of the nucleic acid molecule to be manufactured, the following transposition step combines said two parts, creating a larger fragment of the nucleic acid molecule to be manufactured. In this transposition step the elongation block # 1 is cleaved by Eco31I, i.e. the further type IIS restriction enzyme, thereby releasing a first cut elongation block having a four nucleotide overhang at the 5' end (FIG. 5G). This released product retains the recognition site for the second type IIS restriction enzyme (Esp3I). The elongation block # 2 is still immobilised to a surface via the modification and is subsequently cleaved by Esp3I (the second type IIS restriction enzyme). By this cleavage a further oligonucleotide, more particularly a second cut elongation block is generated which, apart from the original second oligonucleotide, comprises all of the nucleotides which have been generated in the prior elongation steps. The only difference is that this cut elongation block now comprises a four nucleotide single-stranded overhang at the 5' end (FIG. 5H). In the final step the cut elongation block #1 and the cut elongation block #2 as generated in the steps described in FIGS. 5G and 5H, are combined and ligated generating a first transposition block (FIG. 5I, J).

The resulting transposition block may in turn be subject to further transposition steps to yield larger transposition blocks. All transposition blocks generated in this way comprise recognition sites for two different type IIS restriction enzymes, which will produce complementary single-stranded overhangs if the respective transposition products contain consecutive fragments of the nucleic acid molecule to be manufactured. It is to be noted that the transition oligonucleotides may or may not contribute nucleotides to the nucleic acid molecule to be manufactured depending on the number of nucleotides distal to the cleavage site.

FIG. 6 shows the addition of transition anchors to elongation products having a one base single-stranded overhang at the 3' end.

The respective processes are depicted in FIG. 6A-6D. All subsequent transposition steps are in principal identical to the ones depicted in FIGS. 5E-5J. The most important difference of this procedure resides in the fact that as further type IIS restriction enzyme BfuI is used, which creates a one nucleotide overhang at the 3'end. The transition anchors have to be designed accordingly to contain a one nucleotide overhang (as depicted in FIG. 6C). As in the previous example, the transition anchors provide the recognition site for a type IIS restriction enzyme that produces an overhang, which is compatible with the one produced by the second type IIS restriction enzyme (here Esp3I).

The semi-inverted transposition method is a particular form of the transposition step typically used in the method for the manufacture of a nucleic acid molecule according to the present invention. In FIG. 7A a first and a second elongation block are provided. It is to be noted that basically, the first elongation block may be produced by any of the methods disclosed herein such as the RSPS method or the RLPS method. However, it is also within the present invention that said first elongation block and said second elongation block, respectively, may be produced according to the description for the generation of elongated oligonucleotides subject to transposition steps as described in international patent application WO 00/75364 or in the European patent application 011 27 864.5.

The first and the second elongation block are preferably kept in different reaction vessels such as individual wells of a multi-well plate. Both elongation blocks are immobilised to a surface through the modification provided by the first or further oligonucleotide moiety of the respective elongation block. In the present case, the first or further type IIS restriction enzyme is Eco31I and the second type IIS restriction enzyme is Esp3I (FIG. 7A). Both the first and the second elongation block are cleaved by Esp3I and subsequently washed (FIG. 7B). Due to this treatment, the second oligonucleotide moieties of the first and second elongation block are removed. In addition, both the first and the second elongation block have in the present case a four nucleotide long overhang at the 5' end (FIG. 7B). The cleavage product resulting from cleaving the first elongation block, which is also referred to herein as first cut elongation block is subsequently cut with the first type IIS restriction enzyme, in this case Eco31I (FIG. 7C).

The thus released linear double-stranded oligonucleotide, a part of the nucleic acid molecule to be manufactured, is subsequently transferred as part of the supernatant of the respective cleavage reaction to a further reaction vessel, which contains the second cut elongation block immobilised to the surface of the reaction vessel via the modification (FIG. 7D). Here the modification is biotin and the solid phase streptavidin. Via the complementary overhangs of the transferred linear at least partially double-stranded oligonucleotide and the immobilised second cut elongation block, both molecules may be ligated according to standard protocols. The ligation product in turn comprises an overhang, in the present case a four nucleotide long overhang at the 5' end, which is the basis for further transposition reactions as described herein.

By transferring the linear double-stranded oligonucleotide released from the first cut elongation block to the second elongation product, the orientation of this former fragment is reversed. This ensures that side products generated by incomplete restriction enzyme cleavage in preceding steps do in most cases not contain the matching overhang required for proper ligation with the correct transposition block. To provide the basis for this orientation change, it is essential that in the preceding elongation steps, the sequence of every other elongation block is built up in an inverse order compared to the sequence of the nucleic acid molecule or part thereof to be manufactured.

Figure 8G:
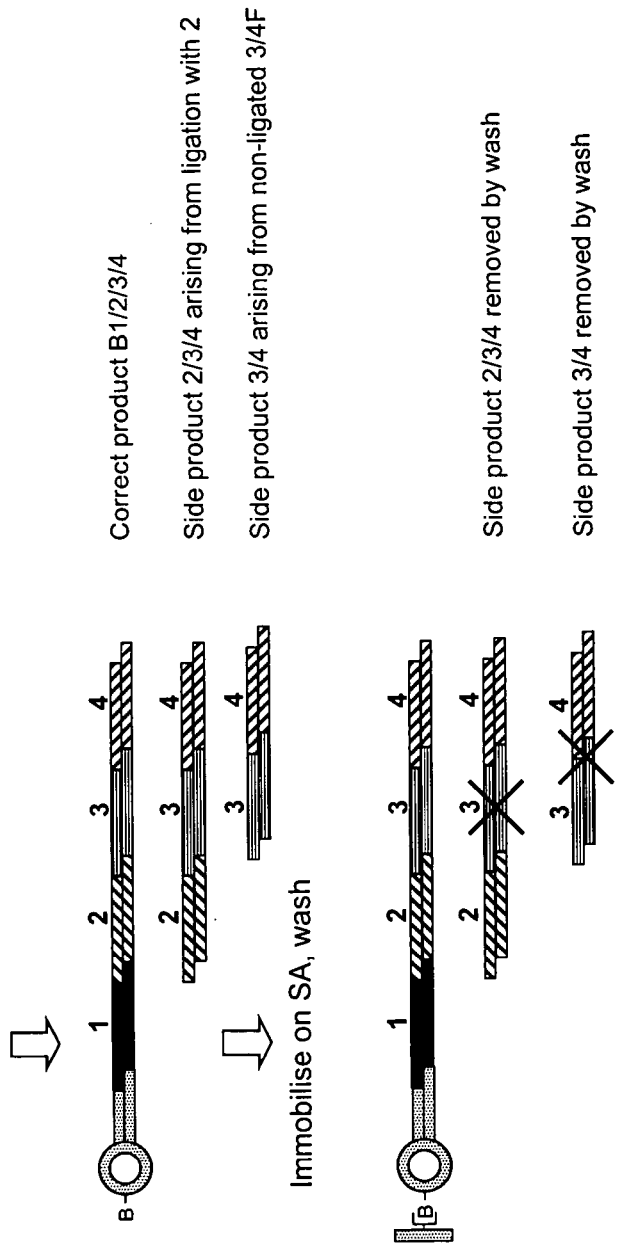

FIG. 8 illustrates the embodiment of the transposition procedure referred to herein as double selection or pingpong method, respectively.

As depicted in FIG. 8A four different elongation products are ligated in solution to their respective transition anchors (having complementary overhangs). In the present case, the modification of the transition anchors is biotin; the modification attached to the elongation products is FITC. In independent reactions, the elongation products are ligated with the transition anchors. The respective ligation products are in principle further ligated oligonucleotides. However, for reason of simplification, they are herein referred to as elongation blocks. These elongation blocks are then bound to a solid support (FIG. 8B), whereby the first and the third elongation block are bound to a surface specifically interacting with FITC, which in the present case is a well of a microplate coated with an anti-FITC antibody, whereas the second and the fourth elongation block are attached via the modification provided by the transition anchor moiety. In the present case, the latter modification is biotin and the respective surface is a well of a microplate coated with streptavidin (FIG. 8B). The thus immobilised elongation blocks are then washed and subsequently cleaved with either Eco31I (biotinylated elongation blocks) or Esp3I (FITC-labeled elongation blocks).

In all cases, the released cleavage products are further used, whereas the moieties that remain immobilised in the wells are excluded from subsequent reactions since they constitute undesired side products. The thus created cut elongation blocks are combined and ligated in a pairwise fashion, preferably in solution creating a first transposition block, which again carries both modifications ('B' and 'F') (FIG. 8D). These first transposition blocks are then used to carry out a further transposition step. As shown in FIG. 8E, the different first transposition blocks are again immobilised on either streptavidin or anti-FITC antibody coated wells in such a way that each one of a pair of transposition blocks adjacent in the nucleic acid to be manufactured is bound to the other surface.

In contrast to the previous cleavage reactions, the anti-FITC antibody-bound transposition blocks are now cut with Esp3I, whereas the streptavidin-bound transposition blocks are cut with Eco31I (FIG. 8F). Again, the released DNA fragments are carried through further transposition steps, whereas the uncleaved transposition blocks remain bound to their respective solid support. However, all further transpositions may produce linear double-stranded side products resulting from incomplete ligation during the previous cycle (fragments 2 and 3 in FIG. 8F). By immobilising the released cleavage products of one reaction (in this case the Esp3I cleavage), one can get rid of fragment 3 (albeit at the expense of a slightly lower efficiency of a ligation with one react and bound to a solid support). Fragment 2 would be transferred as a side product from the Eco31I cleavage reaction. Due to its compatible overhang, it can also form a ligation product with the correct transposition block 3-4F, thus leading to the formation of the side product 2-3-4F in addition to the correct transposition intermediate 1-2-3-4F (FIG. 8F). Upon cleavage with Esp3I and transfer of these two released products to streptavidin-coated wells, only the correct product, the transposition intermediate B1-2-3-4F can bind to the surface, whereas the side product 2-3-4F is washed away. In an analogous manner, by alternate binding of the transposition intermediates to either the anti-FITC antibody or streptavidin-coated solid support, any of the side products are effectively removed from the subsequent cycles. As the intermediates keep going back and forth between the two different types of solid support, this mechanism is also referred to herein as pingpong mechanism.

Figure 9A:
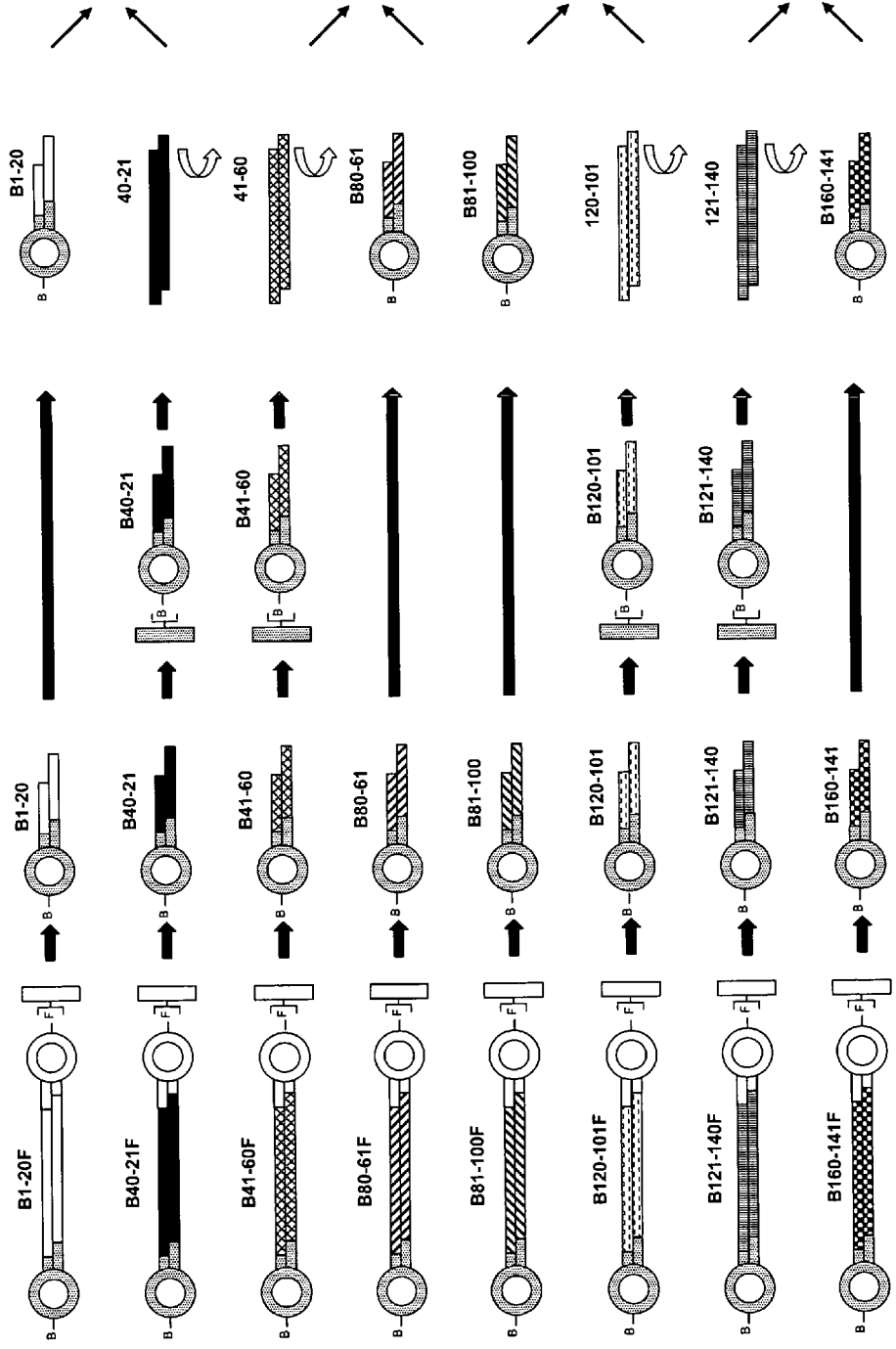
FIG. 9 shows the combination of the double selection procedure and the SIT method disclosed.

FIG. 9 shows a combination of the double selection procedure and the SIT method disclosed herein. First, all elongation blocks are immobilised via one of the two modifications present, in the present case via FITC (F). Then all elongation blocks are cut with the type IIS restriction enzyme the recognition site of which is contained in the moiety contributed by the second at least partially double-stranded oligonucleotide. This type IIS restriction enzyme is used only in the first transposition step (FIG. 9A). In all subsequent transposition steps, only the type IIS restriction enzyme the recognition site of which is contained in the moiety provided by the last further at least partially double-stranded oligonucleotide is required. Consequently, the variation in cleavage efficiency in the individual transposition steps is minimised because two different type IIS restriction enzymes generally display different cleavage efficiencies. For maximal standardisation it is therefore favorable to use only one enzyme.

After the first cleavage, all cut elongation blocks are released from the surface to which they were attached by virtue of the modification supplied by the second at least partially double-stranded oligonucleotide. The cut elongation blocks now retain only one modification, i.e. the one that was contributed by the last further at least partially double-stranded oligonucleotide. All cut elongation blocks are then bound to a surface via the remaining modification, in the present case biotin. Each one of a pair of cut elongation blocks is then cleaved a second time, this time with the type IIS restriction enzyme the recognition site of which is contained in the moiety contributed by the last further at least partially double-stranded oligonucleotide. This releases linear, double cut double-stranded fragments, which are then ligated in inverse orientation with their respective single cut immobilised elongation blocks to yield the first transposition blocks (FIG. 9B, left side). To generate the next larger transposition blocks, again each one of pair of transposition blocks is cleaved with the type IIS restriction enzyme the recognition site of which is contained in the moiety contributed by the last further at least partially double-stranded oligonucleotide to produce linear double-stranded transposition intermediates. These are subsequently again ligated to their respective single cut immobilised transposition blocks (FIG. 9C). As in all SIT procedures, the orientation of the transferred intermediates flips in each step.

FIG. 10 shows the arrangement of the elongation blocks for standard transpositions as well as for the SIT method disclosed herein.

FIG. 11 shows another embodiment of the SIT procedure, in which elongation blocks with overhangs of different length are combined without the need of transition anchors. Here the immobilised elongation products are first cut with the restriction enzyme the recognition site of which was contributed by the second at least partially double-stranded oligonucleotide, in this case generating cut elongation blocks having a 4 nucleotide overhang (FIG. 11A). These single cut elongation blocks are still attached to the surface. In the next step, each one of a pair of cut elongation blocks is cleaved with the type IIS restriction enzyme the recognition site of which is contributed by the last further at least partially double-stranded oligonucleotide, thereby releasing linear double cut double-stranded fragments with a 3 nucleotide overhang on one side and a 4 nucleotide overhang on the other side (FIG. 11B). These fragments are ligated with their respective single cut immobilised elongation blocks via their 4 nucleotide overhangs (FIG. 11C). The resulting ligation products contain only one free end, in the present case having a 3 nucleotide overhang. In subsequent steps, each one of a pair of matching first transposition blocks is cleaved by the type IIS restriction enzyme the recognition site of which is contributed by the last further at least partially double-stranded oligonucleotide during the last elongation step. This releases double cut double-stranded transposition blocks that possess 3 nucleotide overhangs on both sides of the molecule. As overhangs with an odd number of nucleotides can never be self-complementary, only the intended ligation partners have perfectly matched complementary overhangs and are thus selected for further ligations of larger transposition blocks.

FIG. 12 shows a polyacrylamide gel displaying the reaction products and by-products of the SPS method as detailed in WO 00/75364 and the RLPS method according to the present invention. The set-up of the respective reactions is fundamentally different in the above procedures: in the SPS method according to WO 00/75364 the elongation blocks are built up on the solid phase whereas the present invention describes the construction of elongation blocks in the liquid phase, which allows to select for the correctly elongated oligonucleotides. Hence the nucleotides to be added in each step are derived from the non-immobilised splinker oligonucleotide in the SPS method but from the immobilised anchor, also referred to herein as first or further at least partially double-stranded oligonucleotide in the case of the RLPS procedure. This is why the reaction products can be only indirectly compared. FIG. 12A shows the released shortened splinker oligonucleotides of an elongation according to the SPS method. The direct gel analysis of the elongated anchor is not possible since it is immobilised to a surface and thus not available as an intact molecule. The presence of the shortened splinker oligonucleotide, which has acted as donor in the ligation/restriction cycle is but an indirect evidence for a successful reaction cycle. The formation of side products goes unnoticed until the elongated oligonucleotides are cleaved from the anchor oligonucleotide, i.e. the first at least partially double-stranded oligonucleotide, which in this case however acts as acceptor rather than as donor. These side products, which arise from incomplete restriction of the elongated anchor oligonucleotides, were analysed by cleaving the elongated anchor oligonucleotide off the surface using the type IIS restriction enzyme the recognition site of which is contained in the anchor oligonucleotide (FIG. 12B). The slowest migrating band corresponds to the correct elongation product whereas the presence of the faster migrating bands is indicative of the formation of side products that were not cleaved in previous cycles by the type IIS restriction enzyme the racognition site of which is contained in the splinker oligonucleotide. By reversing the architecture of the procedure as described above, all such side products remain bound to the surface according the RSPS and RLPS procedures according to the present invention. Hence only correctly elongated oligonucleotides are seen in FIG. 12C.

EXAMPLE 1

Reverse Solid Phase Synthesis

In the following the reverse solid phase synthesis as already depicted in FIG. 1A-1F and FIG. 2A-2F, respectively, is described in more detail.

a) Ligation of First and Second Oligonucleotide

In a reaction vessel 20-200 pmol of the second oligonucleotide which is not biotinylated but phosphorylated at the 5'-end, contained in a volume of 25-200 μl 1× ligase buffer are combined with 20-200 pmol of a first oligonucleotide corresponding to the first anchor oligonucleotide (having a biotin modification and being phosphorylated at the 5'-end) in 25-200 μl 1× ligase buffer and ligated via the complementary single-stranded overhang which typically comprises 1-5 bases by adding 5 U T4 DNA ligase. The ligation reaction is performed at 25° C. for 15 min in a shaker. Subsequently, the ligase is heat inactivated for 10 min at 65° C.

b) Coupling of the Ligation Product to the Matrix

Prior to use, streptavidin coated plates such as 96 well plates are re-hydrated with 200 μl 1×TE/1 M NaCl, pH 7.5, for 15 min at 25° C. in a shaker and subsequently washed twice with TE. The ligation mix as prepared in step a) is introduced into a re-hydrated well and incubated at 25° C. for 15 min. The ligation products bind to the inner side of the well by means of the biotinylated base of the first oligonucleotide. Subsequently, the supernatant is removed and the well washed four times with TE buffer.

c) Restriction Digest with Type IIS Restriction Enzymes 10-300 U of a restriction enzyme such as Eam1104I or BfuI in 25-200 μl 1× reaction buffer are added to the reaction well. The ligation product is cleaved by said restriction enzyme and releases the elongated oligonucleotide having an overhang. The reaction is run in a shaker for 60 min at a temperature, which is optimal for the restriction enzyme used, such as 37° C. Subsequently, the restriction enzyme is heat inactivated at a temperature, which is recommended by the supplier.

d) Transferring the Supernatant

The supernatant of the previous step including the elongated oligonucleotide is then transferred into a new, streptavidin-free reaction vessel and combined at a concentration of 20-200 pmol and ligase buffer with a further oligonucleotide which, in the present case as depicted in FIGS. 1A-1F, is the second anchor oligo.

The steps a)-d) as described above are repeated up to seven times with the elongated oligonucleotide.

EXAMPLE 2

Reverse Liquid Phase Synthesis

In the following the reverse liquid phase synthesis as depicted in FIGS. 3A-3E and FIGS. 4A-4E, respectively, is described in more detail.

a) Ligation of First and Second Oligonucleotide

In a reaction vessel 20-200 pmol of the non-biotinylated second oligonucleotide which is phosphorylated at the 5' end contained in 25-200 μl 1× ligase buffer are combined with 20-200 pmol of first oligonucleotide contained in 25-200 μl 1× ligase buffer, whereby the first oligonucleotide is phosphorylated at the 5' end and has a biotin modification which is the modification required for the immobilisation of the first oligonucleotide to a surface which is coated with streptavidin. Upon addition of 5 U T4 DNA ligase the first and the second oligonucleotide are ligated via their complementary single strand overhangs which have a length of 1 to 5 bases. The ligation is performed at 25° C. for 15 minutes. In a further step the ligase is heat-inactivatedd by heating the reaction to 65° C. for 10 minutes.

b) Restriction Digest with Type IIS Restriction Enzyme 10-300 U of a restriction enzyme such as Eam1104I are added to the vessel containing the ligation reaction product. The restriction enzyme is a type IIS restriction enzyme which cuts off the elongated second oligonucleotide from the first oligonucleotide which is thus reduced in length by the part of the nucleic acid molecule to be transferred to the second oligonucleotide. The respective cleavage site is contained in the sequence of the first anchor oligonucleotide. The reaction time is 60 minutes at reaction temperature which is optimum for the respective enzyme. Such reaction temperature is typically 37° C. The reaction is kept in a shaker. Subsequently, the restriction enzyme is heat inactivated at a temperature, which is recommended by the supplier.

c) Coupling of the Digested Ligation Product to the Matrix

Prior to their use, strepavidine-coated plates such as 96 well plates are re-hydrated with 200 μl 1×TE/1M NaCl, pH 7.5 for 15 minutes at 25° C. in a shaker and subsequently washed twice with TE.

The restriction reaction is subsequently added to a re-hydrated well and incubated in a shaker at 25° C. for 15 minutes. The first oligonucleotides cleaved off in preceding steps and, possibly, non-cleaved ligation products are, among others, immobilised via the biotin modification of the first oligonucleotide or the shortened first oligonucleotide to the inner wall of the well.

d) Transferring the Supernatant

The supernatant of the reaction containing the cut elongated ligation product is subsequently transferred to a new reaction vessel which does not have a streptavidin-coated surface. Ligase buffer and 20-200 pmol of the further anchor oligonucleotide, i.e. the further at least partially double-stranded oligonucleotide are added to the supernatant. This sequence of steps a) to d) is repeated preferably up to seven times using the same second oligonucleotide or the elongated oligonucleotide which in the end comprises a growing part of the nucleic acid molecule to be manufactured.

EXAMPLE 3

Semi-inverted Transposition

As outlined above, the invention provides for a highly efficient method for the manufacture of a nucleic acid molecule which may be divided into a first elongation step and, once an elongation product such as the elongated oligonucleotides described herein are available, there are subsequently combined with each other with the latter step being also referred to as transposition step or transposition procedure. The SIT method as also depicted in FIG. 7A-7C is described in more detail in the following.

a) Removal of the Moiety of the Elongated Oligonucleotide Corresponding to the Second Oligonucleotide For each well about 10-300 U of a restriction enzyme such as Esp3I which is the second type IIS restriction enzyme is added to two reaction vessels containing the first elongation block and the second elongation block in 25-200 µl reaction buffer, respectively. Both the respective recognition site and the cleavage site are contained in the sequence of the second oligonucleotide moiety thereof. Both the cut first and second elongation blocks remain immobilised to the surface as the surface of the respective reaction vessels or, more preferably, the streptavidin-coated well, which is interacting with the biotin group. The reaction time is about 60 minutes at the temperature which is optimum for the type IIS restriction enzyme. The second oligonucleotide moieties of the first and second elongation blocks are removed together with the overall supernatant. Subsequently, the immobilised restriction products are washed four times with TE buffer.

b) Removal of the First at Least Partially Double-stranded Oligonucleotide Moiety from the First Elongation Block About 10-100 U of a restriction enzyme such as Eco31I contained in 25-200 µl reaction buffer are added to the well containing the cut first elongation block which cleaves off the first oligonucleotide moiety of the cut first ligated elongated ligated oligonucleotide. The reaction time is about 60 minutes in a shaker at a reaction temperature which is optimum for the restriction enzyme such as 37° C. Subsequently, the enzyme is heat-inactivated, e.g. by maintaining the reaction at 65° C. for 10 minutes. The double-stranded nucleic acid molecule thus released is transferred together with the other components contained in the supernatant to a well containing the nucleic acid molecule moiety which is the next moiety to follow in the sequence of the nucleic acid molecule to be manufactured. The latter nucleic acid molecule is attached via the biotin modification to a surface such as the inner surface of a well.

c) Ligation Steps

The ligation of the released double-stranded oligonucleotide (step b) and the cut first elongation block (step a) occurs via T4-DNA ligase (5 U) in 50-200 µl 1× ligase buffer contained in 0.1 mM ATP, 1 mM DTT. The ligation time is about 60 minutes at 25° C. in a shaker. Subsequently, the ligase is heat-inactivated at 65° C. for 10 minutes.

The reaction cycles a) to b) are repeated that often until all of the elongation and transposition blocks are combined to form the nucleic acid molecule to be manufactured.

The features of the present invention disclosed in the specification, the claims and/or the drawings may both separately and in any combination thereof be material for realising the invention in various forms thereof.

---

The invention claimed is:

1. A method for the manufacture of a nucleic acid molecule comprising the steps of:
   (a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang;
   (b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang;
   (c) ligating the first and the second oligonucleotide via their overhangs generating a first ligation product, wherein the first and second oligonucleotides are not attached to a surface during the ligation;
   (d) immobilising the first ligation product of step (c) to the surface via the modification;
   (e) cutting the immobilised ligation product with the first type IIS restriction enzyme thus releasing an elongated oligonucleotide having an overhang;
   (f) combining the elongated oligonucleotide with a further at least partially double-stranded oligonucleotide which has a modification allowing the oligonucleotide to be coupled, to a surface, whereby the further oligonucleotide comprises a recognition site for a further type IIS restriction enzyme which cuts outside its recognition site and which oligonucleotide comprises a single-stranded overhang, and ligating the elongated second oligonucleotide and the further at least partially double-stranded oligonucleotide via their overhangs forming a further ligation product;
   (g) immobilising the further ligation product to a surface via the modification;
   (h) cutting the further ligation product with the further type IIS restriction enzyme releasing an elongated oligonucleotide having an overhang; and
   (i) optionally, repeating steps f) to h).

2. A method for the manufacture of a nucleic acid molecule comprising the steps of:
   (a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang;
   (b) providing a second at least partially double-stranded oligonucleotide whereby the oligonucleotide comprises a recognition site or a part thereof or a sequence which is complementary thereto, for a second type IIS restriction enzyme which cuts outside its recognition site, and which second oligonucleotide comprises a single-stranded overhang;
   (c) ligating the first and the second oligonucleotide via their overhangs generating a first ligation product, wherein the first and second oligonucleotides are not attached to a surface during the ligation;

(d) cutting the ligation product with the first type IIS restriction enzyme thus generating an elongated oligonucleotide having an overhang and a shortened first oligonucleotide;

(e) immobilising the shortened first oligonucleotide on a surface via the modification;

(f) providing a further at least partially double-stranded oligonucleotide which has a modification allowing the further oligonucleotide to be coupled to a surface, whereby the further oligonucleotide comprises a recognition site for a further type IIS restriction enzyme which cuts outside its recognition site and which oligonucleotide comprises a single-stranded overhang;

(g) combining the elongated oligonucleotide with the further oligonucleotide and ligating the elongated oligonucleotide and the further oligonucleotide via their overhangs forming a further ligation product;

(h) cutting the further ligation product with the further type IIS restriction enzyme generating an elongated oligonucleotide having an overhang and a shortened further oligonucleotide; and (i) optionally, repeating steps e) to h).

3. The method according to claims 1, or 2, wherein the overhang is a 5'-overhang or a 3'-overhang.

4. The method according to claim 3, wherein the overhang is selected from the group consisting a one-nucleotide overhang, a two nucleotides overhang, a three-nucleotides overhang, a four nucleotides overhang, a five-nucleotides overhang, a six-nucleotides overhang and a seven-nucleotides overhang.

5. The method according to claim 4, wherein the elongated oligonucleotide is transferred to a new reaction vessel where it is combined with the further oligonucleotide.

6. The method according to claim 5, wherein the at least partially double-stranded oligonucleotide comprises a constant region and a variable region whereby the constant region contains a recognition site for a type IIS restriction enzyme, and the variable region contains a nucleic acid sequence which corresponds to a part of the nucleic acid sequence of the nucleic acid molecule to be manufactured.

7. A method for the manufacture of a nucleic acid molecule comprising the steps of:
 (a) providing a first at least partially double-stranded oligonucleotide which has a modification allowing the oligonucleotide to be coupled to a surface, whereby the oligonucleotide comprises a recognition site for a first type IIS restriction enzyme which cuts outside its recognition site, and which oligonucleotide comprises a single-stranded overhang, and whereby the oligonucleotide comprises a part of the nucleic acid molecule to be manufactured;
 (b) immobilizing the first oligonucleotide on a surface;
 (c) cutting the first oligonucleotide with the first type IIS restriction enzyme releasing a double stranded oligonucleotide having a single stranded overhang at each end and being a part of the nucleic acid molecule to be manufactured; and
 (d) combining the double stranded oligonucleotide of step c) with a second at least partially double-stranded oligonucleotide which has a modification allowing the oligonucleotide to be coupled to a surface, whereby the oligonucleotide contains a recognition site for a second type IIS restriction enzyme which cuts outside its recognition site, and which oligonucleotide further comprises a single-stranded overhang and a part of the nucleic acid molecule to be manufactured, and ligating the double-stranded oligonucleotide of step c) with the second oligonucleotide, wherein the double-stranded oligonucleotide of step c) and the second oligonucleotide are not attached to a surface during the ligation; whereby the overhang of the second oligonucleotide is essentially complementary to the overhang of the double stranded oligonucleotide of step c).

8. The method according to claim 7, wherein the overhang generated upon cutting the first oligonucleotide with the first type IIS restriction enzyme is essentially complementary to the overhang of the second at least partially double stranded oligonucleotide.

9. A method for the manufacture of a nucleic acid molecule comprising the following steps:
 (a) providing a first ligation product, whereby the first ligation product consists of a first oligonucleotide moiety comprising a recognition site for a first type IIS restriction enzyme, a second oligonucleotide moiety comprising a recognition site for a second type IIS restriction enzyme and a third oligonucleotide moiety, whereby the third oligonucleotide moiety is a part of the nucleic acid molecule to be manufactured, and whereby the first and the second type IIS restriction enzymes each generate an overhang, whereby the overhang generated by the first type IIS restriction enzyme has a length which is different from the length of the overhang generated by the second type IIS restriction enzyme;
 (b) providing a second ligation product, whereby the second ligation product consists of a first oligonucleotide moiety comprising a recognition site for a third type IIS restriction enzyme, a second oligonucleotide moiety comprising a recognition site for a fourth type IIS restriction enzyme and a third oligonucleotide moiety, whereby the third oligonucleotide moiety is a part of the nucleic acid molecule to be manufactured, and whereby the third and the fourth type IIS restriction enzyme each generate an overhang, whereby the overhang generated by the third type IIS restriction enzyme has a length which is different from the length of the overhang generated by the fourth type IIS restriction enzyme;
 (c) cutting the first ligation product with the second restriction enzyme generating a first cut ligation product and cutting the second ligation product with the fourth restriction enzyme generating a second cut ligation product;
 (d) providing a third at least partially double-stranded oligonucleotide and ligating the third oligonucleotide with the first cut ligation product, wherein the first cut ligation product and the third oligonucleotide are not attached to a surface during the ligation, whereby the third oligonucleotide comprises an overhang which is complementary to the overhang of the first cut ligation product generated in step c) and whereby the third oligonucleotide comprises a recognition site for a fifth IIS restriction enzyme;
 (e) providing a fourth at least partially double-stranded oligonucleotide and ligating the fourth oligonucleotide to the second cut ligation product, wherein the second cut ligation product and the fourth oligonucleotide are not attached to a surface during the ligation, whereby the fourth oligonucleotide comprises an overhang which is complementary to the overhang of the second ligation product generated in step c) and whereby the fourth oligonucleotide comprises a recognition site for a sixth type IIS restriction enzyme;
 (f) immobilising the ligation product of step d) and step e) on a surface by means of a modification of the third oligonucleotide and the fourth oligonucleotide;

(g) cutting the immobilised ligation product of step d) with the fifth type IIS restriction enzyme releasing an oligonucleotide;

(h) cutting the immobilised ligation product of step e) with the third type IIS restriction enzyme; and (i) combining and ligating the oligonucleotide released according to step g) with the immobilised reaction product of step h), whereby the overhang generated by the first and the third restriction enzyme is complementary to the overhang generated by the fifth and sixth restriction enzyme.

10. The method according to claim 9, wherein the first and the third restriction enzyme are identical and/or the second and the fourth restriction enzyme are identical and/or the fifth and the sixth restriction enzyme are identical.

11. The method according to claim 10, wherein the first and the third restriction enzyme and the fifth and the sixth restriction enzyme are each a restriction enzyme generating a four-nucleotide overhang at the 3' or 5' end.

12. The method according to claim 11, wherein the second and the third restriction enzyme is a restriction enzyme creating an overhang having a length which is selected from the group consisting of one, two, three, four, five and six nucleotides.

13. The method according to claim 12, wherein the first and the second restriction enzyme is Esp3I or Eco31I and the fifth and the sixth restriction enzyme is Eco3 1I or Esp3I.

14. The method according to claim 13, wherein the ligation product of step i) is used as a first ligation product and/or a second ligation product and steps a) to i) are repeated one or several times.

15. The method according to claim 14, wherein the third moiety is arranged between the moieties of the oligonucleotides containing the restriction site for the type IIS restriction enzymes.

16. The method according to claim 15, wherein the first and he second ligation products are provided in separate reaction vessels.

* * * * *